(12) United States Patent
Perreault et al.

(10) Patent No.: US 9,012,140 B2
(45) Date of Patent: Apr. 21, 2015

(54) TARGET-DEPENDENT NUCLEIC ACID ADAPTER

(75) Inventors: Jean-Pierre Perreault, Fleurimont (CA); Luncien Junior Bergeron, Sherbrooke (CA)

(73) Assignee: Societe de Commercialisation des Produits de la Recherche Appliquée Socpra Sciences et Génie S.E.C., Sherbrooke, Quebec (CA)

( * ) Notice: Subject to any disclaimer, the term of this patent is extended or adjusted under 35 U.S.C. 154(b) by 1550 days.

(21) Appl. No.: 11/631,689

(22) PCT Filed: Jul. 6, 2005

(86) PCT No.: PCT/CA2005/001051
§ 371 (c)(1),
(2), (4) Date: Apr. 18, 2008

(87) PCT Pub. No.: WO2006/002547
PCT Pub. Date: Jan. 12, 2006

(65) Prior Publication Data
US 2008/0268516 A1      Oct. 30, 2008

(51) Int. Cl.
 C12Q 1/68        (2006.01)
 C12N 15/11       (2006.01)
 A61K 48/00       (2006.01)
 C12N 15/113      (2010.01)
 C07H 21/04       (2006.01)

(52) U.S. Cl.
 CPC ........ *C12N 15/1131* (2013.01); *C12N 2310/11* (2013.01); *C12N 15/111* (2013.01); *C12N 2310/3519* (2013.01); *C12N 2320/50* (2013.01); *C12N 2310/123* (2013.01)

(58) Field of Classification Search
 CPC ........... C12Q 2521/337; C12Q 1/6811; C12Q 2521/345; C12N 2310/14; C12N 2310/121; C12N 2310/127; C12N 15/111; C12N 2310/12
 USPC ......... 435/6, 91.1, 91.31, 455; 536/23.1, 24.5
 See application file for complete search history.

(56) References Cited

U.S. PATENT DOCUMENTS

| 7,148,044 | B1 * | 12/2006 | Perreault et al. ........... 435/91.31 |
| 2004/0009510 | A1 * | 1/2004 | Seiwert et al. .................... 435/6 |
| 2005/0239061 | A1 * | 10/2005 | Marshall et al. .................. 435/6 |
| 2006/0035275 | A1 * | 2/2006 | Ward et al. ........................ 435/6 |

FOREIGN PATENT DOCUMENTS

WO      WO 99/55856      11/1999

OTHER PUBLICATIONS

Tang et al., Nuc. Acids Res., vol. 21, No. 11, pp. 2729-2735 (1993).*
Kuwabara et al., 2000, Trends in Biotechnology, 18: 462-468.
Marshall et al., 1999, Nature Structural Biology, 6: 992-994.
Bergeron et al., 2003, Current Medicinal Chemistry, 10: 2589-2597.
Lévesque et al., 2002, RNA, 8: 464-477.
Bergeron and Perreault, 2005, Nucleic Acids Research, 33: 1240-1248.
Bergeron and Perreault, 2002, Nucleic Acids Research, 30: 4682-4691.
D'Anjou et al., 2004, Journal of Biological Chemistry, 279: 14232-14239.
Nassal, 1992, Journal of Virology, 66: 4107-4116.
Hicham et al., 2000, Antiviral Research, 46: 181-193.
Wilson and Szostak, 1999, Annu. Rev. Biochem., 68: 611-647.
Ananvoranich and Perreault, 2000, Biochemical and Biophysical Research Communications, 270: 600-607.
Deschênes et al., 2000, Antisense & Nucleic Acid Drug Development, 10: 53-61.
Deschênes et al., 2003, Nucleic Acid Research, 31: 2087-2096.
Kieft et al., 1999, J. Mol. Biol., 292: 513-529.
Sledz et al., 2003, Nature Cell Biology, 5: 834-839.
Lewin and Hauswirth, 2001, TRENDS in Molecular Medicine, 7: 221-228.
Lévesque et al., 2007, PLoS ONE, 7, e673, 1-7.
Burke et al., 2002, Biochemistry, 41: 6588-6594.
Soukup et al., 1999, PNAS, 96: 3584-3589.
Wang et al., 2002, Nucleic Acids Research, 30: 1735-1742.
Robertson and Ellington, 1999, Nature Biotechnology, 17: 62-66.
Soukup and Breaker, 1999, TRENDS in Biotechnology, 17: 469-476.
Silverman, 2003, RNA, 9: 377-383.
Roy et al., 1999, Nucleic Acids Research, 27: 942-948.
Lucier et al., 2006, BMC Bioinformatics, 7:480, pp. 1-8.
D'Anjou et al. 2011, Translational Oncology 4: 157-172S.
Lainé et al., 2011, RNA Biology, 8:343-353.
Robichaud et al., 2008, Nucleic Acids Res, 35:4609-4620.
Fiola et al., 2006, Appl. Env. Microb, 72:869-879.

* cited by examiner

*Primary Examiner* — Dana Shin
(74) *Attorney, Agent, or Firm* — Norton Rose Fulbright Canada LLP

(57) ABSTRACT

In accordance with the present invention, there is provided a nucleic acid target-dependent adapter linked to a nucleic acid sequence. The adapter comprises linked together a biosensor having a specific sequence complementary to a target sequence of a substrate, the biosensor improving the specificity of the nucleic acid sequence for the substrate, and a blocker stem sequence complementary to a portion of the nucleic acid sequence. In absence of the target sequence of the substrate, the blocker stem sequence forms an intramolecular stem with the nucleic acid sequence linked thereto, preventing exposition of the sequence of the nucleic acid sequence, thus locking the nucleic acid sequence so linked to the adapter in an inactive conformation, and in presence of the target sequence, the blocker stem sequence dissociating from the nucleic acid sequence, thus exposing the nucleic acid sequence linked to the adapter in an active conformation.

11 Claims, 35 Drawing Sheets

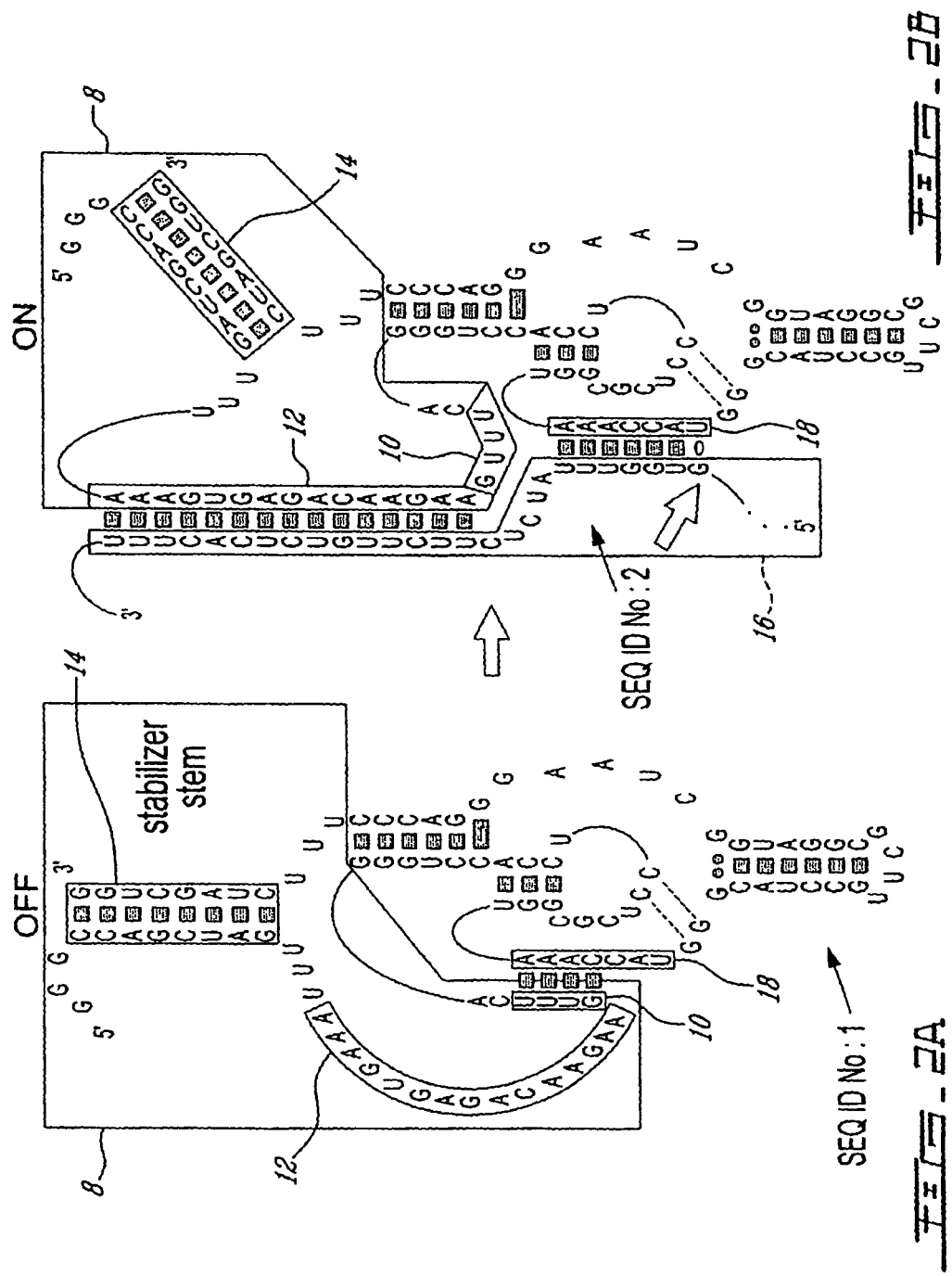

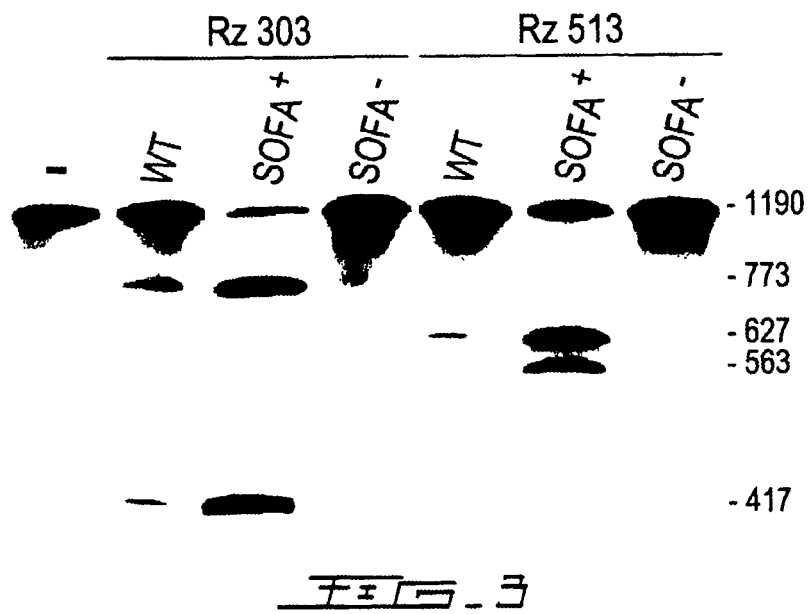
FIG_3
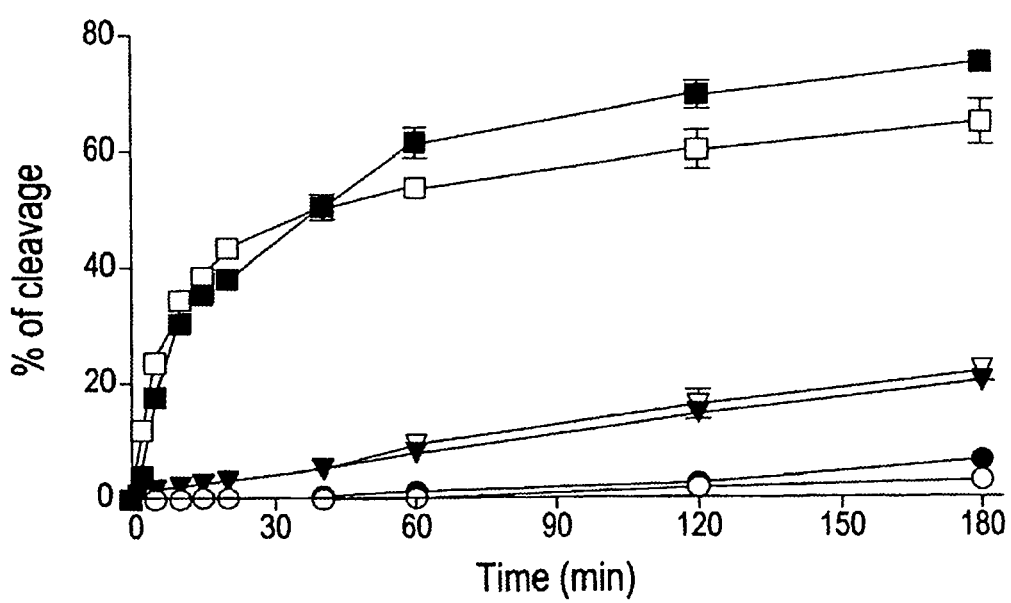
FIG_4

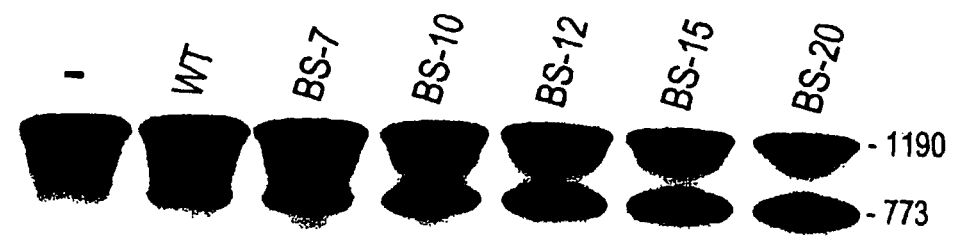
FIG. 5
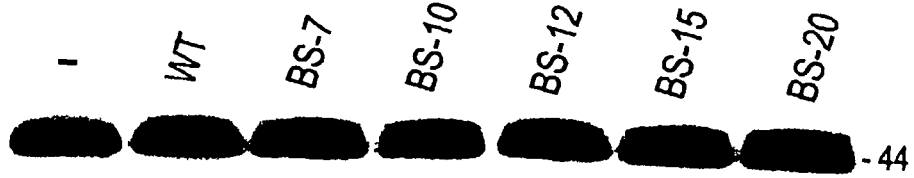
-XC
FIG. 6

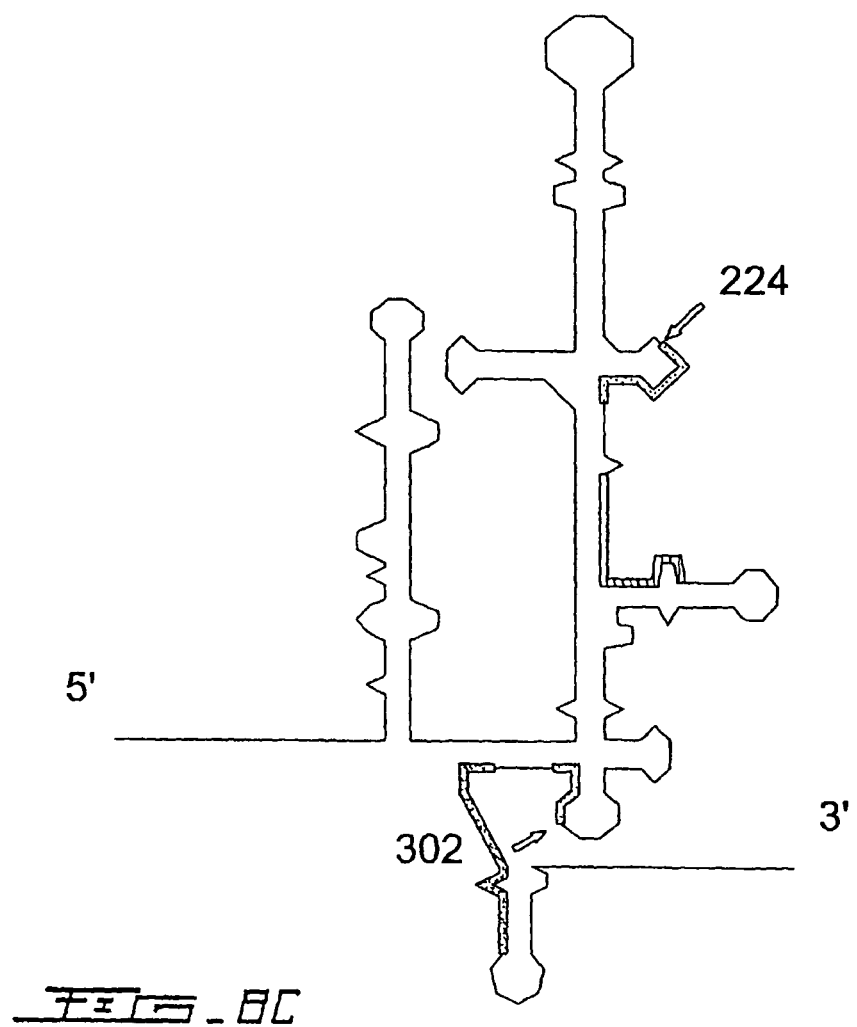
FIG_8C

| SEQ ID | aA<br>SEQ ID No 42 / No 50 | bB<br>SEQ ID No 43 / No 51 | cC<br>SEQ ID No 44 / No 52 | dD<br>SEQ ID No 45 / No 53 |
|---|---|---|---|---|
| | C - G<br>U - A<br>C - G<br>U - A<br>G - C<br>U - A<br>U - A<br>C - G<br>U - A<br>U - A | U - A<br>C - G<br>U - A<br>G - C<br>A - U<br>C - G<br>U - A<br>C - G<br>U - A<br>A - U | C - G<br>A - U<br>A - U<br>G - C<br>U - A<br>C - G<br>G - C<br>U - A<br>G - C<br>A - U | U - A<br>C - G<br>C - G<br>U - A<br>A - U<br>U - A<br>U - A<br>C - G<br>C - G<br>C - G |
| | eE | fF | gG | hH |
| | U - A<br>C - G<br>A - U<br>G - C<br>A - U<br>C - G<br>C - G<br>U - A<br>A - U<br>G - C | C - G<br>C - G<br>G - C<br>U - A<br>A - U<br>U - A<br>U - A<br>A - U<br>G - C<br>U - A | U - A<br>U - A<br>C - G<br>A - U<br>A - U<br>A - U<br>C - G<br>C - G<br>G - C<br>U - A | C - G<br>A - U<br>U - A<br>G - C<br>A - U<br>G - C<br>U - A<br>A - U<br>C - G<br>G - C |
| SEQ ID | No 46 / No 54 | No 47 / No 55 | No 48 / No 56 | No 49 / No 57 |

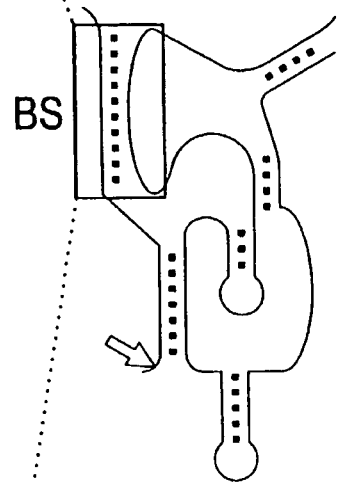

FIG._10A

| | Ribozyme BS | $K_{obs}$ (min$^{-1}$) | |
|---|---|---|---|
| 0 | ₁GAGACAAGAA₁₀ | 0.107 | SEQ ID No : 58 |
| 1 | CAGACAAGAA | 0.029 | SEQ ID No : 59 |
| | GUGACAAGAA | 0.022 | SEQ ID No : 60 |
| | GCGACAAGAA | 0.022 | SEQ ID No : 61 |
| | GACACAAGAA | 0.020 | SEQ ID No : 62 |
| | GAGUCAAGAA | 0.012 | SEQ ID No : 63 |
| | GAGAGAAGAA | 0.022 | SEQ ID No : 64 |
| | GAGACUAGAA | 0.011* | SEQ ID No : 65 |
| | GAGACCAGAA | 0.013 | SEQ ID No : 66 |
| | GAGACAUGAA | 0.007 | SEQ ID No : 67 |
| | GAGACAACAA | 0.016 | SEQ ID No : 68 |
| | GAGACAAGUA | 0.014* | SEQ ID No : 69 |
| | GAGACAAGCA | 0.014 | SEQ ID No : 70 |
| | GAGACAAGAU | 0.020 | SEQ ID No : 71 |
| 2 | GUGACAAGUA | 0.013 | SEQ ID No : 72 |
| | GAGAGUAGAA | 0.015* | SEQ ID No : 73 |
| | GAGACUAGUA | 0.007* | SEQ ID No : 74 |
| | GAGACCAGCA | 0.006 | SEQ ID No : 75 |
| 3 | CUGACUAGAA | 0.006 | SEQ ID No : 76 |
| | GUGACUAGUA | 0.007 | SEQ ID No : 77 |
| | GAGACUACUA | 0.007 | SEQ ID No : 78 |
| 4 | CUCACAAGAU | 0.006 | SEQ ID No : 79 |
| | GUGACUAGUU | 0.001 | SEQ ID No : 80 |
| | GACACAUCUA | 0.002 | SEQ ID No : 81 |

FIG. 11A

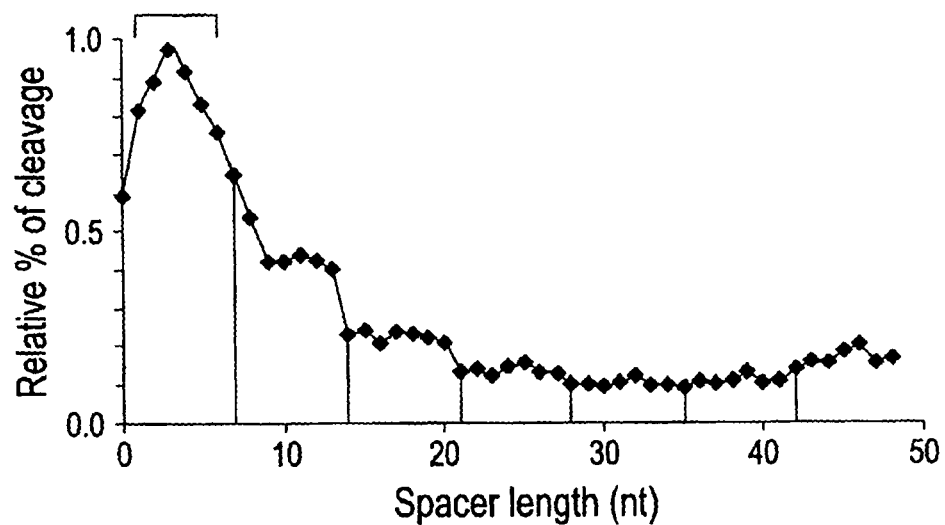
FIG_13C
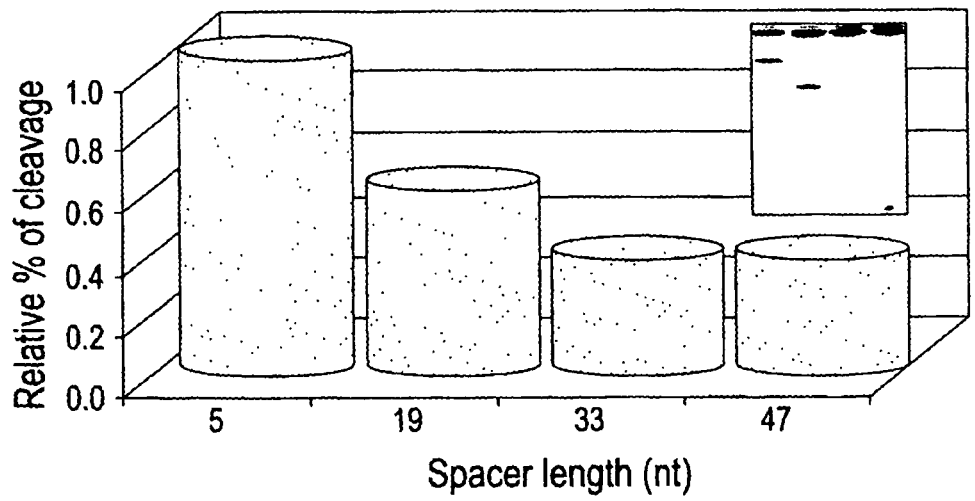
FIG_13D

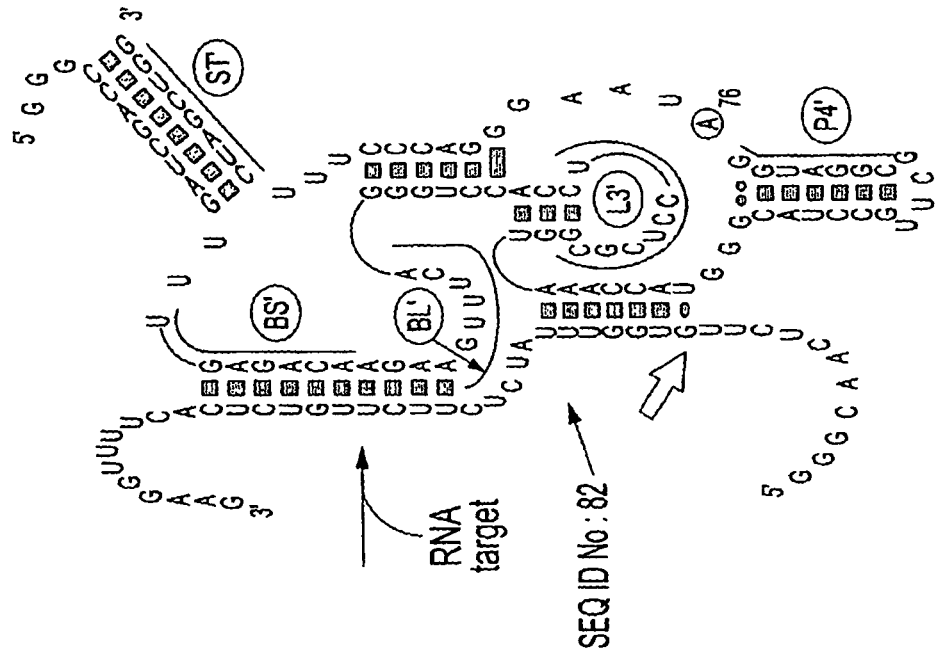
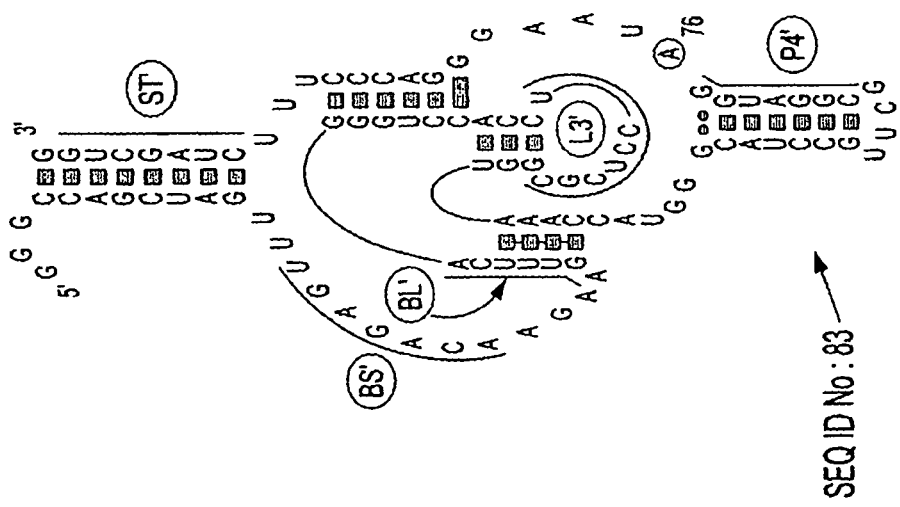
Fig. 15A

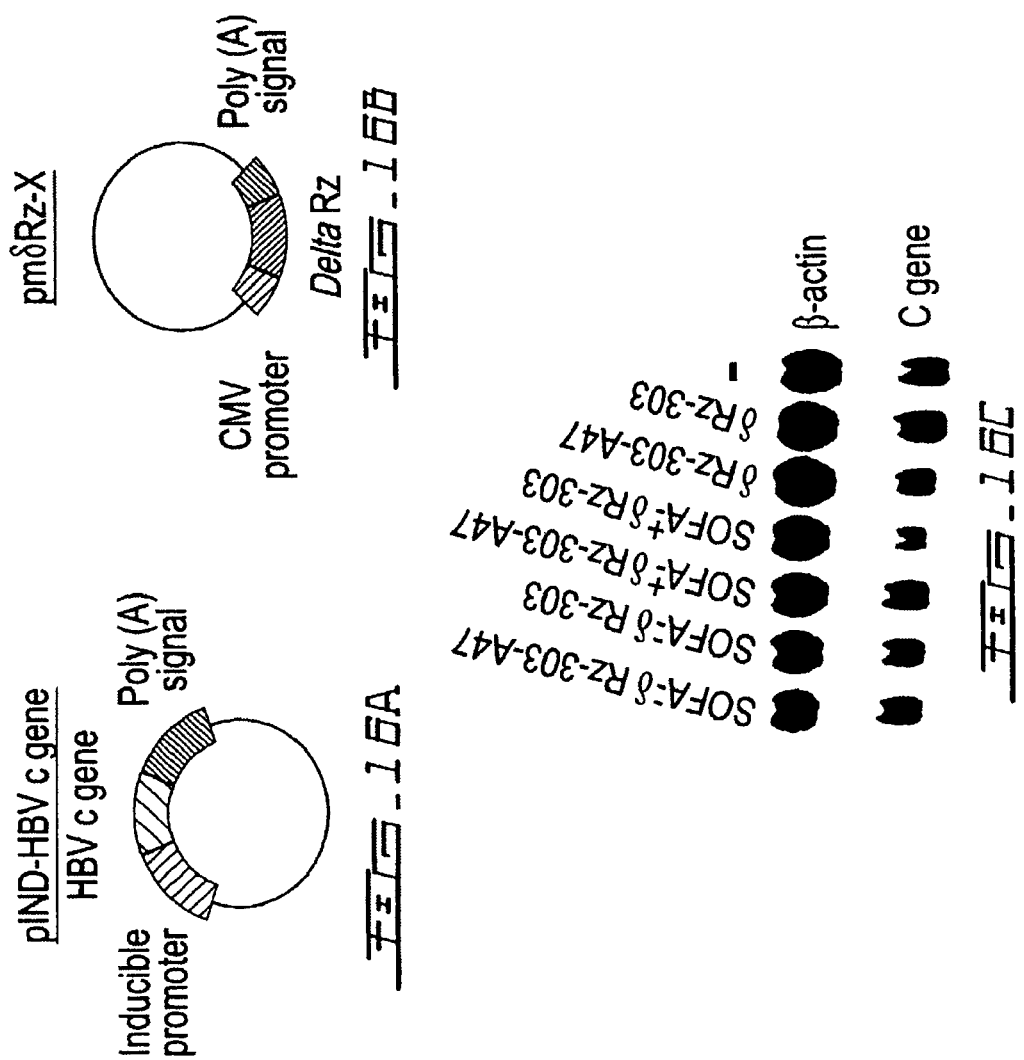

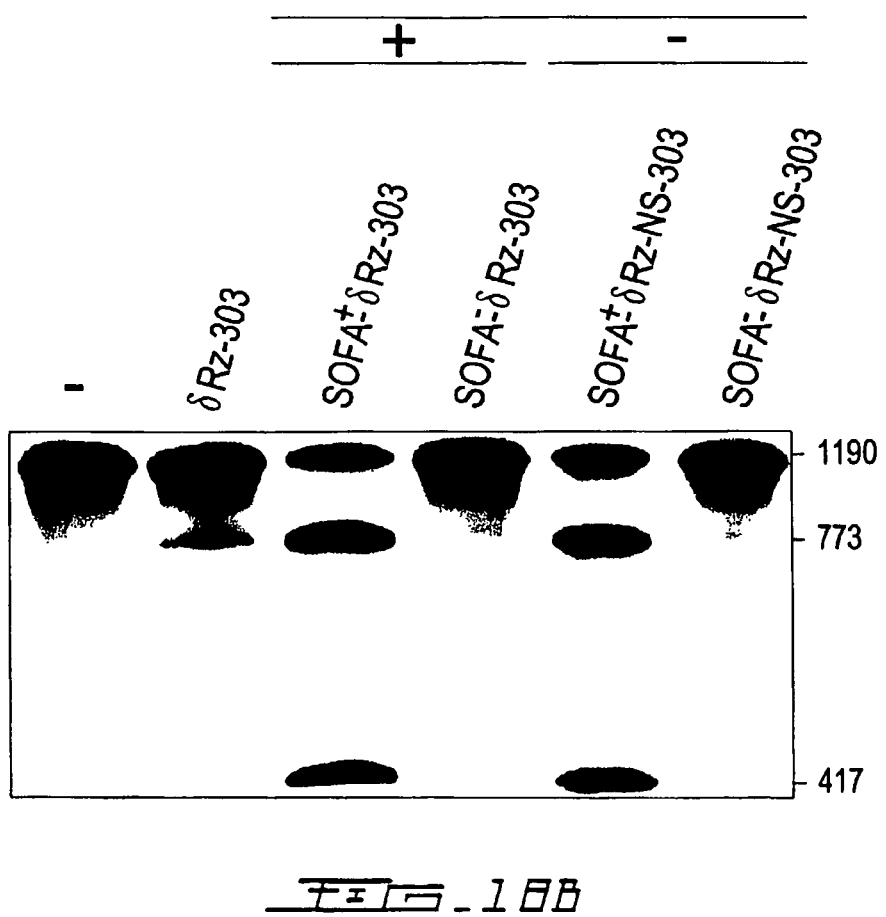
FIG_18B

| Nucleic acid enzyme | WT | off conformation |
|---|---|---|
| DNazyme (Cleavage activity) (SEQ ID No) | (93) | (101) |
| hammerhead Rz (Cleavage activity) (SEQ ID No) | (90) | (98) |

| Nucleic acid enzyme | on conformation |
|---|---|
| DNazyme (Cleavage activity) (SEQ ID No) | (97) / (101) |
| hammerhead Rz (Cleavage activity) (SEQ ID No) | (94) / (98) |

| Nucleic acid enzyme | WT | off conformation |
|---|---|---|
| hairpin Rz (Cleavage activity) | 5'-AAACAG AGA A GUCAA-UA-3'<br>(hairpin structure with loops containing A, G, C, U residues; CCAU loop, ACAC-GGU loop) | BL<br>3'-G<br>A-U<br>C-G<br>G-A<br>A-G<br>C-A<br>G-U<br>U-G<br>A<br>5'-GACAUAACGAGUAAAC<br>BS<br>(with CCAU loop and ACAC-GGU loop structure) |
| (SEQ ID No) | (91) | (99) |

FIG. 19C

| Nucleic acid enzyme | |
|---|---|
| hairpin Rz (Cleavage activity) | 3'-GGACUGUAUUGCUCAUUUGUCCUGACAGUG CUAGAAG CUAGGG-5' (95)<br>5'-GACAUAACGAGUAAACAG GUCAA-UACUUCUG-3' (99)<br>BS    A A    GA    C-G    BL<br>                                  A-U<br>                                AG-CC U<br>                             A       A   A<br>                          A           C-G<br>                      C            A-U<br>                   A              C-G<br>              A                 G U |
| (SEQ ID No) | | on conformation

FIG. 19D

| Nucleic acid enzyme | WT | off conformation |
|---|---|---|
| hairpin Rz (Ligation activity) | 5'-AAACAG AGA A GUCAA-UA-3'<br>C-G<br>C-G<br>AG-CCAU<br>A A<br>A C-G U<br>A A-U A<br>A C-G C<br>ACA G U<br>G U | 5'-GACAUAACGAGU AAAC GCGAAUCUUCGAU-3'<br>BS A BL BS<br>A-U<br>G-C<br>A-U<br>G-C<br>A-U<br>U-G<br>C AG-CCAU<br>A A<br>A A C-G U<br>A A-U A<br>A C-G C<br>ACA G U<br>G U |
| (SEQ ID No) | (92) | (100) |

FIG. 19E

| Nucleic acid enzyme | on conformation |
|---|---|
| hairpin Rz (Ligation activity) (SEQ ID No) | (96) (100) |

FIG. 19F

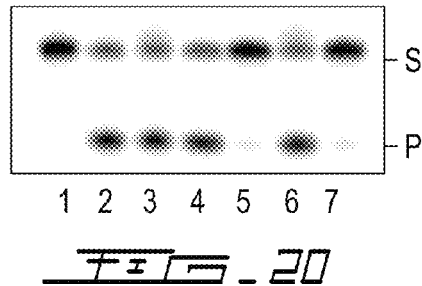
FIG. 20
siRNA
5'-GGGCGGCGGUUGGUGUUACGUUUGG-3'    SEQ ID NO : 102
FIG. 21A
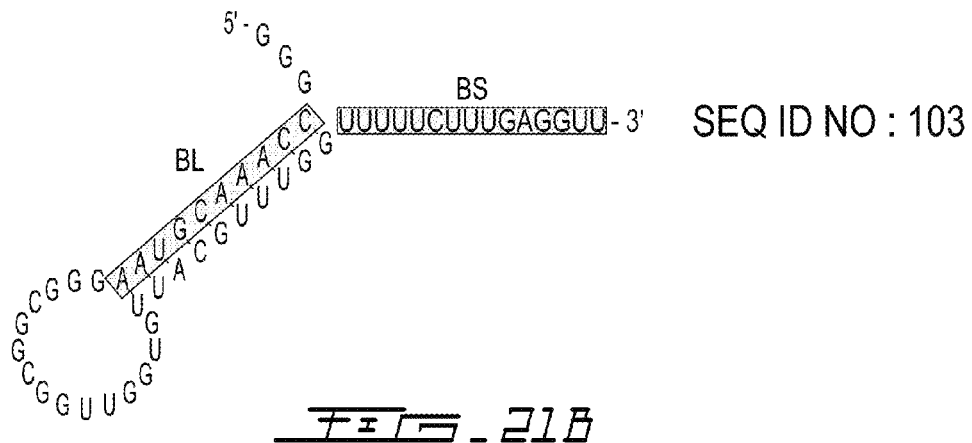
FIG. 21B
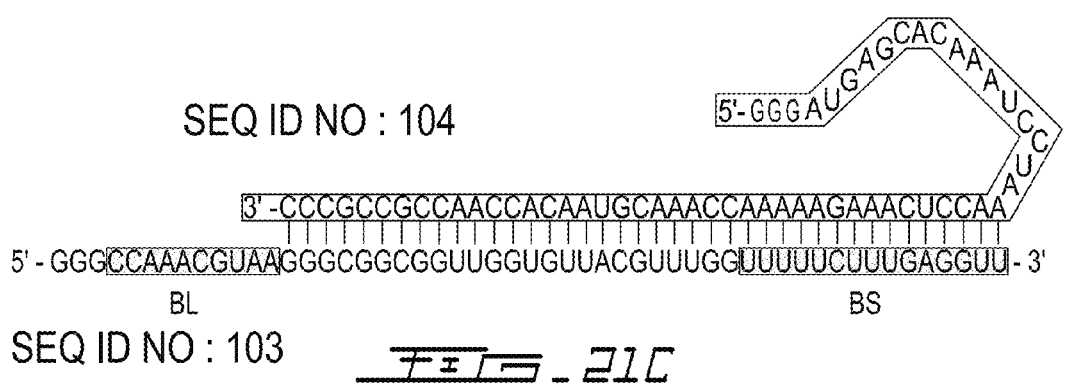
FIG. 21C

TARGET-DEPENDENT NUCLEIC ACID ADAPTER

RELATED APPLICATIONS

The present application claims the benefit of International Application Number PCT/CA05/001051, filed Jul. 6, 2005, now abandoned, incorporated herein by reference in its entirety.

TECHNICAL FIELD

The present invention relates to the field of target-dependent switch adapters for nucleic acid sequences, and more particularly to adapters for nucleic acid sequences such as ribozymes.

BACKGROUND OF THE INVENTION

Discoveries in the basic realm of molecular biology over the past ten years have led to the realization that RNA has a series of distinct capabilities and biological activities previously unsuspected. The most important of these novel RNA-level discoveries has been the finding that RNA can be an enzyme as well as an information carrier.

Various RNA molecules have one or more enzymatic activities, such as an endoribonuclease activity which acts to cleave other RNA molecules. Such activity is termed intermolecular cleaving activity. These enzymatic RNA molecules are derived from an RNA molecule which has an activity which results in its own cleavage and splicing. Such self-cleavage is an example of an intramolecular cleaving activity.

Since 1982, several unexpected diseases caused by RNA-based pathogenic agents have emerged. These include the lethal Acquired Immune Deficiency Syndrome (AIDS) and delta hepatitis (also called Hepatitis D), a particularly virulent form of fulminant hepatitis caused by a viroid-like RNA agent. These blood-borne diseases are spread at the RNA level, manifest themselves in cells of patients, and are by now present within the bloodstream of millions of individuals.

Conventional biotechnology, with its reliance on recombinant DNA methods and DNA-level intervention schemes, has been slow to provide valid approaches to combat these diseases.

The potential of ribozymes (RNA enzymes) to catalyze the cleavage of RNA substrates makes them attractive molecular tools. Ribozymes are an interesting alternative to RNA interference approach that seems to trigger immunological responses. Many efforts were directed at increasing the substrate specificity of ribozyme cleavage, which can be considered as a limit to their utilization. For example, allosteric ribozymes for which the catalytic activity is regulated by an independent effector, have been developed.

Delta ribozymes, derived from the genome of hepatitis delta virus (HDV), are metalloenzymes. Like other catalytically active ribozymes, namely hammerhead and hairpin ribozymes, the delta ribozymes cleave a phosphodiester bond of their RNA substrates and give rise to reaction products containing a 5'-hydroxyl and a 2',3'-cyclic phosphate termini. Two forms of delta ribozymes, namely genomic and antigenomic, were derived and referred to by the polarity of HDV genome from which the ribozyme was generated. Both HDV strands forms exhibit self-cleavage activity, and it has been suggested that they are involved in the process of viral replication. This type of activity is described as cis-acting delta ribozymes.

Like other ribozymes, delta ribozymes have a potential application in gene therapy in which an engineered ribozyme is directed to inhibit gene expression by targeting either a specific mRNA or viral RNA molecule. A very low concentration (<0.1 mM) of $Ca^{2+}$ and $Mg^{2+}$ is required for delta ribozyme cleavage.

With respect to the structure of the δ ribozyme, it folds into a compact secondary structure that includes pseudoknots (for reviews see Bergeron et al., Current Med. Chem. 10, 2589-2597, 2003). This structure is composed of one stem (the P1 stem), one pseudoknot (the P2 stem is a pseudoknot in the cis-acting version), two stem-loops (P3-L3 and P4-L4) and three single-stranded junctions (J1/2, J1/4 and J4/2). Both the J1/4 junction and the L3 loop are single-stranded in the initial stages of folding, but are subsequently involved in the formation of a second pseudoknot that consists of two Watson-Crick base pairs (the P1.1 stem). In terms of general organization, the P1 and P3 stems, along with the J4/2 junction, form the catalytic center, while the P2 and P4 stems are located on either side of the catalytic centre and stabilize the overall structure.

The binding domain of δRz (the P1 stem) is composed of one G-U wobble base pair followed by six Watson-Crick base pairs. In addition, the nucleotides from position −1 to −4 of the substrate, that is those adjacent to the scissile phosphate, were shown to contribute to the ability of a substrate to be cleaved efficiently. Thus, the substrate specificity of δRz cleavage is based on a total of 11 nucleotides, which might be a limiting factor when trying to specifically target an RNA species in a cell. Because the P1 stem is located within its catalytic center, all attempts to modify the length of this stem result in the loss of catalytic ability.

In International publication WO99/55856 (Jean-Pierre Perreault et al.), the entire content of which is hereby incorporated by reference, filed in the name of Université de Sherbrooke, there is disclosed a nucleic acid enzyme for RNA cleavage, and more particularly a delta ribozyme and mutants thereof.

In U.S. Pat. No. 5,225,337 (Hugh D. Robertson et al.), issued on Jul. 6, 1993, there are disclosed ribozymes derived from a specific domain present in the hepatitis delta virus (HDV) RNA for specifically cleaving targeted RNA sequences and uses thereof for the treatment of disease conditions which involve RNA expression, such as AIDS. These ribozymes consist in at least 18 consecutive nucleotides from the conserved region of the hepatitis delta virus between residues 611 and 771 on the genomic strand and between residues 845 and 980 on the complementary anti-genomic strand. These ribozymes are proposed to fold into an axe-head model secondary structure. According to this model structure, these ribozymes require substrate base paired by 12-15 nucleotides. More specifically, a substrate bound to the ribozyme through the formation of two helices. A helix is located upstream to the cleavage site (i.e. in 5' position) while the second helix is located downstream to the cleavage site (i.e. in 3' position).

In U.S. Pat. No. 5,625,047 (Michael D. Been et al.), issued on Apr. 29, 1997, there are disclosed enzymatic RNA molecules proposed to fold into a pseudoknot model secondary structure. These ribozymes were proposed to cleave at almost any 7 or 8 nucleotide site having only a preference for a guanosine base immediately 3' to the cleavage site, a preference for U, C or A immediately 5' to the cleavage site, and the availability of a 2' hydroxyl group for cleavage to occur. The specificity of recognition of these ribozymes is limited to 6 or 7 base pairing nucleotides with the substrate and a preference of the first nucleotide located 5' to the cleavage site. Neither tertiary interaction(s) between the base paired nucleotides and another region of the ribozyme, nor single-stranded nucleotides are involved to define the specificity of recognition of these ribozymes. Because the recognition features were included in a very small domain (i.e. 6 or 7 base paired nucleotides) in order to exhibit the desired activity, these ribozymes have a limited specificity, and thus, not practical for further clinical applications.

It would be highly desirable to be provided with a new ribonucleic acid, target-dependent adapter to increase specificity of the nucleic acid for its target.

SUMMARY OF THE INVENTION

One aim of the present invention is to provide a new ribonucleic acid, target-dependent adapter to increase efficiency and specificity (prevents cleavage of an inappropriate target) of cleavage of a ribonucleic acid for its target. Moreover, the adapter of the present invention can be used as a switch to turn on or off a ribonucleic acid enzyme by controlling availability of the target of this enzyme. Whenever the target is not available, the adapter turns off the enzyme by adopting an inactive conformation and when the substrate or the target is detected by the adapter, the enzyme is turned on in an active conformation. The same principle in the present invention is also applicable to any nucleic acid, where such nucleic acid when linked to the adapter would be hidden (in an inactive conformation) or prevented to react with anything else in absence of a target and would be made available to react with its target upon detection of said target by the adapter.

It is reported herein below a new switch made by molecular engineering of a ribozyme, possessing a biosensor module that switches the cleavage from off to on in the presence of the target substrate. Both proof-of-concept and mechanism of action of this man-made switch are reported herein below using a modified hepatitis delta virus ribozyme that can cleave RNA transcripts derived from both the hepatitis B and C viruses. This new approach provides a highly specific and improved tool for functional genomics and gene therapy. In fact, the same modifications made to the Hepatitis Delta Virus ribozyme can be made to other ribozymes as well as other RNA- and DNA-based approaches. Moreover, the switch of the present invention can be modified to be adapted to any nucleic acid sequences that target a substrate, making the switch a new versatile and powerful tool, allowing to increase the specificity of the nucleic acid for its substrate or target, also allowing to increase the cleavage efficacy of the ribozyme for its substrate or target, and to abolish the non-specific pairing therefore reducing false positive reactions.

In accordance with the present invention there is provided a target-dependent nucleic acid adapter adapted to be matched to a substrate comprising a target sequence, said adapter having a nucleic acid sequence comprising linked together:
  i) a blocker stem sequence complementary to a portion of said nucleic acid sequence; and
  ii) a biosensor sequence having a sequence complementary to said target sequence, said biosensor improving the specificity of the nucleic acid sequence for said target sequence,
wherein in absence of the target sequence of said substrate, said blocker stem sequence forms an intramolecular stem with said nucleic acid sequence linked thereto, preventing exposition of the nucleic acid sequence, thus locking said nucleic acid sequence of the adapter in an inactive conformation, and, in presence of said target sequence of said substrate, said biosensor sequence forming conventional Watson-Crick base pairs with said target sequence and said blocker stem sequence dissociating from the intramolecular stem, thus exposing said nucleic acid sequence of said adapter in an active conformation.

The target dependent nucleic acid adapter may also comprises sequences forming a stabilizing stem, whereby the 3'-end of the adapter so linked to said nucleic acid sequence is paired up, thus preventing or reducing degradation of said nucleic acid sequence. The stabilizing stem may have for example two complementary strands, a first strand of which is linked to the 5'-end of the biosensor, and a second strand of which that is complementary to the first strand and that is adapted to be linked at its 5'-end to the 3'-end of the nucleic acid sequence, thus preventing exposure of a single stranded 3'-end sequence susceptible to degradation by cellular nuclease.

In one embodiment of the invention, the first strand of the stabilizing stem has a sequence as set forth from residue 4 to 11 of SEQ ID NO:1 and the second strand of the stabilizing stem has a sequence as set forth from residue 96 to 103 of SEQ ID NO:1.

Still in one embodiment of the invention, the blocker stem sequence has a sequence specific for a ribozyme, such as ribozyme delta.

In a further embodiment of the invention, the biosensor has a sequence as set forth from residue 15 to 29 of SEQ ID NO:1. The blocker stem sequence has in one embodiment a sequence as set forth from residue 30 to 33 of SEQ ID NO:1. Preferably, the blocker stem sequence is linked downstream of the biosensor.

Still in accordance with the present invention, there is provided a method for improving specificity of a nucleic acid sequence for a target sequence, said method comprising the steps of attaching to said nucleic acid sequence a target-dependent nucleic acid adapter having a nucleic acid sequence comprising:
  i) a blocker stem sequence complementary to a portion of said nucleic acid sequence; and
  ii) a biosensor sequence having a sequence complementary to said target sequence, said biosensor improving the specificity of the nucleic acid sequence for said target sequence,
wherein in absence of the target sequence of said substrate, said blocker stem sequence forms an intramolecular stem with said nucleic acid sequence linked thereto, preventing exposition of the nucleic acid sequence, thus locking said nucleic acid sequence of the adapter in an inactive conformation, and, in presence of said target sequence of said substrate, said biosensor sequence forming conventional Watson-Crick base pairs with said target sequence and said blocker stem sequence dissociating from the intramolecular stem, thus exposing said nucleic acid sequence of said adapter in an active conformation.

Further in accordance with the present invention, there is provided a method for turning on or off an enzymatic activity of a nucleic acid molecule having an enzymatic activity, said method comprising the steps of attaching to said nucleic acid molecule a nucleic acid target dependent adapter having a nucleic acid sequence comprising:
  i) a blocker stem sequence complementary to a portion of said nucleic acid sequence; and
  ii) a biosensor sequence having a sequence complementary to said target sequence, said biosensor improving the specificity of the nucleic acid sequence for said target sequence,
wherein in absence of the target sequence of said substrate, said blocker stem sequence forms an intramolecular stem with said nucleic acid sequence linked thereto, preventing exposition of the nucleic acid sequence, thus locking said nucleic acid sequence of the adapter in an inactive conformation, turning off the enzymatic activity and, in presence of said target sequence of said substrate, said biosensor sequence forming conventional Watson-Crick base pairs with said target sequence and said blocker stem sequence dissociating from the intramolecular stem, thus exposing said nucleic acid sequence of said adapter in an active conformation, turning on the enzymatic activity.

In accordance with one embodiment of the present invention, there is also provided a target-specific activatable/deactivatable ribonuclease adapted to be matched to a substrate comprising a target sequence, said ribonuclease having a nucleic acid sequence comprising linked together:
   i) a ribonuclease sequence, or an active fragment thereof;
   ii) a blocker stem sequence complementary to a portion of said ribonuclease sequence, said blocker sequence being linked upstream of the ribonuclease sequence; and
   iii) a biosensor sequence having a sequence complementary to said target sequence, said biosensor improving the specificity of the ribonucleic acid sequence for said target sequence, said biosensor being linked to the blocker sequence,
wherein in absence of the target sequence of said substrate, said blocker sequence forms an intramolecular stem with the ribonuclease sequence linked thereto, thus locking said ribonuclease in an inactive conformation, and, in presence of the target sequence of said substrate, said biosensor sequence forming conventional Watson-Crick base pairs with said target sequence and said blocker stem sequence dissociating from the intramolecular stem, thus exposing said ribonuclease in an active conformation.

In a further embodiment of the invention, the target-specific activatable/deactivatable ribonuclease has a sequence as set forth in SEQ ID NO:1.

For the purpose of the present invention the following terms are defined below.

The term "RNA with enzymatic or effector activity" is intended to mean any RNA that has an active and inactive conformation or any RNA that has an enzymatic activity or that has an effect on either the transcription of said target RNA or a downstream event following transcription of said RNA.

The term "substrate" can be substituted by "target" or "target substrate" or the expression "substrate or target" throughout the application. It is to be recognized and understood that the substrate contains a target sequence.

The term "adapter" can be substituted by the term "switch" throughout the application.

The term "Biosensor" can be abbreviated as "BS" or "BSO"

The term "SOFA module" can be substituted by the term "SOFA adapter" throughout the application.

The term "Target dependant nucleic acid adapter" can be substituted by the term "nucleic acid target dependent adapter" throughout the application.

In accordance with one embodiment of the present invention, there is provided a method for turning on/off an enzymatic activity of a nucleic acid molecule having an enzymatic activity. The target-specific activatable/deactivatable adapter can be adapted to any type of nucleic acid enzymes catalyzing the modification of nucleic acid substrates (i.e. modifying enzymes such as kinases, ligases, methylases, ribonucleases, aminoacyl-tRNA synthetases, etc).

BRIEF DESCRIPTION OF THE DRAWINGS

FIGS. 2A and 2B illustrate the specific structure and sequence of the SOFA-ribozyme (SEQ ID NO:1), in the off (FIG. 2A) and on (FIG. 2B) conformations, in accordance with one embodiment of the present invention, where the arrow in the on conformation indicates the cleavage site on the target (SEQ ID NO:2);

FIG. 3 illustrates an autoradiogram of a denaturing 6% PAGE gel for the analysis of the cleavage reaction of the HBV-derived target by the original—(Wild Type) (WT), SOFA-δRz-303 and SOFA-δRz-513 ribozymes;

FIG. 4 illustrates a graphical representation of time courses for the cleavage reactions of SOFA$^+$ (squares), SOFA$^-$ (circles) and the original (inversed triangles) ribozyme versions of δRz-303 (filled) and δRz-513 (empty);

FIG. 5 illustrates an autoradiogram of a denaturing 6% PAGE gel showing the cleavage assays of the HBV-derived substrate by SOFA-δRz-303 bearing a biosensor stem of various lengths (BS-X, where X indicates the length of the stem) to characterize the SOFA-δRz-303;

FIG. 6 illustrates an autoradiogram of a 20% PAGE gel showing the cleavage assays of the HBV-derived substrate of 44 nucleotides by a SOFA-δRz-303 bearing a biosensor stem of various lengths (BS-X, where X indicates the length of the stem);

FIGS. 8A to 8F illustrate an analysis of the substrate specificity of various SOFA-ribozymes, where FIGS. 8A to 8C show a schematic representation of the various substrates, while FIGS. 8D to 8F illustrate the autoradiograms of denaturing 6% or 20% PAGE gels performed for these cleavage assays;

FIG. 10A illustrates the stem formed between 8 pairs of substrate (a to h, left) and ribozyme biosensor (A to H, right) sequences;

FIG. 11A illustrates twenty-three biosensor sequence variants examined for their ability to cleave the short 44 nt HBV-derived substrate. The mutations are boxed in grey, and the $k_{obs}$ values (in min$^{-1}$) are indicated on the right. The stars indicate the SOFA-δRz-303 mutants for which the $k_{cat}$ and $K_M$ values were determined for the cleavage of a long version of the HBV-derived substrate (1190 nt);

FIG. 13C illustrates the relative percentage of cleavage as a function of spacer length. The bracket indicates the optimal length (1 to 5 nt), and dashed 0.5 lines separate the observed transitions;

FIG. 13D illustrates the histogram of the relative percentage of cleavage of the substrates possessing spacers of various lengths (5, 19, 33 and 47 nt). The inset shows the autoradiogram of the corresponding 10% denaturing PAGE gel;

FIG. 15A illustrates a schematic representation of the SOFA-ribozyme in both the off and on conformations, where the on conformation is obtained after the addition of the substrate. The bold lines indicate the oligodeoxynucleotides.

FIG. 16A illustrates the expression vector of the HBV-derived gene C used in the in vivo cleavage assays of the HBV-derived substrate by SOFA-δRz-303;

FIG. 16B illustrates the expression vector for various ribozyme versions in accordance with various embodiments of the present invention, used in the in vivo cleavage assays of the HBV-derived substrate by SOFA-δRz-303;

FIG. 16C illustrates autoradiograms of a Northern blot hybridization performed after a denaturing 1.3% agarose gel where β-actin and HBV mRNAs were detected using $^{32}$P-labelled RNA probes;

FIG. 18B illustrates autoradiograms of 6% denaturing PAGE gel of the cleavage assays;

FIG. 19A to 19F illustrate the sequence and secondary structure of various SOFA-ribozymes and SOFA-DNazyme in accordance with one embodiment of the Invention, showing both off and on conformations, wherein the small arrows of the on conformations indicate the cleavage or ligation sites;

FIG. 20 illustrates an autoradiogram of 6% denaturing PAGE gel of the cleavage assays obtained for the SOFA-DNazyme; and FIGS. 21A to 21C illustrate the sequence of a SiRNA (FIG. 21A), the sequence and secondary structure of a SOFA-siRNA version in accordance with a further embodiment of the invention, showing both off (FIG. 21B) and on (FIG. 21C) conformations, wherein the small arrows of the on conformation indicate potential cleavage sites.

DETAILED DESCRIPTION OF THE INVENTION

Figure 1:
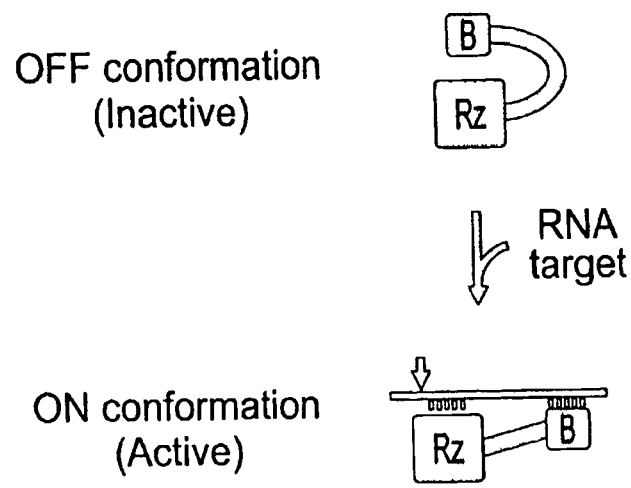
FIG. 1 is a schematic representation of both the off and on conformations of the SOFA-ribozyme of the present invention.

With the aim of generating highly specific ribozymes that could be regulated by the presence/absence of their target substrates, the inventors started with the concept that a ribozyme should be linked to a target-dependent module that acts as a biosensor (FIG. 1). In absence of its target, the ribozyme is inactive (off), while in the presence of the desired target the biosensor recognizes it and activates (turns on) the ribozyme's cleavage activity. Accordingly, a rational design led to a ribozyme controlled by a novel Specific On/off Adapter (SOFA). The original hepatitis delta virus (HDV) ribozyme, for which substrate recognition is based solely on the formation of seven base pairs in the P1 stem, was used as a suitable model (Bergeron, L. J., et al., Current Med. Chem. 10, 2589-2597, 2003).

In one embodiment of the invention, the SOFA (Box 8 on FIGS. 2A and 2B) includes three domains, also called sequences or segments:

a blocker (Sequence from ribonucleotide 30 to 33 of SEQ ID NO:1 on FIGS. 2A and 2B; Box 10, a biosensor (BS; Sequence from ribonucleotide 15 to 29 of SEQ ID NO:1 on FIGS. 2A and 2B; Box 12) and a stabilizer (Sequence from ribonucleotide 4 to 11 of SEQ ID NO:1 pairing with ribonucleotides 103 to 93 of SEQ ID NO:1, respectively, FIGS. 2A and 2B; Box 14).

In the absence of the target (Box 16 on SEQ ID NO:2, FIGS. 2A and 2B), the blocker 10 forms an intramolecular stem with the P1 strand (Sequence from ribonucleotide 55 to 61 of FIGS. 2A and 2B; Box 18), thereby generating an inactive conformation. Upon the addition of an adequate target, the biosensor anneals with the substrate, thereby releasing the P1 strand so that it can subsequently hybridize with the substrate, initiating formation of the active conformation. Thus, the target has two roles acting simultaneously, one as an activator and one as a substrate. The biosensor acts as a riboswitch regulating the catalytic activity. Finally, the stabilizer localizes the 3'-end of the SOFA module in a double-stranded region that stabilizes the ribozyme from the cellular nucleases (Lévesque, D., et al., *RNA* 8, 464-477, 2002).

To achieve the aim of the present invention, the inventors developed a switch, also referred to herein as a Specific On/Off Adapter or SOFA to improve specificity of a nucleic acid sequence such as DNA or RNA for its target and/or control the activity of said nucleic acid sequence. This construct can be made specific to particular ribozymes or RNA with enzymatic or effector activity, to activate or inactivate ribozymes or RNA simply by changing and matching the sequence of the biosensor with the complement of that of the target sequence, so that pairing up between the two can occur, when in presence of each other.

The biosensor must bind its complementary sequence on the substrate in order to unlock the SOFA module, thereby permitting the folding of the catalytic core into the on conformation. Both the blocker and the biosensor have been shown to increase the substrate specificity of the ribozyme's cleavage by several orders of magnitude as compared to the wild-type δRz. This is due mainly to the addition of the biosensor domain that increases the binding strength of the δRz to its target, but is also due to the fact that the blocker domain interacts with the P1 region and decreases its binding capacity. Finally, the presence of the stabilizer, which has no effect on the cleavage activity, stabilizes the RNA molecule in vivo against ribonucleases. The purpose of the stabilizer sequence is to pair up the 3' end of the sequence to prevent degradation. Both proof-of-concept and the preliminary characterization of SOFA-δRz that cleaves RNA transcripts derived from the hepatitis B and C viruses are reported here.

Methods

HBV, HCV and Ribozyme DNA Constructs

An HBV pregenome insert (from pCHT-9/3091, Nassal, M. *J. Virol.* 66, 4107-4116, 1992) was subcloned downstream of the T7 RNA promoter in the vector pBlueScript SK™ (Stratagene) using the SalI and SacI restriction sites, and the resulting plasmid named pHBVT7 (Bergeron, L. J., & Perreault, J. P. *Nucleic Acids Res.* 30, 4682-4691, 2002). An HBV 1190 nt fragment was excised from pCHT9/3091 using SacI and EcoRI, and then subcloned into pBlueScript SK™, generating pHBV-1190. A shorter HBV 44 nt substrate was produced using a PCR-based strategy with T7 sense primer: 5'-TTAATACGAC TCACTATAGG G-3' (SEQ ID NO:3) and antisense primer: 5'-CTTCCAAAAG TGAGACAAGA AATGTGAAAC CACAAGAGTT GCCCTATAGT GAGTCGTATT AA-3' (SEQ ID NO:4). The plasmid pHCVA was obtained by cloning the 1348 nt HCV 5' sequence from pHCV-1b (Alaoui-Ismaili, et al., Antiviral Res. 46, 181-193, 2000) into Hind III and BamHI pre-digested pcDNA3 vector. The original 8 ribozymes were constructed as described previously (Bergeron, L. J., & Perreault, J. P. *Nucleic Acids Res.* 30, 4682-4691, 2002). SOFA$^{+/-}$ ribozymes were constructed using a PCR-based strategy including two complementary and overlapping oligonucleotides. Briefly, two DNA oligonucleotides were used: i) the antisense oligonucleotide (Rz-down; 5'-CCAGCTAGAA AGGGTCCCTT AGCCATCCGC GAACGGATGC CCANNNNNNA CCGCGAGGAG GTG-GACCCTG NNNN-3' (SEQ ID NO:5), where N is A, C, G or T; $N_{44-49}$ is the sequence of the P1 stem and $N_{71-74}$ is the sequence of the blocker as illustrated in a preferred embodiment as set forth in on SEQ ID NO:1); and, ii) the sense primer (T7-5'Rz-up; 5'-TTAATACGAC TCACTATAGG GCCAGCTAGT TT(N)$_{72-20-BS(N)4-BL}$CAGGGTCCAC C-3'; SEQ ID NO:6) that permitted the incorporation of the T7 RNA promoter, and where (N)$_{7-20-BA}$ represents the biosensor (BS) sequence of 7 to 20 ribonucleotides in length and where (N)$_{4-BL}$ represents the blocker sequence (BL) of 4 ribonucleotides in length. The same strategy using two oligodeoxynucleotides was used to build the different versions of the ribozyme (i.e. the variants in the Biosensor (FIGS. 10 and 11); the Blocker (FIG. 12); the Stabilizer (FIG. 14); and, the SOFA-δRz-DN- and SOFA-δRz-DB ribozymes (FIG. 17)). All sequence variants are depicted in the corresponding figure. The amplification method has been described previously (Bergeron, L. J., & Perreault, J. P. *Nucleic Acids Res.* 30, 4682-4691, 2002). The PCR products were purified by phenol:chloroform extraction, precipitated with ethanol and dissolved in water. In vitro transcriptions and purifications of the ribozymes were then performed as described below. A similar strategy was used to build the different versions of 6 ribozyme.

The same strategy was used to construct substrates a to h of FIG. 10. Table 1 describes the sequences of the antisense primer.

TABLE 1

Oligodeoxynucleotide sequences of the a to h substrates a  5'-AAAGT<u>GAGACAAGAA</u>ATGTGAAACCAC/AAGAG
   CCCTATAGTGAGTCGTATTAA-3'
   (SEQ ID NO.:7)

b  5'-AAAGT<u>AGACTGAGATA</u>TGTGAAACCAC/AAGAG
   TGTACTCCCTATAGTGAGTCGTATTAA-3'
   (SEQ ID NO:8)

c  5'-AAAGT<u>GTTCAGCAC</u>TATGTGAAACCAC/AAGAG
   TGTACTGTCCCTATAGTGAGTCGTATTAA-3'
   (SEQ ID NO:9)

d  5'-AAAGT<u>AGGATACGGG</u>ATGTGAAAGCAC/AAGAG
   TGTACTGTAACCCTATAGTGAGTCGTATTAA-3'
   (SEQ ID NO:10)

e  5'-AAAGT<u>AGTCTGGATC</u>ATGTGAAACCAC/AAGAG
   TGTACTGTAACTCCCTATAGTGAGTCGTATTAA-3'
   (SEQ ID NO:11)

f  5'-AAAGT<u>GGCATAATCA</u>ATGTGAAACCAC/AAGAG
   TGTACTGTAACTTCCCCTATAGTGAGTCGTATTAA-3'
   (SEQ ID NO:12)

g  5'-AAAGT<u>AAGTTGGCGA</u>ATGTGAAACCAC/AAGAG
   TGTACTGTAACTTCAACCCTATAGTGAGTCGTATTAA-3'
   (SEQ ID NO:13)

h  5'-AAAGT<u>GTACTCATGC</u>ATGTGAAACCAC/AAGAG
   TGTACTGTAACTTCAATGCCCTATAGTGAGTCGTATTAA-3'
   (SEQ ID NO:14)

(/) indicates the P1 cleavage site.
The biosensor binding sequence is underlined.

For the substrates with seven different spacer lengths, the antisense primers were: 5'-AAAGTGAGACAAGAA-(A)$_{0-6nt}$-(AAACCAC)$_7$AAAAAACCC TATAGTGAGTCGTATTAA-3' (SEQ ID NO:15), where the T7 promoter sequence is underlined.

For the substrates with the spacers of different lengths; but possessing a unique cleavage site, the antisense primers were: 5'-AAAGTGAGACAAGAA(AAAAC)$_{SP}$-(ACCAACA)$_X$ (AAACCAC)$_Y$(ACCCAACA)$_Z$-AAAAAACCC TATAGTGAGTCGTATTAAAA-3'(SEQ ID NO:16) (where SP is for spacer, the number of X and Z units varied as desired; the unit Y gives the cleavable P1 sequence; and, the T7 promoter sequence is underlined). In these cases, the spacer was always 5'-AAAAC-3', except for the substrate of 5 nt that included the sequence 5'-AAAAA-3'.

For the in vivo experiments, the open reading frame of the HBV C gene was amplified from pCH9T/3091 (Nassal, M. J. Virol. 66, 4107-4116, 1992) using forward primer (5'-TATCTAAAGC TAGCTTCATG TCCTACTGTT CAAGC-CTCC-3', SEQ ID NO:17) and reverse primer (5'-TAGT-GAAACT CGAGAATAAA GCCCAGTAAA GTTCCCA-3', SEQ ID NO:18). The DNA product was cloned in the multiple cloning site of the pIND™ vector (Invitrogen) at the Nhe1 and Xho1 restriction sites. The strategy for the design of the vector expressing the ribozymes included several steps: 1) Firstly, the vector pcDNA3™ (Invitrogen) was digested at the Hind III and Xho I sites removing a portion of the multiple cloning sites region; 2) Secondly, a cassette was synthesized using two overlapping oligodeoxynucleotides (5'-AGCTTG-GTAC CGAGTCCGGA TATCAATAAA ATGC-3', SEQ ID NO:19 and 5'-TCGAGCATTT TATTGATATC CGGACTCGGT ACCA-3', SEQ ID NO:20 allowing introduction of Knp I and EcoR V restriction sites followed by a poly(A) signal sequence. These modifications of the vector permitted the production of ribozymes with a 3'-end poly(A) tail allowing their localization in the cytoplasm. This modified pcDNA3™ version was named pmδRz for "plasmid messenger δ ribozyme". 3) Thirdly, the product of amplification for the synthesis of ribozymes described above, was used to perform a new PCR amplification using as forward primer 5'-ATCCATCGGG TACCGGGCCA GTTAGTTT-3' (SEQ ID NO:21), and reverse primer 5'-CCAGCTAGAA AGGGTCCCTT AGCCATCCGC G-3' (SEQ ID NO:22). This nested PCR allowed removal of the T7 RNA promoter sequence and introduction of a 5'-end Knp I site and a 3'-end blunt sequence; 4) The resulting PCR products have been cloned in the Kpn I and EcoR V linearized pcDNA3™ modified version (i.e. prepared in step 1 and 2). All sequences were confirmed by DNA sequencing.

RNA Synthesis

Both ribozymes and RNA substrates were synthesized by run-off transcription from PCR products, HindIII linearized plasmid pHBV-1190 and XbaI linearized plasmid pHCVA templates. Run-off transcriptions were performed in the presence of purified T7 RNA polymerase (10 μg), RNAguard™ (32 units, Amersham Biosciences), pyrophosphatase (0.01 units, Roche Diagnostics) and linearized plasmid DNA in a buffer containing 80 mM HEPES-KOH, pH 7.5, 24 mM $MgCl_2$, 2 mM spermidine, 40 mM DTT, 5 mM of each NTP and with or without 50 μCi [$\alpha$-$^{32}$P]UTP (New England Nuclear) in a final volume of 100 μL at 37° C. for 3 hrs. Upon completion, the reaction mixtures were treated with DNase RQ1™ (Amersham Biosciences) at 37° C. for 20 min, purified by phenol:chloroform extraction, and precipitated with ethanol. The viral RNA products and ribozymes were fractionated by denaturing 5% and 8%, respectively, polyacrylamide gel electrophoresis (PAGE; 19:1 ratio of acrylamide to bisacrylamide) in buffer containing 45 mM Tris borate, pH 7.5, 7 M urea and 1 mM EDTA. The reaction products were visualized by either UV shadowing or autoradiography. The bands corresponding to the correct sizes of the ribozymes and the viral RNAs were cut out and eluted overnight at room temperature in a solution containing 0.5 M ammonium acetate and 0.1% SDS. The transcripts were desalted on Sephadex G-25™ (Amersham Biosciences) spun-columns, and were then precipitated, dissolved and quantified either by absorbance at 260 nm or $^{32}$P scintillation counting.

Labelling of RNA Substrates

First, RNA substrate (20 pmoles) was dephosphorylated using 0.2 units of calf intestinal alkaline phosphatase according to the manufacturer's recommendations (Roche Diagnostics). The reactions were purified by extracting with phenol: chloroform and precipitated with ethanol. Subsequently, the RNAs (10 pmoles) were 5'-end labelled in a mixture containing 10 μCi [$\gamma$-$^{32}$P] ATP (3000 mCi/mmol; New England Nuclear) and 12 units of T4 polynucleotide kinase following the manufacturer's protocol (United States Biochemicals). The end-labelled RNAs were purified using denaturing PAGE, and the relevant bands excised from the gel, then eluted, precipitated, and dissolved in water.

Ribozyme Cleavage Assays

Except when indicated, all reactions were performed under single turnover conditions ([Rz]>[S], where [Rz] is the ribozyme concentration and [S] is the substrate concentration) using 1 μM ribozyme and trace amounts of either internally $^{32}$P-labelled or $^{32}$P 5'-end labelled 1190 nt HBV, 1422 nt HCV or shorter RNA substrates at 37° C. in a final volume of 10 μL containing 50 mM Tris-HCl (pH 7.5) and 10 mM $MgCl_2$. For the multiple turnover reactions, the assays were performed at 50° C. with an excess of substrate over the ribozyme (15 μM vs 1 μM, respectively). After 3 hrs of incubation, the reactions were stopped by adding the loading buffer (5 μL of 97% formamide, 10 mM EDTA, pH 8.0), loaded on a 6% Polyacrylamide gel and analyzed with a radioanalytic scanner (PhosphorImager™, Molecular Dynamics). For the time course experiments, aliquots (0.8 μL) were removed at various times, up to 3 hrs, and were quenched by the addition of 5 μL of ice-cold formamide dye buffer. Cleavage reactions for the mechanism analysis were carried out either with or without 5 μM of a facilitator (FCO, 5'-AAAGTGAGAC AAGAA-3', SEQ ID NO:23), biosensor stem (BSO, 5'-TTCTTGTCTC ACTTT-3', SEQ ID NO:24) and an unrelated (UNO, 5'-CCCAATACCA CATCA-3', SEQ ID NO:25) oligodeoxynucleotide. Cleavage assays with the pools of mixed substrates were performed with trace amounts of radiolabelled substrates (50 000 cpm), non-labelled RNA substrate (2 μM) and SOFA-ribozymes (500 nM), except for the original ribozyme (WT, 2 μM). The reactions were incubated for 2 hours, analyzed on denaturing 10% Polyacrylamide gels, and revealed by PhosphorImager™.

RNase H Hydrolysis of SOFA-δRz-303

Trace amounts of 5' end labelled SOFA-δRz-303 (~10 000 c.p.m; <0.1 pmol) in the presence of 50 pmol of either the unlabeled small substrate (44 nt) or yeast tRNA as carrier (Roche Diagnostic) were preincubated in a volume of 8 μL containing 25 mM Tris-HCl pH 7.5, 25 mM KCl, 12 mM $MgCl_2$, 0.13 mM EDTA and 0.13 mM DTT at 25° C. for 10 min. Then, oligodeoxynucleotides (L3': 5'-GCGAGGA-3'; P4': 5'-CCATCCG-3'; BS': 5'-TGTCTCA-3'; BL': 5'-TGAAACT-3' and ST': 5'-CAGCTAG-3') 7 nt in size (10 pmol; 1 μL) were separately added to the samples before pre-incubating for another 10 min. Finally, 2 units of *Escherichia coli* RNase H (Ambion; 1 μL) were added to the mixtures and the samples incubated at 37° C. for 10 min. The reactions were quenched by adding 5 μL of cooled stop solution (97% formamide, 0.025% xylene cyanol and 0.025% bromophenol blue), the samples fractionated on denaturing 8% PAGE gels and the gels analyzed with a radioanalytic scanner (Storm™).

Cell Culture and DNA Transfections

HEK 293 EcR cells (Human Embryonic Kidney) were grown in Dulbecco's modified Eagle's medium (DMEM™) (Sigma) supplemented with 10% fetal bovine serum (Wisent) and 0.4 mg/ml of zeocine (Invitrogen) at 37° C. in 5% $CO_2$. The cells were transfected using Lipofectamine™, as per the manufacturer's instructions (Invitrogen).

Northern Blot Hybridization

Total RNA from HEK 293 EcR was extracted with Tri-Reagent (Bioshop Canada Inc, Burlington, Ontario, Canada). Northern blot analyses of total RNA (10 µg) extracted from HEK 293 EcR cells, were performed as described previously (D'Anjou, F., et al., J. Biol. Chem. 279, 14232-14239, 2004). The probes were synthesized as followed. For the HBV gene C probe, aliquot of the PCR product obtained previously (see DNA construct section) was cloned in the Xba I and Xho I sites of the pBlueScript™ (SK) vector (Stratagene). The resulting Sac I linearized vector was transcribed in vitro using T7 RNA polymerase in the presence of [$\alpha$-$^{32}$P]UTP. The β-actin RNA probe was synthesized using the Strip-EZ™ RNA T7/T3 kit (Ambion) according to the manufacturer's conditions. All hybridizations were carried out for 16-18 h at 65° C. The membranes were exposed on PhosphorImager™ screen for 2-24 h. The densitometry analysis was carried out on ImageQuant™ software.

Results

The SOFA-ribozyme of the present invention was tested using two accessible sites of the hepatitis B virus (HBV) RNA that have been previously selected for ribozyme cleavage (δRz-303 and δRz-513)(Bergeron, L. J., & Perreault, J. P. *Nucleic Acids Res.* 30, 4682-4691, 2002). These ribozymes inefficiently cleaved an HBV-derived RNA of 1190 nucleotides (nt) (~15%; FIG. 3). Corresponding SOFA-ribozymes (SOFA$^+$) possessing a biosensor that basepairs five nucleotides downstream of the P1 stem binding site demonstrate a drastically improved level of cleavage activity at both sites (~75%). Ribozymes bearing a biosensor domain unrelated to the target sequence remain locked in an inactive conformation (SOFA). The latter did not exhibit significant levels of cleavage activity even though the nucleotide sequence of the delta ribozyme portion is identical. This shows a greater "safety lock" capacity provided by the blocker domain, thereby diminishing the risk of non-specific cleavage. In FIG. 3, the length of the bands, in nucleotides, is shown adjacent to the gel. The control (−) was performed in the absence of ribozyme, while SOFA$^+$ and SOFA$^-$ indicates SOFA harbouring either the appropriate or inappropriate biosensor sequence, respectively.

Time course experiments reinforced the conclusion that appending a specific SOFA significantly contributes to enhancing the cleavage activity (FIG. 4). Moreover, similar conclusions were reached for several other SOFA-ribozyme constructions cleaving either HBV or hepatitis C virus (HCV) (see Table 2). Variation in the levels of cleavage activity might be due to several features, including the differences in binding efficiencies and the rate constants of the SOFA structural transitions (on/off conformations).

TABLE 2

Enzymatic activity of various SOFA-ribozyme constructions

| Target | Position | Open reading frame | % of cleavage WT | % of cleavage SOFA |
|---|---|---|---|---|
| HBV | 167 | C gene | 3.6 | 4.0 |
| | 279 | C gene | 18.5 | 57.9 |
| | 303 | C gene | 26.1 | 71.6 |
| | 398 | C gene | — | 79.0 |
| | 513 | C and P gene | 16.0 | 54.7 |
| | 993 | S and P gene | — | 57.4 |
| HCV | 224 | IRES | 1.3 | 13.4 |
| | 302 | IRES | 3.3 | 29.4 |

Cleavage activity was investigated using SOFA$^+$-Rz-303 possessing biosensor sequences of various lengths. Under single turnover conditions, the cleavage levels increased in proportion to the size of the biosensor (FIG. 5). The longer the base-paired segment (BS-7<BS-10<BS-12<BS-15<BS-20), the better the binding of the ribozyme to the substrate and the higher level of cleavage activity. Kinetic analyses permitted the determination of second order rate constants ($k_{cat}/K_M$) where it was observed that those for the SOFA$^+$-ribozymes were up to an order of magnitude higher than that of the original ribozyme (WT). Under multiple turnover conditions, a smaller HBV-derived substrate was used since the length of the latter affects the turnover rate of the ribozyme. In this case, the level of cleavage increases in proportion to the length of the biosensor, up to 10 nucleotides, at which point it decreased with increasing length (FIG. 6). Elongation of the biosensor stimulates the cleavage activity up to the point where product release becomes rate limiting. Astonishingly, in this specific experiment the SOFA$^+$-δRz-303-BS-10 performed four turnovers, while the original ribozyme only completed one. More importantly, the SOFA-ribozyme meets the classical criteria of an enzyme (e.g. it exhibits turnovers). Since no independent effector is required, this is not an allosteric enzyme. In FIG. 6, the XC indicates the position of the xylene cyanol. The length of the bands in nucleotides is shown adjacent to the gel. The control (−) was performed in the absence of ribozyme.

Figure 7A:
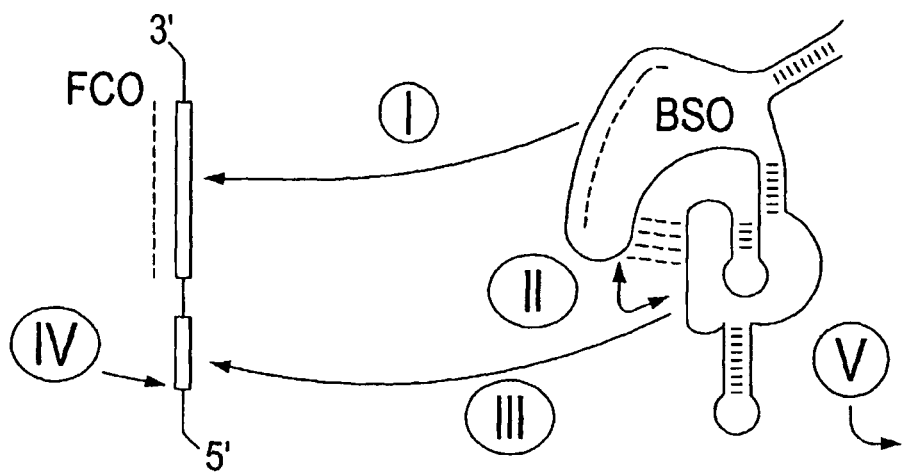
FIGS. 7A and 7B illustrate an analysis of the mechanism of action of the SOFA-ribozyme, showing the proposed sequential interactions between the ribozyme and the substrate (FIG. 7A), and the relative cleavage efficiencies calculated from two independent sets of experiments using the original—(WT), SOFA$^+$- and SOFA$^-$-δRz-363 ribozymes incubated either with or without the FCO, BSO and unrelated (UNO) oligodeoxyribonucleotides (FIG. 7B)
Figure 7B:
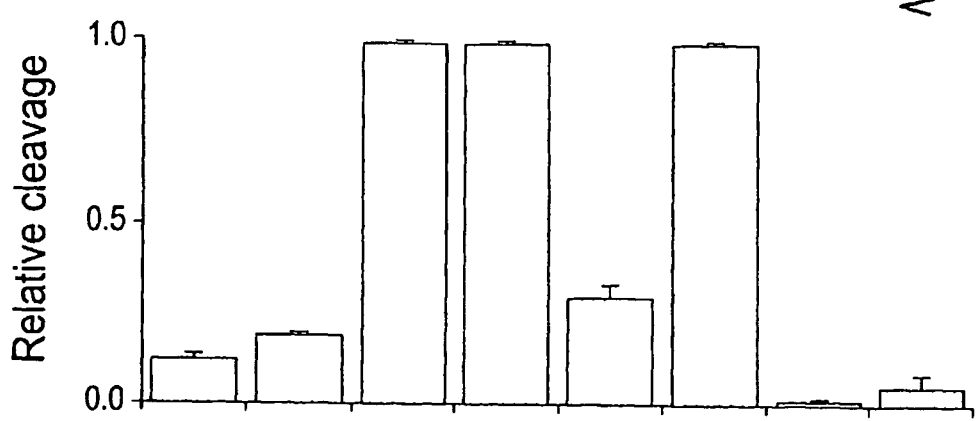

The mechanism of action of both the biosensor and blocker sequences was investigated using an oligodeoxyribonucleotide competition approach coupled with mutated ribozymes (FIGS. 7A and 7B). In FIG. 7A, the roman numerals identify the steps of the mechanism. Dashed lines identify oligodeoxyribonucleotide binding to either the substrate (i.e. FCO acting as facilitator) or the biosensor (BSO). The addition of an oligodeoxyribonucleotide with the same sequence as the biosensor domain (FCO) slightly increased the level of cleavage of the original δRz-303. This oligodeoxyribonucleotide acts as a facilitator that renders the binding site more accessible to the catalytic region of the ribozyme. In contrast, the presence of the FCO does not alter the level of cleavage of SOFA$^+$-δRz-303 after an incubation of 3 hours, although it takes more time to reach this cleavage level. One possible explanation is that the binding of both the biosensor and the P1 sequence favourably competes with the FCO for the substrate. When the experiment is repeated using an oligodeoxyribonucleotide complementary to the biosensor sequence (BSO), the cleavage activity of the SOFA$^+$-ribozyme is drastically decreased. Conversely, the presence of an oligodeoxyribonucleotide having an unrelated sequence (UNO) does not modify the cleavage level, indicating that the biosensor domain is the driving force in the process. Finally, the contribution of the blocker domain was assessed using SOFA$^-$-δRz-303. This off-version which lacks the adequate biosensor, but possesses the appropriate P1 stem, barely demonstrated a detectable level of cleavage. In contrast, a mutant lacking the blocker sequence exhibited a higher cleavage activity than did the SOFA-ribozyme. Hence, the blocker plays its role by preventing the formation of the P1 stem in the absence of the appropriate biosensor. This requirement increases the specificity of the SOFA because it can only be activated by the desired substrate.

Figure 8A:
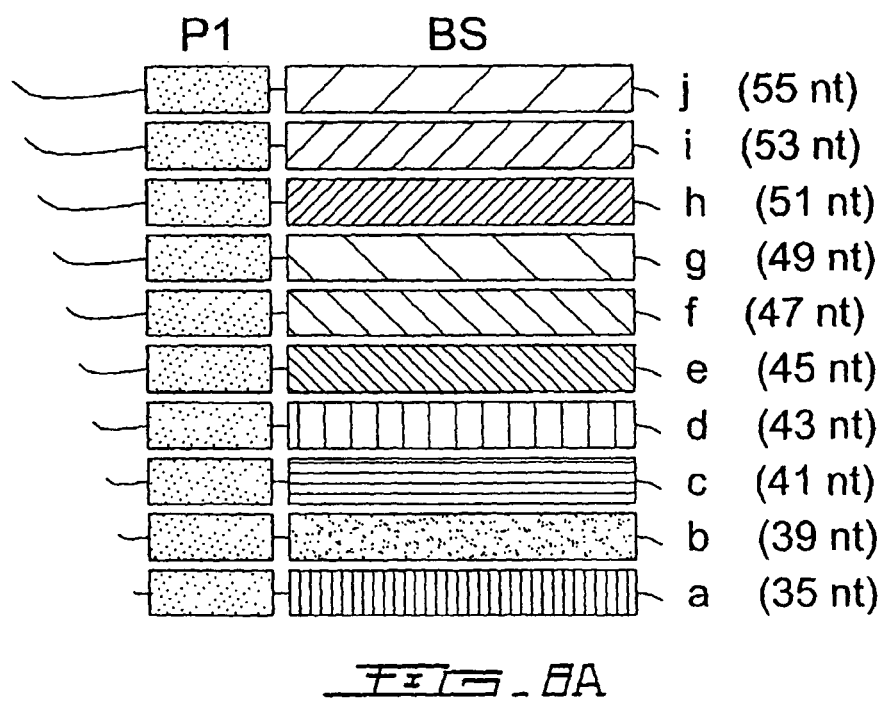

The specificity of a ribozyme can commonly be defined by the ability to discriminate between two or more similar RNA substrates. In order to illustrate the gain in terms of substrate specificity, two distinct experiments were performed. First, ten substrates were designed (see Table 3 below), each possessing an identical P1 binding sequence coupled to a distinct binding sequence for the biosensor. The substrates were successively extended at their 5' extremity by at least two nucleotides in order to provide them with assorted electrophoretic mobilities (FIG. 8A).

establish the high substrate specificity of the SOFA module of the present invention, in addition to illustrating its character as a facilitator (i.e. unwinding the neighbouring structure of the target site). The accessibility of target sites became a less

TABLE 3

Substrates
Substrates sequences

| Substrates (SEQ ID NO) | 5' | P1 | Spacer | BS | 3' |
|---|---|---|---|---|---|
| A (SEQ ID NO:26) | GGGCUCUU | GUGGUUU | CACAU | UUCUUGUCUC | ACUUU |
| B (SEQ ID NO:27) | GGGUACACUCUU | GUGGUUU | CACAU | CAGGCACCUC | ACUUU |
| C (SEQ ID NO:28) | GGGAGUACACUCUU | GUGGUUU | CACAU | AUCUCAGUCU | ACUUU |
| D (SEQ ID NO:29) | GGGACAGUACACUCUU | GUGGUUU | CACAU | AGUGCUGAAC | ACUUU |
| E (SEQ ID NO:30) | GGGUUACAGUACACUCUU | GUGGUUU | CACAU | CCCGUAUCCU | ACUUU |
| F (SEQ ID NO:31) | GGGAGUUACAGUAOACUCUU | GUGGUUU | CACAU | GAUCCAGACU | ACUUU |
| G (SEQ ID NO:32) | GGGGAAGUUACAGUACACUCUU | GUGGUUU | CACAU | UGAUUAUGCC | ACUUU |
| H (SEQ ID NO:33) | GGGUUGAAGUUACAGUACACUCUU | GUGGUUU | CACAU | UCGCCAACUU | ACUUU |
| I (SEQ ID NO:34) | GGGCAUUGAAGUUACAGUACACUCUU | GUGGUUU | CACAU | GCAUGAGUAC | ACUUU |
| J (SEQ ID NO:35) | GGGUGCAUUGAAGUUACAGUACACUCUU | GUGGUUU | CACAU | CUGUGCUGCA | ACUUU |

Figure 8B:
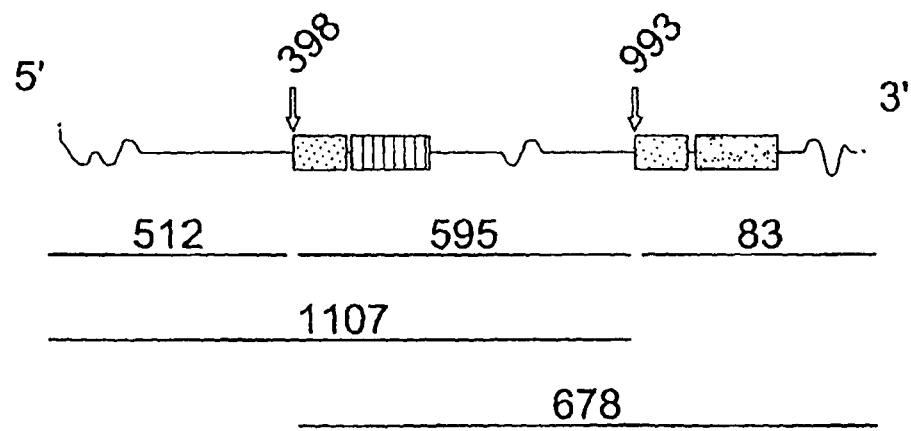
Figure 8D:
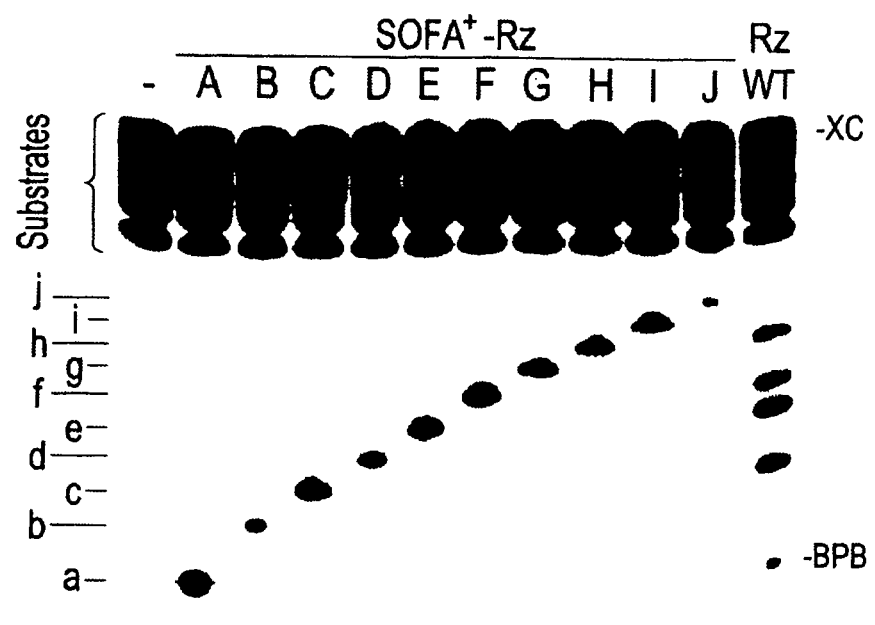
Figure 8E:
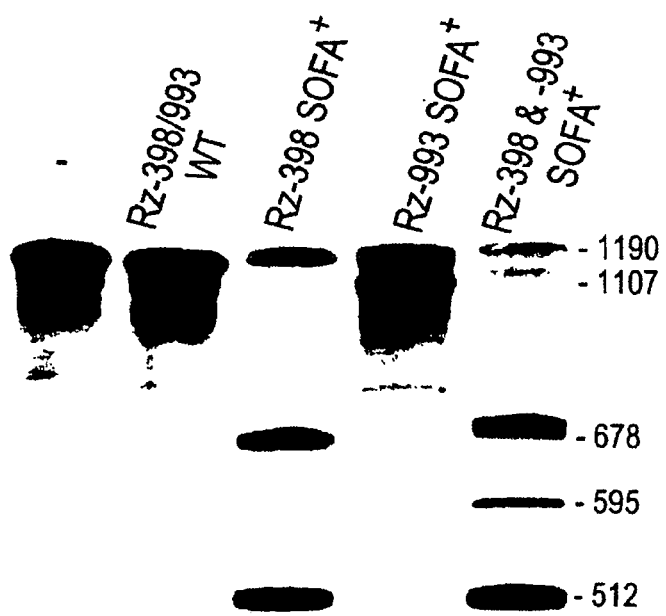
Figure 8F:
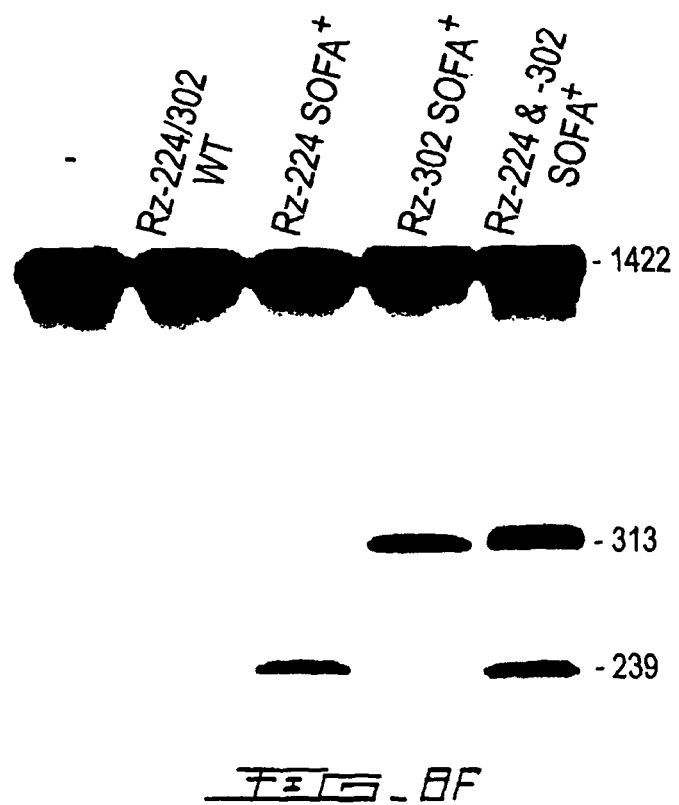

When all of the substrates were incubated together with a given SOFA⁺-ribozyme, only the substrate harbouring the relevant requirements, in term of sequence recognition by the biosensor of that ribozyme, was cleaved. Lower cleavage levels for the substrates B and J were indicative of the influence of the biosensor sequence identity. This experiment reveals that a ribozyme, activated by the proper substrate, did not cleave other substrates via a trans-cleavage mechanism. Conversely, the original ribozyme did not make this discrimination (lane WT) and all substrates were cleaved, although at different levels. In a second demonstration, the inventors attempted to selectively cleave sites of long RNA molecules that included an identical P1 binding sequence but different biosensor sequences. A sequence of 7 nt long was retrieved twice in the HBV fragment (i.e. cleavage at positions 398 and 993; FIGS. 8B and 8E), demonstrating the possibility of having multiple cleavage sites using the 7 nt requirement of a wild type ribozyme. In addition, the classical HDV ribozyme did not allow the detection of cleavage at either of these sites, most likely because they were embedded in complex structures. In contrast, SOFA-ribozymes exhibited an efficient and specific cleavage at these sites (i.e. without any interference between the sites). This corroborates the power of the SOFA module, and points out that it enables the cleavage of a substrate uncleavable by the original ribozyme. Similar results were acquired when targeting a repeated sequence (i.e. cleavage site at positions 224 and 302) within the highly structured Internal Ribosome Entry Site (IRES) of the hepatitis C virus of HCV; FIGS. 8C and 8F). Consequently, no cis-cleavage was observed in these studies. Clearly, these experiments important hurdle than it was for classical ribozymes (D'Anjou, F., et al., *J. Biol. Chem.*, 279, 14232-14239, 2004). In FIGS. 8A and 8D, there is reported cleavage assays of a pool of ten 5'-end-labelled substrates (a to j) by either specific SOFA-ribozymes (named A to J) or the original ribozyme (WT). All the ribozymes and substrates have a similar P1 stem sequence (P1), but differ in the biosensor sequences (BS). The length of each substrate is indicated in nucleotides. BPB and XC in FIG. 8D indicate the positions of bromophenol blue and xylene cyanol, respectively. The control (−) was performed in the absence of ribozyme. In FIGS. 8B and 8E, there are reported cleavage assays of the HBV-derived target by SOFA-ribozymes cleaving at either position 398 or 993. In FIGS. 8C and 8F, there are reported cleavage assays of a 1422-nt HCV-derived target by SOFA-ribozymes cleaving at either position 224 or 302 of the IRES. For FIGS. 8B, 8E, 8C and 8F, the sequence of the P1 stem is identical at each site, but the biosensor sequences are different.

Figure 9:
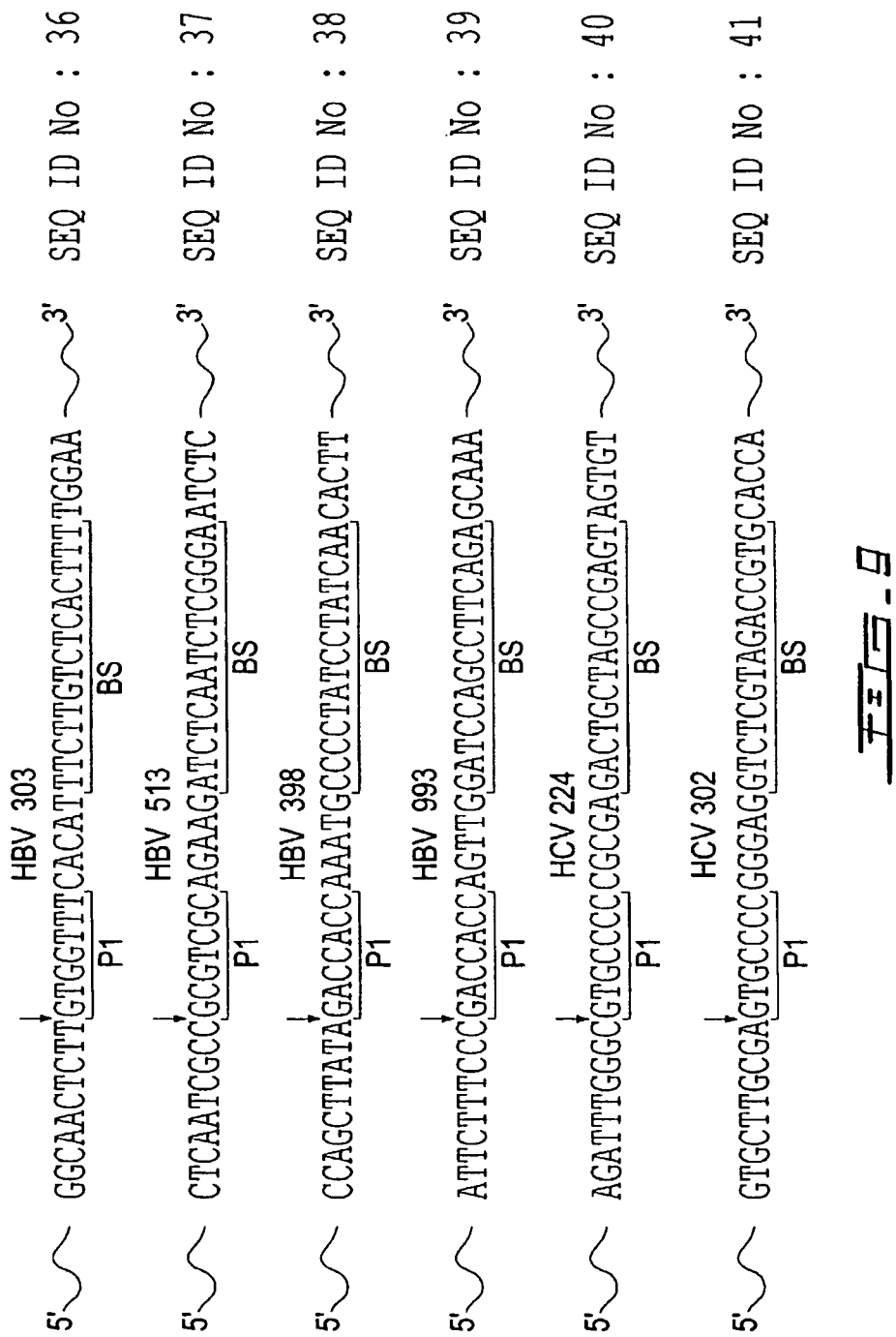
FIG. 9 illustrates the sequences of all the targeting sites used in FIGS. 1 to 8 except in FIGS. 8A and 8D.

The specific sequences of the various studied targeting sites derived from HBV and HCV viruses are illustrated in FIG. 9 (SEQ ID NO:36 to 41). The cleavage sites are indicated with arrows.

Specificity Conferred by the Biosensor Sequence

In order to gain more knowledge from the SOFA module, we were interested in establishing the substrate specificity for ribozyme cleavage conferred by the biosensor sequence. Several experiments described above revealed the crucial role that the biosensor sequence must play in order to insure great accuracy in terms of the substrate specificity for the ribozyme cleavage. More specifically, it has been shown that a ribozyme, when activated by the proper substrate, does not cleave other substrates by either the cis- or trans-cleavage mechanisms. For example, in one experiment a ribozyme was incubated in the presence of ten different small substrates possessing identical P1 binding sequences coupled to completely different biosensor binding sequences (FIGS. 8A and D). This experiment led to the conclusion that each of the ten ribozymes only cut efficiently when the biosensor perfectly bound to the target RNA. However, it did not permit investigation of how the biosensor sequence identity influenced the substrate specificity. In order to address this issue we performed two distinct experiments.

Figure 10B:
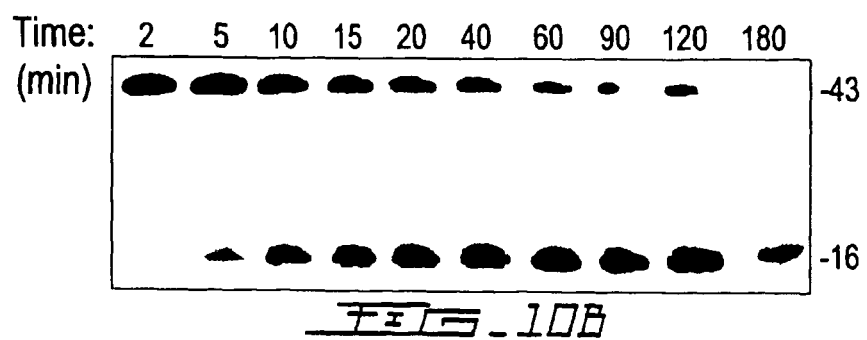
FIGS. 10B and 10C illustrate the autoradiogram of a typical 10% denaturing PAGE gel of a time course experiment performed under single turnover conditions for the pair Dd, and the graphical representation of the time course of ribozyme D cleaving each of the substrates (a to h)
Figure 10C:
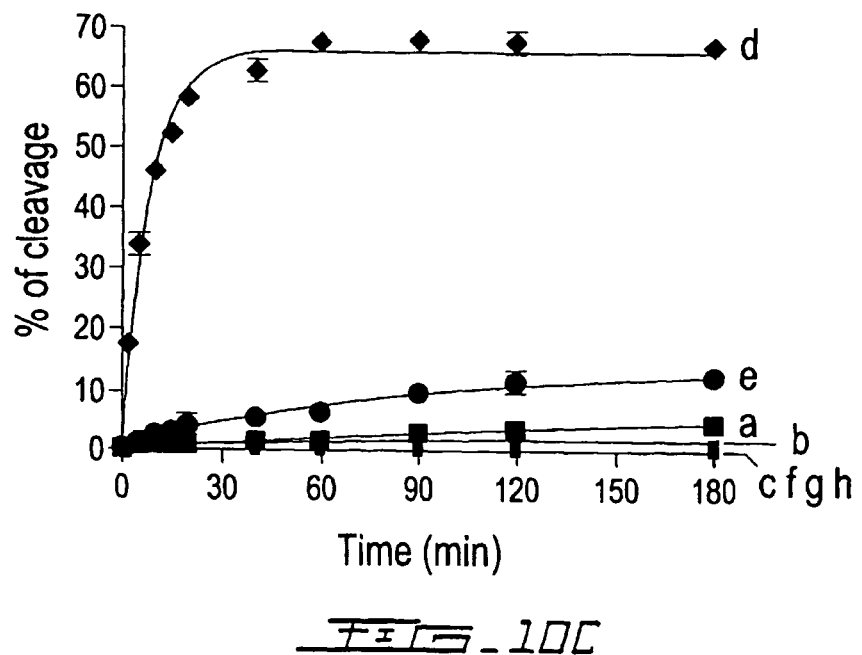
Figure 10D:
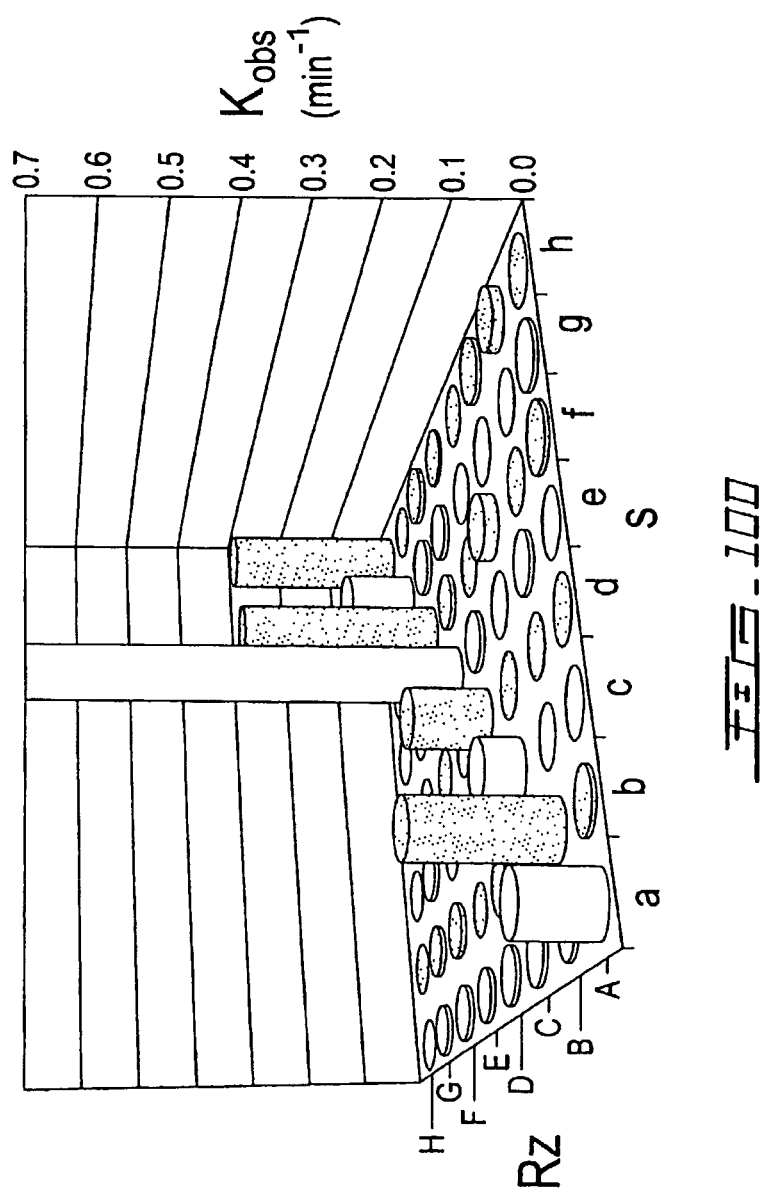
FIG. 10D illustrates the histogram of the $k_{obs}$ values for each of the 64 possible pairs.

Initially, the cleavage activities of the eight most active SOFA-ribozymes from the collection described above were determined for each substrate alone, rather than within a pool. Both the biosensor sequences of the ribozymes and the substrate sequences are shown in FIG. 10A (SEQ ID NO:42 to 57). The substrates were arbitrarily designated a to h, while a ribozyme perfectly complementary (i.e. one with the appropriate biosensor, SOFA$^+$) to a given substrate received the corresponding superscript letter, i.e. A to H (e.g. RzS=Aa). These experiments were performed under single turnover conditions ([Rz]>[S]). Aliquots were removed at different intervals, fractionated on denaturing 10% polyacrylamide gels (PAGE) and analyzed by radioanalytic scanning. A typical gel is shown in FIG. 10B and shows the kinetics for the couple Dd. The cleavage rate constant ($k_{obs}$) for at least two independent assays was estimated for each possible couple. The reaction time course for each substrate with ribozyme D is illustrated in FIG. 10C. Only the perfectly matched couple Dd exhibited an active cleavage. The $k_{obs}$ average values for each RzS couple tested (64 couples) are reported as a histogram (FIG. 10D). This large data set prompted several observations. First, only the eight couples that had a perfect match between the biosensor and substrate sequences (located on the diagonal) had high $k_{obs}$ values. These $k_{obs}$ values varied between 0.056 to 0.69 min$^{-1}$ (i.e. Cc and Ee, respectively). This difference of 12-fold in the $k_{obs}$ shows that the identity of the biosensor sequence significantly influenced the cleavage activity.

Secondly, most of the imperfect couples, in which the number of mismatches varied between two and eight (the GU wobble was considered as base pair (bp)), exhibited cleavage activities characterized by significantly lower $k_{obs}$. In several cases the $k_{obs}$ values for the cleavage of a mismatched substrate were three or more orders of magnitude smaller than that of their perfectly matched counterparts (e.g. Ac, Dg, and Hd). For example, ribozyme H cleaves substrate d with a rate constant 15 000 times smaller than it does substrate h. However, in most of the cases, the rate constants of imperfect couples were 25 to 250 fold lower. Thus, ribozyme F cleaved the imperfect substrates with $k_{obs}$ varying from 25 to 47 fold smaller than that of the perfect substrate, while ribozyme E cleaved them with $k_{obs}$ values ranging between 77 to 291 fold less than that of the perfect substrate (with the exception of the Ed couple that possessed a $k_{obs}$ 5010 times smaller than that of the ideal Ee pair). More generally, we observed that the catalytic parameters correlate directly with substrate specificity (i.e. the more active the ribozyme, the better its substrate specificity seemed to be). Additional ribozymes with a different biosensor sequence (i.e. one with more than three mutations) also led to the same conclusion; namely that they efficiently cleaved their desired substrate (that with the sequence complementary to the biosensor), but not other unrelated substrates. Together, these results demonstrate the potential of the biosensor to improve the substrate specificity of a ribozyme.

Figure 11B:
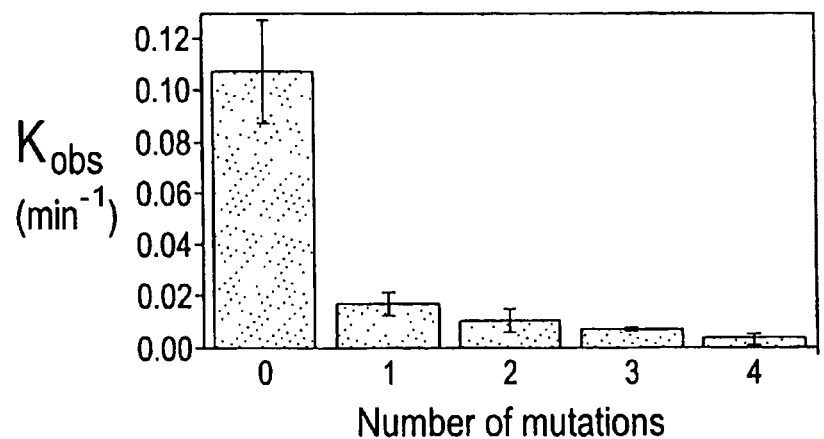
FIG. 11B illustrates the average values of $k_{obs}$ from at least two independent sets of experiments for each cluster of mutated ribozymes.

This first experiment confirms that a ribozyme cleaves its perfectly complementary substrate with a relatively high rate constant value, but that it is drastically less efficient for nonperfect couples (i.e. those including several mismatches). In order to obtain a more precise picture of the situation, a second experiment involving SOFA-δRz-303 sequence variants with less potential for forming mismatches was performed. Twenty-three mutated ribozymes including 1 to 4 randomly distributed substitutions within the biosensor sequences were synthesized (FIG. 11A, SEQ ID NO:58 to 81). A residue of the biosensor was substituted for by the same base found at the corresponding position within the substrate, thereby producing a mismatch. The cleavage activity of each mutated ribozyme was assessed, and the rate constant ($k_{obs}$) determined. The $k_{obs}$ are reported individually in panel A of FIG. 11, while panel B illustrates the variation of the $k_{obs}$ average as a function of the number of mutations. Clearly, the decrease in the cleavage activity is directly related to the number of mutations (FIG. 11B). While the presence of a single mismatch reduced the $k_{obs}$ values from 4 to 15 fold, the presence of 4 mutations yielded $k_{obs}$ values 18 to 106 fold smaller. The position of the mutation within the biosensor appeared to have only a small effect on the cleavage observed. However, a single mutation in the middle of the biosensor stem reduced the cleavage activity slightly more than one located near the ends (see FIG. 11A). This is probably due to the fact that a mismatch in the middle of the stem may interrupt the stacking. According to these data, the presence of only one mutation in the biosensor appears to be sufficient to significantly affect the cleavage activity. Two different mutants were produced for the positions 2, 6, 9 and 6-9, and the decrease in the cleavage activity was found to be similar regardless of the nature of the mutation (see FIG. 11A). In addition, we also observed that the influence of a mutation in the biosensor was more important when targeting a long HBV-derived transcript. This suggests that SOFA-δRz efficiently discriminate their substrate. The second order rate constants ($k_{cat}/K_M$) of both the single and double mutants, SOFA-δRz-303(A6U) and (A6U)(A9U), were shown to be 25-fold lower than that of the original version (stars in FIG. 11A; see above). Determination of the kinetic parameters of other single or double mutants also led to the same conclusion (i.e. the $k_{cat}/K_M$ values of the mutants are at least one order of magnitude lower than that of the original SOFA-δRz-303, stars in FIG. 11A). These differences were also due to a lower $k_{cat}$ and a higher $K_M$, in agreement with the idea that fewer base pairs are involved in the recognition between the ribozyme and the substrate.

Characterization of the Blocker Sequence

Figure 12A:
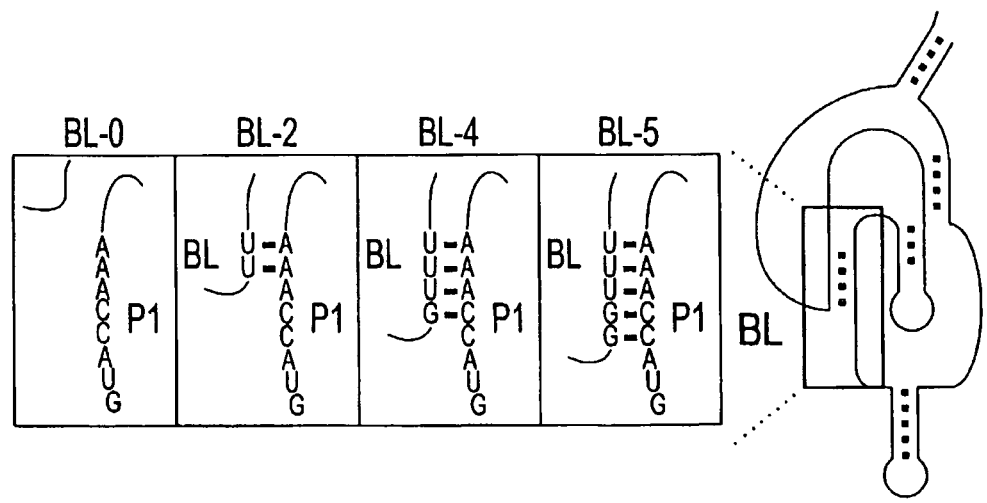
FIG. 12A illustrates four blocker stems tested.
Figure 12B:
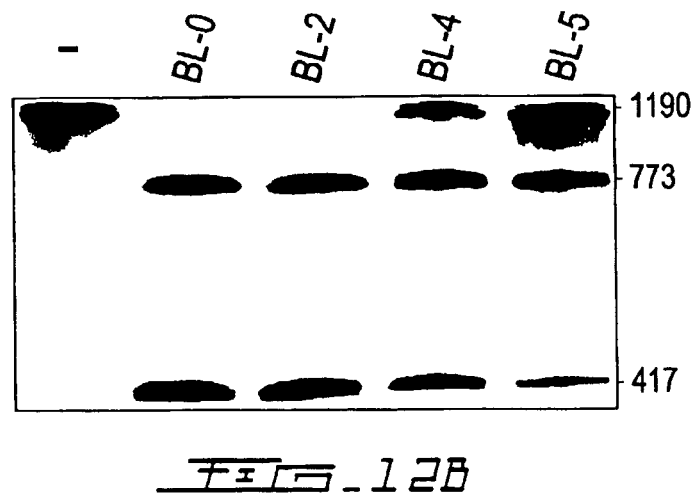
FIG. 12B illustrates an autoradiogram of a 6% denaturing PAGE of the cleavage assays performed with the SOFA-δRz-303 variants possessing mutated blocker sequences (i.e. BL-X, where X indicates the size of the blocker stem). The reactions were performed under single turnover conditions using the 1190-HBV substrate. The sizes of the bands are indicated on the right of the gel. The control (−) was performed in the absence of ribozyme.
Figure 12C:
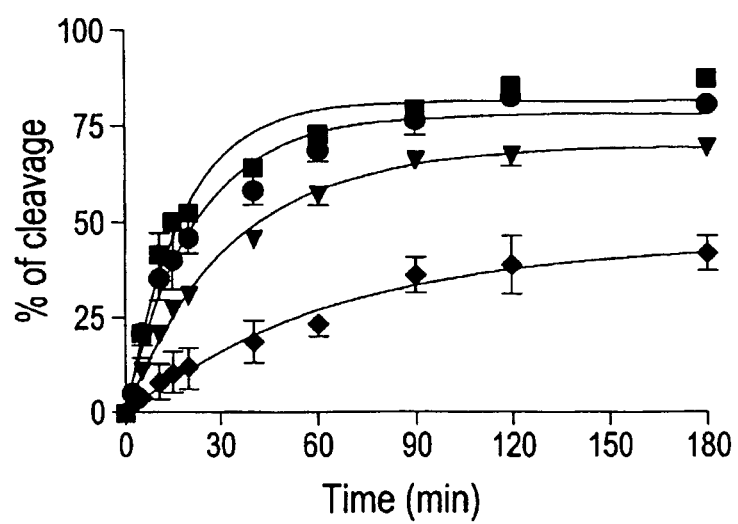
FIG. 12C illustrates a kinetic analysis performed for each of the mutants: BL-0, squares; BL-2, circles; BL-4, inverse triangles; and, BL-5, diamonds.

In the absence of the appropriate target RNA substrate, the SOFA-ribozyme adopts an inactive conformation, the off conformation. According to the SOFA design, this state is due to the 4 nucleotides blocker sequence binding the P1 region of the ribozyme, thereby preventing the binding of non-specific substrates (see FIG. 2). Consequently, the longer the blocker sequence, the better the "safety lock" effect. In order to verify this hypothesis, and to establish the importance of the blocker sequence for the "safety lock" concept, several SOFA-ribozymes with mutated blocker sequences were synthesized and their cleavage activities assessed by targeting the HBV-derived transcripts of 1190 nucleotides. Since no mutation was required within the substrate, the longer transcript appeared to be more suitable for characterization because it is more relevant to a natural target. Different blocker lengths (0 to 5 nucleotides) were used in order to find the largest stem that did not inhibit cleavage of the appropriate substrate (FIG. 12A). A typical autoradiogram of a PAGE gel is illustrated in FIG. 12B. In the absence of the blocker sequence, SOFA-δRz-303 was very active (i.e. BL-0, 81% cleavage). The same level of cleavage was detected in the presence of a 2 nucleotides blocker sequence (i.e. BL-2, 79% cleavage), indicating that two bases were insufficient to allow the formation of a stable stem between the blocker and the ribozyme's P1 strand. A SOFA-ribozyme with a 4 nucleotides blocker sequence cleaved the substrate relatively efficiently, although at a reduced level as compared to the previous assay (i.e. BL-4 71%). Elongation of the blocker sequence by one more nucleotide significantly reduced the cleavage exhibited (i.e. BL-5 40% of cleavage). In this case, it seems that the ribozyme remained locked in the off conformation, indicating that formation of the intramolecular stem between the P1 region of the ribozyme and the blocker sequence seems to be favoured over hybridization between the ribozyme and the substrate. Thus, a blocker sequence of 4 nucleotides appears to be the optimal size to lock the ribozyme while still allowing it to unlock in the presence of the desired substrate. Time-course experiments of these four ribozymes confirmed that a blocker sequence of 4 nucleotides is suitable for establishing a balance between the off/on conformations, that is one that blocks, but not too much (FIG. 12C).

Blockers of 6 nucleotides or more were also tested. In addition to blocking too much of the ribozyme in its inactive conformation (i.e. almost irreversible), we also observed ribozymes that self-cleaved the sequence adjacent to the blocker sequence (i.e. within the biosensor), an unacceptable phenomena.

The sequence of the blocker segment might also modulate the level of inhibition. We observed that if a mutated blocker cannot form a stem with the P1 strand, then no inhibition is observed. In contrast, previous experiments have shown that SOFA⁻-δRzs with different target sites on HBV-derived transcripts were all inactive (see previously). These ribozymes possessed the appropriate P1 strands and complementary blocker sequences, while their biosensor sequences could not bind the substrates. The inactivity of these SOFA⁻-δRzs confirmed that the blocker sequence plays its role by inhibiting the catalytic activity in the absence of the appropriate biosensor sequence. In all cases, the SOFA⁺-δRzs possessing a biosensor sequence capable of binding the substrate efficiently cleaved their substrates.

Spacing Between the P1 Stem and the Biosensor Binding Domain

Figure 13A:
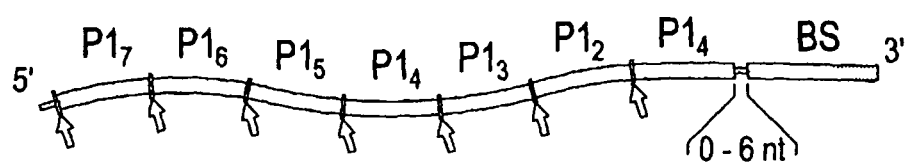
FIG. 13A illustrates the design of the substrates used to analyze the importance of the spacer sequence. The substrate P1 strand of SOFA-δRz-303 was repeated seven times (P1$_N$, 1-7) within seven substrates possessing spacers of different sizes (0 to 6 nt)
Figure 13B:
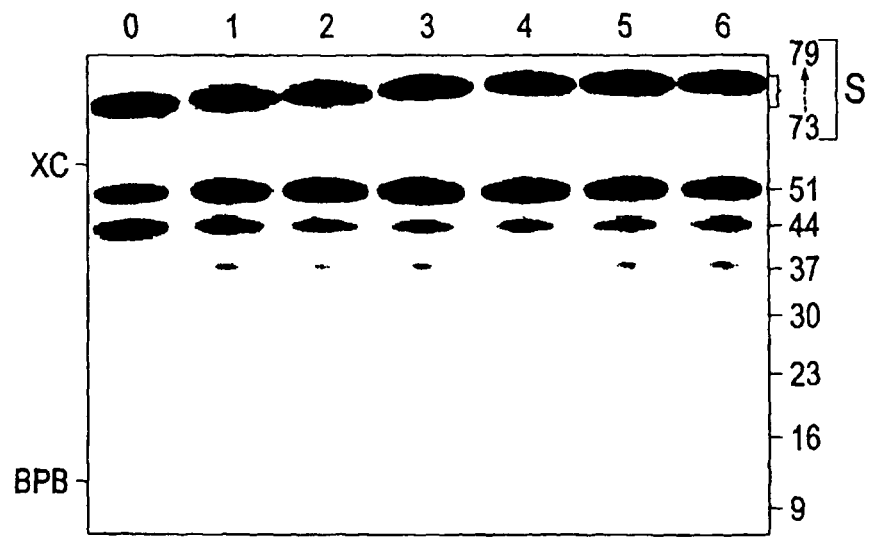
FIG. 13B illustrates an autoradiogram of a 10% denaturing PAGE of the cleavage assays performed with each of the seven substrates. Lanes 0 to 6 correspond to the different sizes of the spacer sequences (i.e. from 0 to 6 nt). The migrations of the substrates (S) and their sizes, as well as those of the cleavage products, are indicated adjacent to the gel. XC and BPB indicate xylene cyanol and bromophenol blue.

A SOFA-ribozyme recognizes its substrate through two independent domains. Initially, the biosensor sequence binds its complementary sequence on the substrate, and, subsequently, the P1 stem is formed between the ribozyme and the substrate. In all experiments reported so far, the two binding domains were separated by 5 nucleotides simply to avoid the chance that the proximity and stacking of the P1 and biosensor would affect the release of the product. However, there was no scientific rational supporting this spacing of 5 nucleotides. In order to investigate this parameter seven model substrates possessing seven head-to-tail repetitions of the P1 stem domain (P1N) followed by the SOFA-δRz-303 biosensor sequence were synthesized (see FIG. 13A). The substrates differed by possessing a distance of 0 to 6 nucleotides between the domain bound by the biosensor and the first adjacent P1 binding sequence. In this way we created the equivalent of 49 different substrates that included different spacer lengths. The ribozyme should bind its complementary sequence at the 3' end of the substrate via its biosensor, and should subsequently find a P1 sequence at an ideal distance. The cleavage experiments were performed during a short period of time (5 min) so as to permit only the unique cleavage reaction of 5' end labelled substrates to occur. The substrates used in this experiment exhibited different electrophoretic mobilities depending on their sizes, which differed by one nucleotide. The 5' radiolabelled products of all cleavages made with the same P1 sequence migrated similarly on the gel because the one base difference was located within the non-radioactive 3' product (FIG. 13B). We observed that all substrates were preferentially cleaved at the first or second sites near to the biosensor sequence (i.e. $P1_1$ and $P1_2$). With the exception of the substrate with no spacing between the P1 and biosensor domains, we observed that the higher level of cleavage occurred at the first P1 site ($P1_1$). In order to facilitate the interpretation of this data, we calculated the relative percentage of cleavage for all substrates. They are shown as a function of the spacer length (FIG. 13C). There is an increase in the percentage of cleavage as one progress from no spacer to an optimal length of 3 nucleotides. This is followed by a decrease up to a spacer of 21 nucleotides, at which point the relative percentages of cleavage remains constantly low regardless of the length of these sequences. The decrease occurs mainly stepwise for substrates cleaved at their $P1_2$, $P1_3$, and $P1_4$ sequences, with a preference for the substrates with the smaller spacers (see dashed lines, FIG. 13C). This experiment shows that it is preferable to have at least a one nucleotide space between the biosensor and the P1 region, and that the optimal length is found between 1 and 5 nucleotides. The need to have at least a minimal spacer was confirmed by observing that a completely different SOFA-δRz barely cleaved its substrate if there is no spacer between the substrate's P1 domain and the biosensor.

Figure 14A:
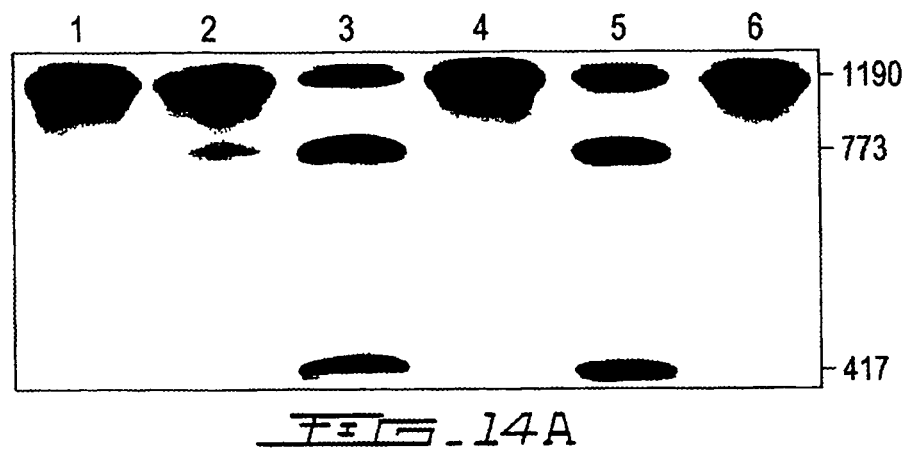
FIG. 14A illustrates an autoradiogram of a 6% denaturing PAGE of cleavage assays of various SOFA-δRz-303 variants synthesized to evaluate the importance of the stabilizer sequence, where lane 1 is the incubation of the long HBV-derived substrate (1190 nt) alone, while lane 2 is that in the presence of the original δRz-303, lanes 3 and 4 are the cleavage assays performed with SOFA$^+$- and SOFA$^-$-δRz-303 including the stabilizer stem, respectively, lanes 5 and 6 are the cleavage assays performed with the SOFA$^+$- and SOFA$^-$-δRz-303 lacking the stabilizer stem, respectively. The sizes of the bands are indicated adjacent to the gel.

We subsequently confirmed these results using different substrates that harbour spacers of different lengths and a single cleavage site, like the normal SOFA-δRz does. Four substrates were designed based on the initial results obtained with the seven consecutive P1 stem domains. Each of these substrates contained only one P1 sequence, located in position P1, $P1_3$, $P1_5$ or $P1_7$ (i.e. 5'-GUGGUUU-3'). The other sequences were replaced by another that cannot be bound by the P1 strand of the ribozyme (i.e. 5'-UGUUGGU-3'). In this way, the spacer sequences were extended to 5, 19, 33 and 47 nucleotides, respectively. All substrates were cleaved at different levels (see FIG. 13D, inset). The relative percentages of cleavage were used to analyze the effect of the spacer length. (FIG. 13D). We observed that the shorter a spacer is, the better the cleavage activity of the ribozyme. However, the difference between the shorter and longer spacers, in terms of cleavage activity, is not as significant as in the above experiment. In the present case, there is no competition between several sites, a condition that should enhance the level of catalytic activity regardless of the position of the cleavage site. These data confirmed that a minimal spacer (1 to 5 nucleotides) is better for efficient activity with SOFA-δRz. The sequence of the stabilizer stem does not influence the ribozyme cleavage The stabilizer brings both the 5' and 3' ends into a common terminal stem. This domain has been included in the SOFA module due to previous observations revealing that the terminal P2 stem of the original δRz provides tremendous stability to this RNA species (Levesque et al., *RNA* 8, 464-477, 2002). It was also shown above that the presence of the stabilizer within the SOFA-module increases the stability of SOFA-δRz-303. Here, we address the influence of the stabilizer domain, which does not have an active role in the SOFA mechanism. Both the SOFA⁺- and SOFA⁻-δRz-303 versions, with or without stabilizer sequences, were constructed and used to define the influence of this domain on the cleavage activity (FIG. 14A). As we first thought, the two SOFA⁺-δRz-303 versions exhibited the same level of cleavage activity regardless of the presence (lane 3) or absence (lane 5) of the stabilizer sequences, while their SOFA counterparts (i.e. those without the appropriate biosensor sequence) were inactive (lanes 4 and 6). These observations confirmed that the stabilizer sequences did not interfere with the cleavage activity of the SOFA-ribozyme.

Figure 14B:
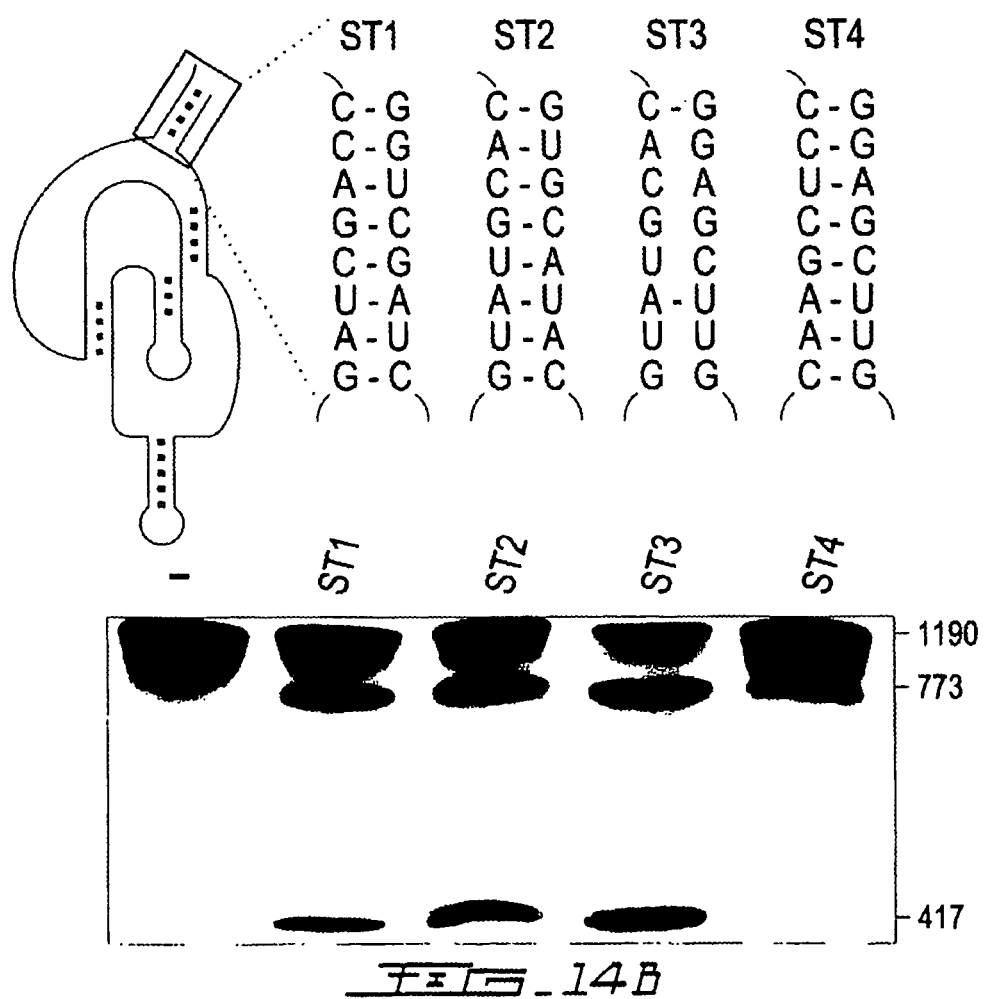
FIG. 14B illustrates the result obtained with mutated stabilizer. The upper panel illustrates the sequence of the stabilizer (SOFA-δRz-303-ST1 to -ST4), while the lower panel illustrates the autoradiogram of the 6% PAGE of the corresponding cleavage assays. The control (−) was performed in the absence of ribozyme.

Subsequently, the stabilizer was mutated to five different base pairs (see FIG. 14B, SOFA-δRz-303-ST2 as compared to -ST1) and used in the cleavage assay. As expected, both versions of SOFA-ribozyme exhibited virtually identical levels of cleavage. Similar results were observed if the mutation allowed the formation of only 2 bp within the stabilizer (FIG. 14B, SOFA-δRz-303-ST3 as compared to -ST1). These results are in good agreement with the hypothesis that the identity of the stabilizer sequence does not affect the SOFA-module action.

Surprisingly, another mutant (SOFA-δRz-303-ST4) exhibited a drastic decrease in cleavage activity, a result that contradicts all of the data previously presented. We analyzed the sequence of this ribozyme in detail and realized that the 5'-strand of the stabilizer (5'-CCUCGAAC-3') was complementary to a stretch of sequence located within the P4 stem-loop (5'-GUUCGCGG-3'). This observation suggests that this stabilizer could interact with the P4 stem-loop of the ribozyme and thereby influence the structure of the ribozyme itself.

Structural Analysis of SOFA-δRz-303

Figure 15B:
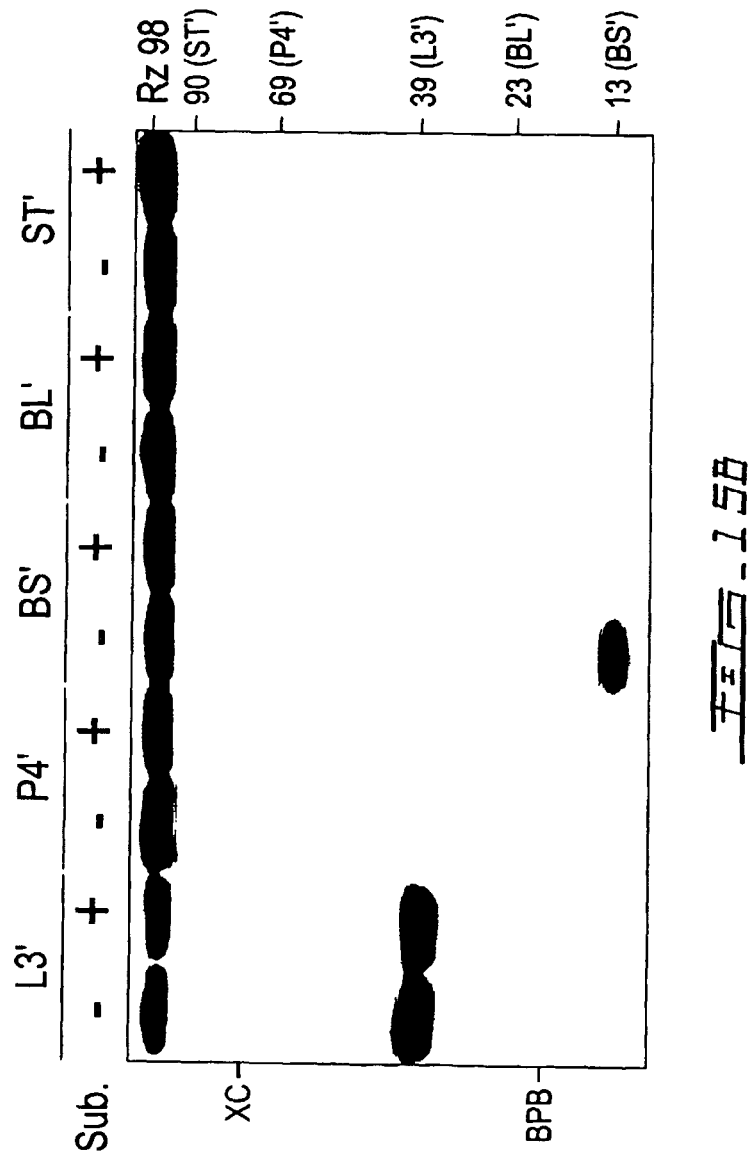
FIG. 15B illustrates an autoradiogram of an 8% denaturing PAGE of the probing assay. The symbols (−) and (+) indicate the presence or absence, respectively, of the substrate for the probing performed using each oligodeoxynucleotide (L3', P4', BS', BL' and ST'). The positions of the expected cleavage products, XC and BPB are indicated adjacent to the gel.

In order to probe both the off and on conformations of SOFA-δRz-303, we used an approach based on an oligodeoxynucleotide hybridization assay in order to distinguish between single and double stranded domains. The off and on conformations were probed in both the absence and the presence (in excess) of the 44 nucleotide model substrate (SEQ ID NO:82). With the goal of preventing cleavage, we used a SOFA-ribozyme in which the cytosine in position 76 is replaced by an adenosine (FIG. 15A, SOFA$^+$-δRzC76A-303, SEQ ID NO:83). The SOFA-ribozyme that possesses this mutation has the same binding ability as the original, but does not display any cleavage activity. Small oligodeoxynucleotides 7 nt in length complementary to various domains of the ribozyme were synthesized (FIG. 15A) and used with 5' end labelled SOFA-ribozyme in the absence (−) or presence (+) of its substrate. The RNA-DNA heteroduplexes were monitored by ribonuclease H(RNase H) hydrolysis, an enzyme that cleaves the RNA strand of such heteroduplexes. A typical gel is shown in FIG. 15B.

The oligodeoxynucleotide complementary to the L3 loop (L3') allowed the detection of a strong band of products in the absence of substrate, indicating that this region was single-stranded, in agreement with a previous report (Ananvoranich & Perreault, Biochem. Biophys. Res. Comm. 270, 600-607, 2000). The addition of the substrate also led to the detection of this band at the same intensity, confirming that L3 is still single stranded. This observation is in contradiction to what has been observed in a previous study (Ananvoranich & Perreault, Biochem. Biophys. Res. Comm. 270, 600-607, 2000), but the experiments were performed here under different conditions than in the earlier report. In this work, the oligodeoxynucleotide and the ribozyme were mixed together and incubated for 10 min prior to the addition of RNase H for the same period of incubation. These conditions favour the hybridization of the oligodeoxynucleotide to the L3 loop over the folding of the P1.1 stem that would release the oligodeoxynucleotide. Conversely, the oligodeoxynucleotide complementary to the P4 stem (P4') did not permitted the detection of any products of RNase H hydrolysis, confirming that this region is double-stranded. The oligodeoxynucleotide complementary to the biosensor sequence (BS') permitted the detection of a relatively abundant RNase H product only in the absence of the substrate, indicating that this region was single-stranded within the off conformation. Only a trace amount of the hydrolysis product was detected upon the addition of the substrate, showing that in the on conformation the biosensor is bound to its substrate and thus is double-stranded. The presence of the oligodeoxynucleotide complementary to the blocker sequence (BL') gave the opposite pattern: no RNase H product was observed in the absence of the substrate, indicating that the blocker sequence was double-stranded (with the P1 strand of the ribozyme) within the off conformation; while cleavage product was detected in the presence of the substrate, showing that, under these conditions, the blocker was single-stranded. However, a small amount of product was detected, regardless of the length of the oligodeoxynucleotide tested (e.g. slightly longer). We believe this occurs because as this region is central to the species, the RNase H hydrolysis may be limited due to steric hindrance reducing the accessibility to the RNA-DNA heteroduplex. Finally, an oligodeoxynucleotide complementary to the stabilizer (ST') did not allow for the detection of any RNase H products, confirming that this region is double-stranded regardless of the presence or absence of the substrate. In conclusion, the three segments of sequence composing the SOFA module were shown to fold into the expected structure. Moreover, the structure of the blocker and biosensor sequences were observed to be involved in the conformational transition.

SOFA-Ribozyme as Molecular Tools in Cultured Cells

In order to confirm the great potential of SOFA-ribozymes as molecular tools for gene inactivation systems, a first experiment targeting an HBV derived transcript was performed in cultured cells (FIG. 16). Briefly, the HBV C gene open reading frame was subcloned in the inducible pIND™ vector (Invitrogen) (FIG. 16A). This vector contains five modified ecdysone response elements (E/GREs) and the minimal heat shock promoter for expression of RNA of interest. Using HEK-293 cells that stably express the ecdysone receptor by which the inductor ponasterone A enters the cell, the expression of the targeted RNA can be controlled. Either the original or SOFA ribozymes were cloned downstream of the cytomegalovirus (CMV) promoter from a modified pcDNA3 vector (i.e. pmδRz; see FIG. 16B). This allowed efficient in vivo transcription by RNA polymerase II and ensure localization of the ribozymes in the cytoplasm. FIG. 16C illustrates an autoradiogram of the Northern blot hybridization demonstrating the success of the SOFA-δRz activity to diminish the RNA target level. In the presence of the original δRz-303, only a weak reduction of the RNA level was observed. However, over 60% of RNA level reduction was observed in the presence of the SOFA$^+$-δRz-303 version. Conversely, in the presence of a SOFA$^-$-δRz-303 no reduction was observed. For these three versions of ribozymes, the corresponding inactive version including a mutation of the cytosine in position 47 for an adenosine was synthesized and tested. This mutation allowed the ribozyme to bind its target with the same affinity but it is completely inactive in terms of catalytic activity. Any of these three mutants exhibited cleavage activity in vivo. The probing of the β-actin served to normalize the results. More importantly, together, these results confirmed the great potential in cell environment of the SOFA module to activate the cleavage activity solely in the presence of the good substrate.

Flexibility of the SOFA Module on δRibozyme

In order to investigate the flexibility of the SOFA module, different versions of the SOFA-δRz-303 were synthesized and their cleavage activities were assessed (FIGS. 17 and 18).

Figure 17A:
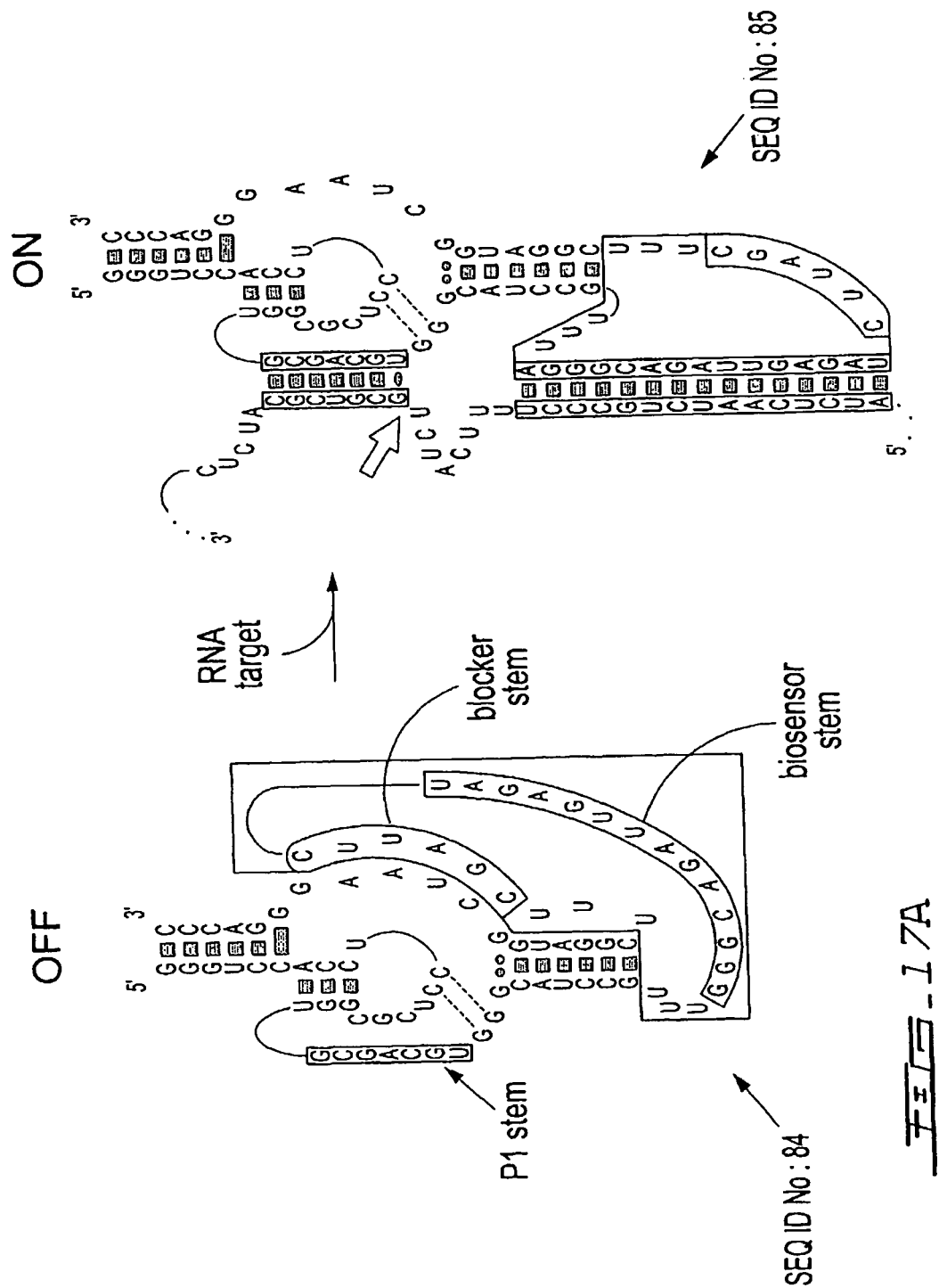
FIGS. 17A, 17B and 17C show sequences and secondary structures of the SOFA+-δRz-Down (SOFA+-δRz-DN) and SOFA+-δRz-Double (SOFA+-δRz-DB), demonstrating the versatility of the SOFA-δRz-303.
Figure 17B:
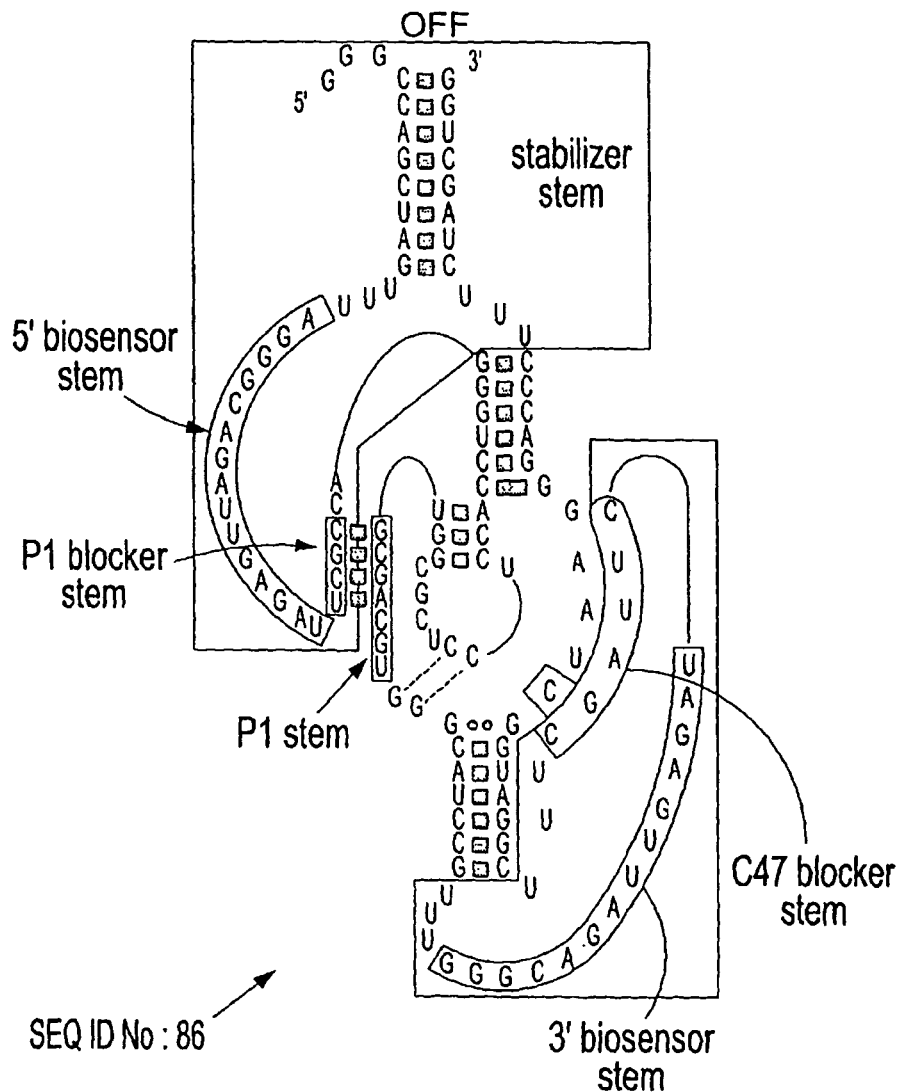
Figure 17C:
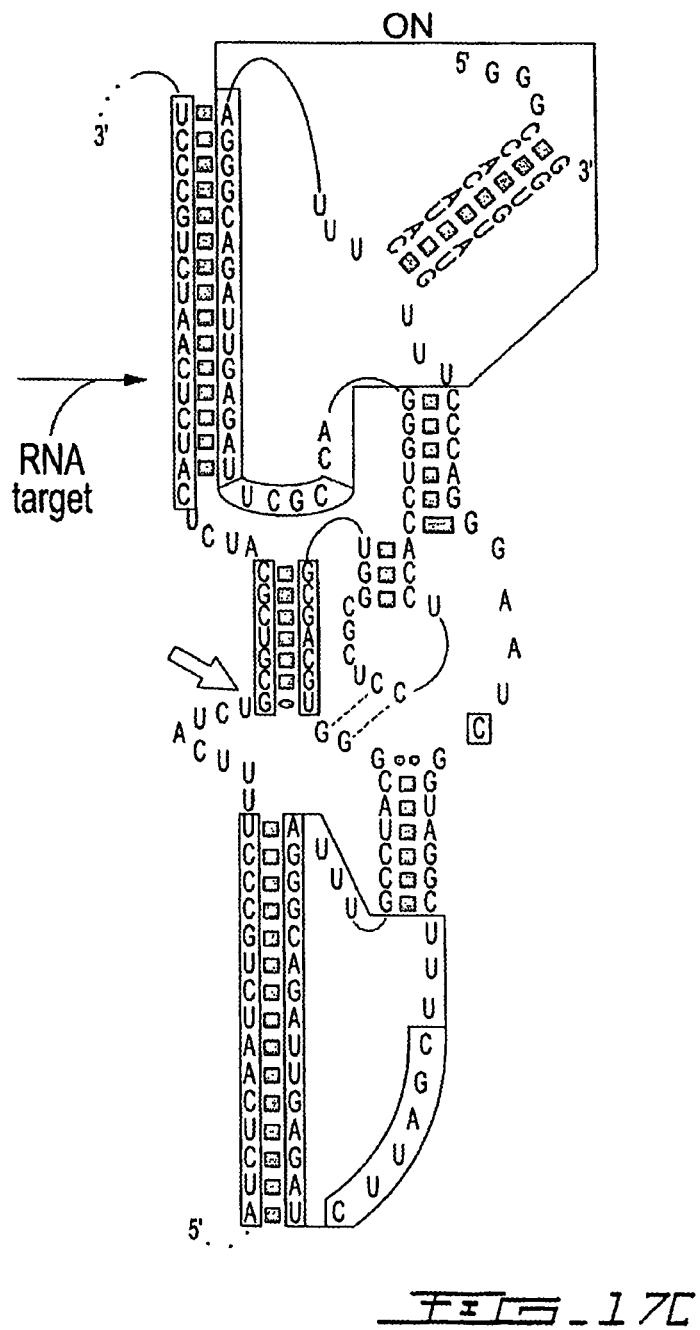
Figure 17D:
FIG. 17D illustrates autoradiograms of denaturing 6% PAGE gels performed for these cleavage assays, including a control (−) performed in the absence of ribozyme.

Firstly, the SOFA adapter was moved from the P2 stem to the P4 stem, to obtain a ribozyme called SOFA-down (SOFA-δRz-DN, DN for down, SEQ ID NO:84) (FIG. 17A). The SOFA⁺-δRz-DN cleaved relatively efficiently the transcript (SEQ ID NO:85), although at a reduced level compared to the SOFA⁺-δRz-303 (FIG. 17C). In contrast, the SOFA⁻-δRz-DN was inactive, as expected (FIG. 17C). Another variation was the construction of a "double" SOFA-ribozyme (SOFA⁺-δRz-DB, DB for double binding; see FIG. 17B, SEQ ID NO:86). This ribozyme bound the substrate (SEQ ID NO:87) through the formation of three helices involving 32 base pairs. The SOFA⁺ version exhibits a relatively high cleavage activity while the SOFA⁻ did not cleave the substrate. These results illustrate the gains in terms of substrate specificity and "safety lock" action obtained by using the concept of a blocker. It should be noted that the blocker domain of the SOFA module inserted in the L4 loop interacted with the sequence of the J4/2 junction including the C47 of the ribozyme (FIGS. 17A and 17B). Moreover, this experiment demonstrated that the position of the SOFA module is not restricted to the P2 stem of the δ ribozyme (upper part); it can also be introduced at the end of the L4 loop (lower part). This conclusion receives additional support from the design of different versions of ribozymes with SOFA modules introduced only into the L4 loop.

Figure 18A:
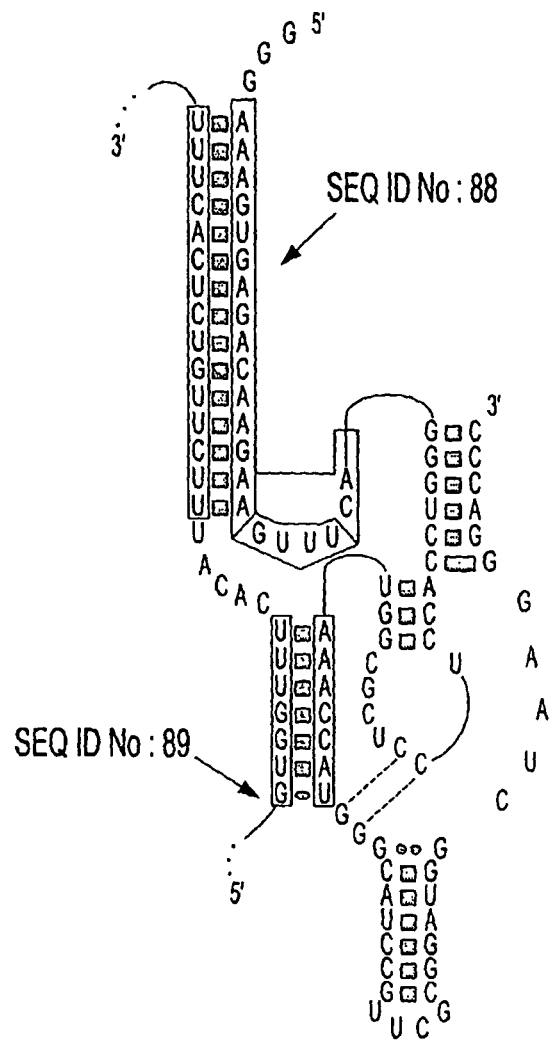
FIG. 18A illustrates the sequence and secondary structure of the SOFA$^+$-δRz without the stabilizer (SOFA$^+$-δRz-NS, NS for no stabilizer)

In order to demonstrate that the stabilizer stem do not interact with the biosensor or the blocker action, a SOFA-ribozyme lacking this domain (FIG. 18A, SEQ ID NO:88) was constructed. The SOFA⁺-δRz-NS (NS for no stabilizer) cleaved the HBV transcripts (SEQ ID NO:89) to the same extent as the original SOFA⁺-δRz-303 while the corresponding SOFA-ribozyme (SOFA⁻-δRz-NS) did not exhibit significant levels of cleavage activity (FIG. 18B). These results showed that the biosensor and blocker domains function independently of the presence of the stabilizer domain. However, independent in vivo experiments have shown that the stabilizer domain significantly increases the stability of these SOFA-ribozymes.

Summary of the SOFA Concept Controlling δRibozymes

The concept of a target-dependent module provides for a new generation of biosensorized ribozymes having a significantly improved substrate specificity and efficiency. The on conformation implies that a ribozyme with a greater affinity for its substrate subsequently cleaves them faster. Meanwhile, the off conformation prevents cleavage of an inappropriate target, acting as a "safety lock". The design of the specific on/off adapter was influenced by several factors. First, it is reminiscent of the human immune system, more specifically the cytotoxic T lymphocyte's activation mechanism. The T lymphocytes bind specific cell surface molecules which in turn dictate the T cell's responses. In the same way, the SOFA-ribozyme hybridizes to the RNA target (the activator) and specifically cleaves it. Second, the biosensor also remembers the mechanism of action of an oligodeoxynucleotide acting as facilitator for ribozyme cleavage. However, the linkage of the biosensor directly to the ribozyme permitted a great gain, in terms of cleavage activity, compared to the use of two distinct molecules. Third, the blocker stem was influenced by the TRAP strategy (for Targeted Ribozyme-Attenuated Probe) in which a 3' terminal attenuator anneals to conserved bases in the catalytic core to form the off state of a hammerhead ribozyme. The blocker domain of the SOFA module also inactivates the cleavage activity of the ribozyme by binding a sequence that is part of the catalytic core. Finally, the idea of a stabilizer domain that places the 3'-end of the SOFA module in a double-stranded region originated from the previous demonstration that the P2 stem of the δ ribozyme, which plays the same role in the wild type ribozyme, provides an outstanding stability to this RNA species. In fact, it has been shown that the δ ribozyme was at least an order of magnitude more stable compared to a hammerhead ribozyme in cultured cells. Clearly, the SOFA module is the fruit of a rational design. Using the Systematic Evolution of Ligands by EXponential enrichment (SELEX; Wilson, D S and Szostak, J W Annu. Rev. Biochem. 68, 611-647, 1999) approach it would have been impossible to develop this kind of module for a ribozyme.

All the sequence segments that might influence the efficiency of the SOFA module have been decorticated (i.e. the blocker, the biosensor, the stabilizer and the spacer). Initially, the SOFA-ribozyme is in an inactive conformation due to the action of the blocker sequence that formed a stem with the ribozyme's P1 strand, acting as a "safety lock" (FIG. 2). RNase H probing of the ribozyme alone supports the hypothesis that the blocker is engaged in a double-stranded region, while the biosensor sequence remains single stranded and accessible (FIG. 15). The optimal size for the blocker sequence was determined to be 4 nucleotides (see FIG. 12). Smaller blockers did not sufficiently prevent the ribozyme's activity, while longer blockers appeared to lock the ribozyme in its inactive conformation (in addition to leading, in some cases, to self-cleavage resulting from formation of a structure reminiscent of that of a cis-acting ribozyme). Moreover, we observed that the action of the blocker sequence of various SOFA-ribozymes couldn't be correlated with the identity of the residues composing this segment. Thus, a higher GC content in the blocker was not responsible for the lower activity of some of the SOFA-ribozymes. Regardless, there was competition between the blocker (4 bp) and the substrate (7 bp) for the P1 sequence; therefore, a higher GC content on one strand would be counterbalanced by a higher concentration on the other strand.

Since the idea of a blocker stem was inspired by the targeted ribozyme-attenuated probe (TRAP) designed for the hammerhead ribozyme, the comparison of the latter with SOFA appears to be important. Both approaches are based on the inhibition of ribozyme action due to the presence of a cis-acting antisense sequence. With TRAP, the presence of an oligodeoxynucleotide complementary to both this cis-acting sequence and a portion of the ribozyme activates the ribozyme. Consequently, there is no interaction between the oligodeoxynucleotide and the substrate. Conversely, with the SOFA module the action of the blocker is removed following the binding of the biosensor to the substrate. As a result there is no requirement for a third partner. The TRAP ribozyme has demonstrated an activation of cleavage of as much as 1760 fold, with an average of more than 250 fold. In the case of the SOFA-ribozyme higher than a 15 000 fold increase has been observed, with an average of more than 800 fold. In other words, the SOFA system brings a two order of magnitude increase in the specificity to the ribozyme's action. Thus, the SOFA concept appears to be a more efficient mode of increasing the substrate specificity of a ribozyme.

In the presence of the desired substrate, the biosensor binds the complementary substrate sequence, leading in the release of the ribozyme's P1 stem from the blocker (FIG. 2). The RNase H probing of the SOFA-ribozyme-substrate complex strongly suggest that the biosensor is base-paired with the substrate; while the blocker becomes susceptible to RNase H hydrolysis, indicating that it is single-stranded (FIG. 15). Kinetic experiments have previously shown the optimal size of the biosensor to be 10 nucleotides. We demonstrated that each SOFA-ribozyme in our collection efficiently cleaved only the substrate containing the sequence complementary to its biosensor (see FIG. 10). Substrates that included sequence with several mutations in the binding region of the biosensor were poorly cleaved. Under single turnover conditions ([Rz] >[S]), which should favour cleavage of even imperfectly base-paired substrates, only a residual rate of cleavage was observed. A similar conclusion was obtained when investigating a biosensor possessing a small number of mutations (FIG. 11). As expected, the decrease in the cleavage activity was inversely proportional to the number of mutations (ranging from 4 to 106 fold smaller in terms of $k_{obs}$). In the presence of a single mutation the reduction was estimated to be from 4 to 15 fold. However, the determination of the kinetic parameters for some mutated ribozymes led us to observe larger effects in terms of the second order rate constant ($k_{cat}/K_M$ 25 fold smaller). It should be noted that most of these experiments were performed using small substrates. A more important effect was observed with several of these SOFA-ribozymes when they were tested for the cleavage of the longer HBV-derived transcript (1190 nt). More importantly, a reduction of approximately one order of magnitude is probably sufficient for the ribozyme to be able to discriminate between two substrates, while a smaller difference would require additional precautions in order to ensure the substrate specificity for SOFA-ribozyme based cleavage in a cell. These data demonstrate the potential of the biosensor to significantly improve the substrate specificity of a ribozyme.

In both the inactive and active conformations, the SOFA-ribozymes harbour a stabilizer stem that joins the sequence found at the 5' and 3' ends into a stem (FIG. 2). This structure was confirmed by RNase H probing (FIG. 15). In terms of mechanism, it appears clear that the stabilizer does not have an active role in the SOFA module (see FIG. 14) other than the improvement of the structure's stability.

Finally, the length of the spacer sequence was investigated. The spacer sequence is not part of the SOFA-module, but it is an important parameter that influences the cleavage level. The spacer is the sequence located between the substrate P1 strand domain and the sequence complementary to the biosensor (FIG. 2). It was shown that a minimal spacer of at least one nucleotide was preferable. Moreover, short spacer sequences (1 to 5 nucleotides) appeared to have higher levels of cleavage than did longer ones (see FIG. 13). Most likely the binding of the biosensor favours the subsequent formation of the P1 stem between the ribozyme and the substrate when the spacer is short.

Together, these experiments with SOFA-δRz-303 yield a better understanding of the contribution of each of the different domains of the SOFA module. Data obtained with other ribozymes supports the hypothesis that our findings are not restricted to SOFA-δRz-303, but rather can be applied to other SOFA-δRzs.

This new approach provides a highly specific and improved tool with a lot of potential in both functional genomics and gene therapy. In terms of specificity, considering only the base pairs formed during the two binding steps between a SOFA-δ ribozyme and its substrate (7 bp for P1 binding stem+10 bp for the biosensor stem), a single site should exist per $1.7 \times 10^{10}$ bases (417). The human genome is composed of $3 \times 10^9$ base pairs, of which ~5% form mRNAs (i.e. $1.5 \times 10^8$ bases). Therefore, the substrate specificity of a SOFA⁻-δribozyme is greater than 100 fold superior to what is needed to hit one site. This initiative provides confidence in the use of ribozymes in gene therapy and functional genomic applications, even if a mismatch is tolerated in the biosensor.

SOFA Module Controlling Other Nucleic Acid Species

Figure 19F:
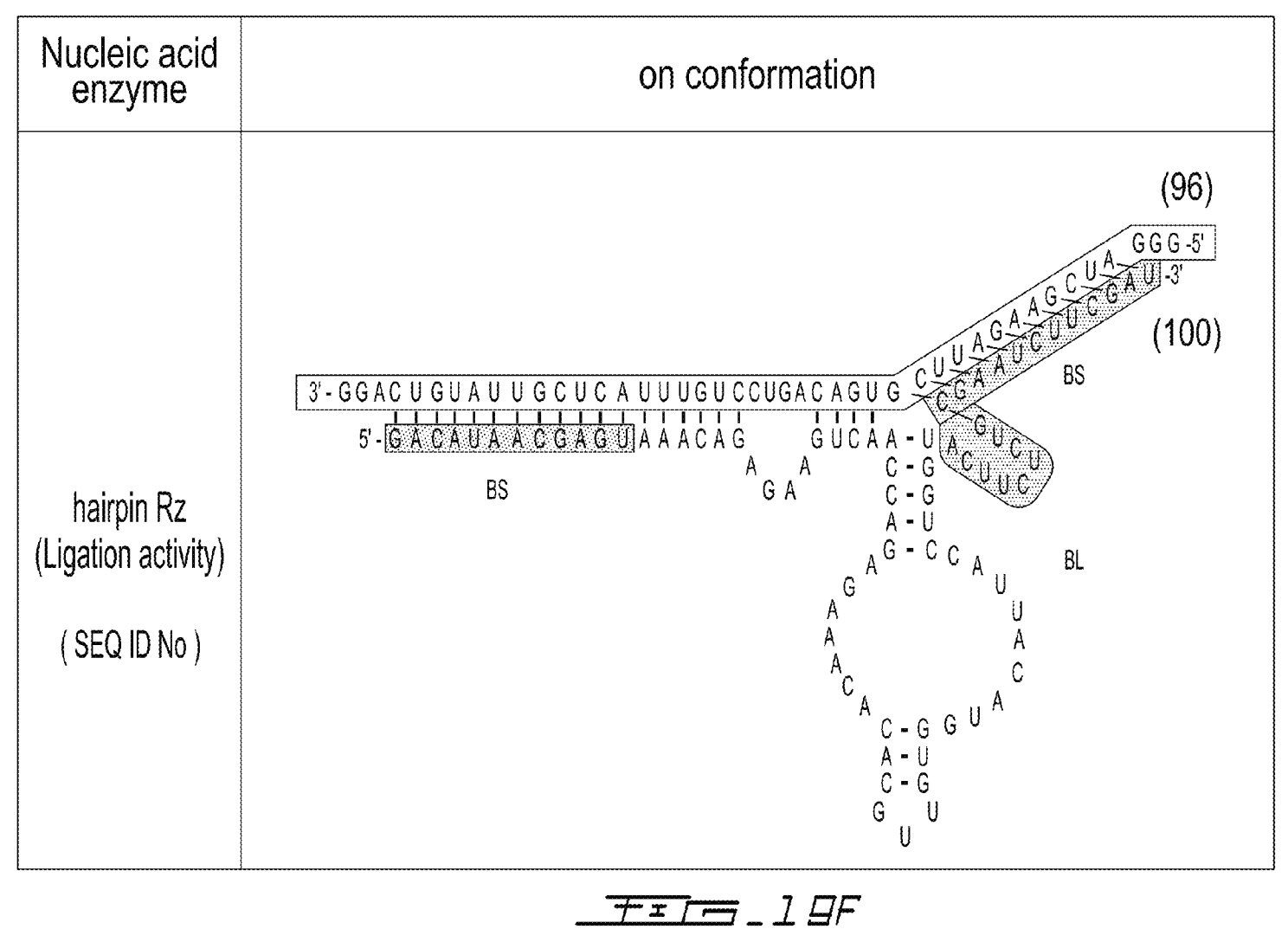

This is the first report of a ribozyme of an endonuclease-type that harbors a target-dependent module that is activated by a nucleic acid RNA substrate and then cleaves this molecule. This new concept offers great promise and should prompt a new "taking off" of the ribozyme field. Furthermore, this concept can be substantially extended to other RNA drug-based molecules that aim to cleave RNA molecules. For example, FIG. 19 illustrates one way to adapt the SOFA module to a cleaving hammerhead ribozyme, a cleaving hairpin ribozyme, a ligating hairpin ribozyme, or a cleaving DNazyme (i.e. a DNA molecule that possesses catalytic ability) (SE ID NO:90-93 and 98-101). Both the off and on (upon addition of the substrate, SEQ ID NO:94-97) conformations are illustrated. The biosensor (BS) and blocker (BL) domains are in grey. The substrates are squared. Since all motifs possess single-stranded extremities, we proposed a similar design in which the blocker is at one end while the biosensor is at the other end. This means that the SOFA module is split in two pieces (the blocker and the biosensor), each one with a specific function. The same concept of off and on conformation depending on the presence of the desired target is respected.

Moreover, a proof-of concept has been performed with the DNazyme. Cleavage assay were performed using a 5'-end $^{32}$P-labelled substrate (S) of 46 nucleotides that generates a 5'-product of 23 nucleotides. The DNazyme were purchased as DNA oligonucleotide and used directly in the experiments. The reactions were performed and illustrated in FIG. 20, which shows an autoradiogram of a 6% denaturing PAGE gel of the cleavage assays. The substrate was incubated alone (lane 1), with a DNazyme (lane 2), or with different versions of SOFA-DNazyme. The SOFA module were assessed using separately either a good or irrelevant biosensor of 14 nucleotides in size (lanes 3 and 4, respectively), and a blocker sequence of 10 nucleotides (lane 5). Finally, SOFA module (i.e. including biosensor and blocker) were tested using both an appropriate biosensor (i.e. complementary to the substrate; SOFA+-DNazyme) and an irrelevant biosensor (i.e. not complementary to the substrate; SOFA⁻-DNazyme) (lanes 6 and 7, respectively). The original DNazyme cleaved a small radiolabelled substrate while a version harboring the blocker sequence was inactive (lanes 2 and 3). A SOFA⁺-DNazyme (i.e. with a blocker and a biosensor with the appropriate sequence to target the substrate) exhibited cleavage activity while not with a SOFA⁻ (i.e. biosensor not complementary to the substrate). This shows that the SOFA concept is not restricted to δRz, and more generally to RNA.

Similarly, FIG. 21 shows an application to the silencing RNA (siRNA) which is another RNA based approach for gene-inactivation (SEQ ID NO:102 to 104). The same concept of off and on conformation depending on the presence of the desired target is respected.

Thus, this technology can also be applied to other fields such as to siRNA or any other RNA implicated in a specific disease, its development or its spreading. By adapting the biosensor sequence and the blocker sequence, the SOFA can be made specific for such siRNA or other nucleic acid, acting as an on/off switch and improving substrates specificity, even if no enzymatic activity is involved such as with ribozymes. The present invention can thus increase the popularity of siRNA which are these days often investigated as being a possible treatment for some conditions, but in life so far are not so often used due to their lack of specificity or to their immunogenicity. The present invention can also be used with success in treatment for breast cancer to prevent transcription of the faulty genes, or in treatment of Alzheimer, preventing accumulation of irrelevant RNA.

What is claimed is:

1. A method for turning on or off an enzymatic activity of a nucleic acid molecule having a catalytic core providing an enzymatic activity adapted to be matched to a substrate comprising a target sequence, said method comprising the steps of attaching to said nucleic acid molecule a nucleic acid target dependent switch adapter having a nucleic acid sequence comprising:

i) a blocker stem sequence complementary to a portion of the catalytic core of said nucleic acid molecule; and ii) a biosensor sequence having a sequence complementary to said target sequence, being spaced from the catalytic core by at least three nucleotides and having an affinity level for the target sequence greater than the affinity level of the blocker stem sequence for the catalytic center, wherein in absence of the target sequence of said substrate, said blocker stem sequence forms an intramolecular stem with the catalytic core of said nucleic acid molecule, preventing folding of the catalytic core of the nucleic acid molecule, thus locking said nucleic acid molecule in an inactive conformation, turning off the enzymatic activity and, in presence of said target sequence of said substrate, said biosensor sequence forming conventional Watson-Crick base pairs with said target sequence and said blocker stem sequence dissociating from the intramolecular stem of the catalytic core, thus permitting folding of the catalytic core of the nucleic acid molecule exposing said nucleic acid molecule in an active conformation, turning on the enzymatic activity.

2. The method of claim 1, further comprising a nucleic acid sequence forming a stabilizing stem, whereby the 3' end of the nucleic acid sequence of the switch is paired up with said nucleic acid sequence forming an intramolecular stem at the 3' end of said nucleic acid sequence of the switch, thus preventing or reducing degradation of said nucleic acid sequence switch.

3. The method of claim 2, wherein the stabilizing stem has two complementary strands, a first strand of which is linked to the 5'-end of the biosensor, and a second strand of which is complementary to the first strand and is adapted to be linked at its 5'-end to the 3'-end of the nucleic acid sequence of the switch, thus preventing exposure of a single stranded 3'-end sequence susceptible to degradation by cellular nuclease.

4. The method of claim 3, wherein the first strand of the stabilizing stem has a sequence as set forth from residue 4 to 11 of SEQ ID NO:1 and the second strand of the stabilizing stem has a sequence as set forth from residue 96 to 103 of SEQ ID NO:1.

5. The method of claim 1, wherein the blocker has a sequence specific for a ribozyme.

6. The method of claim 5, wherein the ribozyme is ribozyme delta.

7. The method of claim 6, wherein the biosensor has a sequence as set forth from residue 15 to 29 of SEQ ID NO:1.

8. The method of claim 1, wherein the blocker stem sequence has a sequence as set forth from residue 30 to 33 of SEQ ID NO:1.

9. The method of claim 1, wherein the switch adapter has the sequence as set forth in SEQ ID NO:1.

10. The method of claim 1, wherein the blocker stem sequence is linked to the biosensor.

11. The method of claim 6, wherein the nucleic acid molecule attached to said adapter is ribozyme delta.

* * * * *

SEQUENCE LISTING

<160> NUMBER OF SEQ ID NOS: 104

<210> SEQ ID NO 1
<211> LENGTH: 103
<212> TYPE: DNA
<213> ORGANISM: Artificial Sequence
<220> FEATURE:
<223> OTHER INFORMATION: SOFA-ribozyme

<400> SEQUENCE: 1
gggccagcua guuuaaagug agacaagaag uuucaggguc caccuccucg cgguaaacca        60
ugggcauccg uucgcggaug gcuaagggac ccuuucuagc ugg                         103

<210> SEQ ID NO 2
<211> LENGTH: 27
<212> TYPE: RNA
<213> ORGANISM: Artificial Sequence
<220> FEATURE:
<223> OTHER INFORMATION: Target

<400> SEQUENCE: 2
gugguuuauc ucuucuuguc ucacuuu                                            27

<210> SEQ ID NO 3
<211> LENGTH: 21
<212> TYPE: DNA
<213> ORGANISM: Artificial Sequence
<220> FEATURE:
<223> OTHER INFORMATION: T7 sense primer

<400> SEQUENCE: 3
ttaatacgac tcactatagg g                                                  21

<210> SEQ ID NO 4
<211> LENGTH: 62
<212> TYPE: DNA
<213> ORGANISM: Artificial Sequence
<220> FEATURE:
<223> OTHER INFORMATION: antisense primer

<400> SEQUENCE: 4
cttccaaaag tgagacaaga aatgtgaaac cacaagagtt gccctatagt gagtcgtatt        60
aa                                                                       62

<210> SEQ ID NO 5
<211> LENGTH: 74
<212> TYPE: DNA
<213> ORGANISM: Artificial Sequence
<220> FEATURE:
<223> OTHER INFORMATION: Antisense oligonucleotide Rz-down
<220> FEATURE:
<221> NAME/KEY: misc_feature
<222> LOCATION: 44, 45, 46, 47, 48, 49, 71, 72, 73, 74
<223> OTHER INFORMATION: n = A,T,C or G

<400> SEQUENCE: 5
ccagctagaa agggtcccct agccatccgc gaacggatgc ccannnnnna ccgcgaggag        60
gtggaccctg nnnn                                                          74

<210> SEQ ID NO 6
<211> LENGTH: 67
<212> TYPE: DNA

```
<213> ORGANISM: Artificial Sequence
<220> FEATURE:
<223> OTHER INFORMATION: sense primer Rz-up
<220> FEATURE:
<221> NAME/KEY: misc_feature
<222> LOCATION: 33, 34, 35, 36, 37, 38, 39
<223> OTHER INFORMATION: n = A,T,C or G
<220> FEATURE:
<221> NAME/KEY: misc_feature
<222> LOCATION: 40, 41, 42, 43, 44, 45, 46, 47, 48, 49, 50, 51, 52
<223> OTHER INFORMATION: n = A,T,C or G, or is absent
<220> FEATURE:
<221> NAME/KEY: misc_feature
<222> LOCATION: 53, 54, 55, 56
<223> OTHER INFORMATION: n = A,T,C or G

<400> SEQUENCE: 6
ttaatacgac tcactatagg gccagctagt ttnnnnnnnn nnnnnnnnnn nnnnnncagg    60
gtccacc                                                              67

<210> SEQ ID NO 7
<211> LENGTH: 53
<212> TYPE: DNA
<213> ORGANISM: Artificial Sequence
<220> FEATURE:
<223> OTHER INFORMATION: substrate a

<400> SEQUENCE: 7
aaagtgagac aagaaatgtg aaaccacaag agccctatag tgagtcgtat taa            53

<210> SEQ ID NO 8
<211> LENGTH: 59
<212> TYPE: DNA
<213> ORGANISM: Artificial Sequence
<220> FEATURE:
<223> OTHER INFORMATION: substrate b

<400> SEQUENCE: 8
aaagtagact gagatatgtg aaaccacaag agtgtactcc ctatagtgag tcgtattaa      59

<210> SEQ ID NO 9
<211> LENGTH: 61
<212> TYPE: DNA
<213> ORGANISM: Artificial Sequence
<220> FEATURE:
<223> OTHER INFORMATION: substrate c

<400> SEQUENCE: 9
aaagtgttca gcactatgtg aaaccacaag agtgtactgt ccctatagtg agtcgtatta    60
a                                                                    61

<210> SEQ ID NO 10
<211> LENGTH: 63
<212> TYPE: DNA
<213> ORGANISM: Artificial Sequence
<220> FEATURE:
<223> OTHER INFORMATION: substrate d

<400> SEQUENCE: 10
aaagtaggat acgggatgtg aaaccacaag agtgtactgt aaccctatag tgagtcgtat    60
taa                                                                  63

<210> SEQ ID NO 11
<211> LENGTH: 65
<212> TYPE: DNA
<213> ORGANISM: Artificial Sequence
```

```
<220> FEATURE:
<223> OTHER INFORMATION: substrate e

<400> SEQUENCE: 11
aaagtagtct ggatcatgtg aaaccacaag agtgtactgt aactccctat agtgagtcgt    60
attaa                                                                65

<210> SEQ ID NO 12
<211> LENGTH: 67
<212> TYPE: DNA
<213> ORGANISM: Artificial Sequence
<220> FEATURE:
<223> OTHER INFORMATION: substrate f

<400> SEQUENCE: 12
aaagtggcat aatcaatgtg aaaccacaag agtgtactgt aacttcccct atagtgagtc    60
gtattaa                                                              67

<210> SEQ ID NO 13
<211> LENGTH: 69
<212> TYPE: DNA
<213> ORGANISM: Artificial Sequence
<220> FEATURE:
<223> OTHER INFORMATION: substrate g

<400> SEQUENCE: 13
aaagtaagtt ggcgaatgtg aaaccacaag agtgtactgt aacttcaacc ctatagtgag    60
tcgtattaa                                                            69

<210> SEQ ID NO 14
<211> LENGTH: 71
<212> TYPE: DNA
<213> ORGANISM: Artificial Sequence
<220> FEATURE:
<223> OTHER INFORMATION: substrate h

<400> SEQUENCE: 14
aaagtgtact catgcatgtg aaaccacaag agtgtactgt aacttcaatg ccctatagtg    60
agtcgtatta a                                                         71

<210> SEQ ID NO 15
<211> LENGTH: 55
<212> TYPE: DNA
<213> ORGANISM: Artificial Sequence
<220> FEATURE:
<223> OTHER INFORMATION: antisense primer
<220> FEATURE:
<221> NAME/KEY: misc_feature
<222> LOCATION: (16)...(21)
<223> OTHER INFORMATION: n= A or nothing
<220> FEATURE:
<221> NAME/KEY: repeat_unit
<222> LOCATION: (22)...(28)
<223> OTHER INFORMATION: Unit repeated 7 times

<400> SEQUENCE: 15
aaagtgagac aagaannnnn naaaccacaa aaaccctat agtgagtcgt attaa           55

<210> SEQ ID NO 16
<211> LENGTH: 68
<212> TYPE: DNA
<213> ORGANISM: Artificial Sequence
<220> FEATURE:
<223> OTHER INFORMATION: antisense primer
<220> FEATURE:
```

```
<221> NAME/KEY: misc_feature
<222> LOCATION: (16)...(20)
<223> OTHER INFORMATION: spacer
<220> FEATURE:
<221> NAME/KEY: repeat_unit
<222> LOCATION: (21)...(27)
<223> OTHER INFORMATION: repeated as desired
<220> FEATURE:
<221> NAME/KEY: misc_feature
<222> LOCATION: (28)...(34)
<223> OTHER INFORMATION: cleavable P1 sequence
<220> FEATURE:
<221> NAME/KEY: repeat_unit
<222> LOCATION: (35)...(41)
<223> OTHER INFORMATION: repeated as desired

<400> SEQUENCE: 16
aaagtgagac aagaaaaaac accaacaaaa ccacaccaac aaaaaaaccc tatagtgagt    60
cgtattaa                                                             68

<210> SEQ ID NO 17
<211> LENGTH: 39
<212> TYPE: DNA
<213> ORGANISM: Artificial Sequence
<220> FEATURE:
<223> OTHER INFORMATION: forward primer

<400> SEQUENCE: 17
tatctaaagc tagcttcatg tcctactgtt caagcctcc                           39

<210> SEQ ID NO 18
<211> LENGTH: 37
<212> TYPE: DNA
<213> ORGANISM: Artificial Sequence
<220> FEATURE:
<223> OTHER INFORMATION: reverse primer

<400> SEQUENCE: 18
tagtgaaact cgagaataaa gcccagtaaa gttccca                             37

<210> SEQ ID NO 19
<211> LENGTH: 34
<212> TYPE: DNA
<213> ORGANISM: Artificial Sequence
<220> FEATURE:
<223> OTHER INFORMATION: oligonucleotide used to synthetize a cassette

<400> SEQUENCE: 19
agcttggtac cgagtccgga tatcaataaa atgc                                34

<210> SEQ ID NO 20
<211> LENGTH: 34
<212> TYPE: DNA
<213> ORGANISM: Artificial Sequence
<220> FEATURE:
<223> OTHER INFORMATION: oligonucleotide used to synthetize a cassette

<400> SEQUENCE: 20
tcgagcattt tattgatatc cggactcggt acca                                34

<210> SEQ ID NO 21
<211> LENGTH: 28
<212> TYPE: DNA
<213> ORGANISM: Artificial Sequence
<220> FEATURE:
<223> OTHER INFORMATION: forward primer

<400> SEQUENCE: 21
```

```
atccatcggg taccgggcca gttagttt                                    28
```

<210> SEQ ID NO 22
<211> LENGTH: 31
<212> TYPE: DNA
<213> ORGANISM: Artificial Sequence
<220> FEATURE:
<223> OTHER INFORMATION: reverse primer

<400> SEQUENCE: 22

```
ccagctagaa agggtccctt agccatccgc g                                31
```

<210> SEQ ID NO 23
<211> LENGTH: 15
<212> TYPE: DNA
<213> ORGANISM: Artificial Sequence
<220> FEATURE:
<223> OTHER INFORMATION: facilitator (FCO)

<400> SEQUENCE: 23

```
aaagtgagac aagaa                                                  15
```

<210> SEQ ID NO 24
<211> LENGTH: 15
<212> TYPE: DNA
<213> ORGANISM: Artificial Sequence
<220> FEATURE:
<223> OTHER INFORMATION: biosensor stem (BSO)

<400> SEQUENCE: 24

```
ttcttgtctc acttt                                                  15
```

<210> SEQ ID NO 25
<211> LENGTH: 15
<212> TYPE: DNA
<213> ORGANISM: Artificial Sequence
<220> FEATURE:
<223> OTHER INFORMATION: unrelated oligonucleotide (UNO)

<400> SEQUENCE: 25

```
cccaatacca catca                                                  15
```

<210> SEQ ID NO 26
<211> LENGTH: 35
<212> TYPE: RNA
<213> ORGANISM: Artificial Sequence
<220> FEATURE:
<223> OTHER INFORMATION: Substrate

<400> SEQUENCE: 26

```
gggcucuugu gguuucacau uucuugucuc acuuu                            35
```

<210> SEQ ID NO 27
<211> LENGTH: 39
<212> TYPE: RNA
<213> ORGANISM: Artificial Sequence
<220> FEATURE:
<223> OTHER INFORMATION: Substrate

<400> SEQUENCE: 27

```
ggguacacuc uugugguuuc acaucaggca ccucacuuu                        39
```

<210> SEQ ID NO 28
<211> LENGTH: 41
<212> TYPE: RNA

<213> ORGANISM: Artificial Sequence
<220> FEATURE:
<223> OTHER INFORMATION: Substrate

<400> SEQUENCE: 28
gggaguacac ucuugugguu ucacauaucu cagucuacuu u         41

<210> SEQ ID NO 29
<211> LENGTH: 43
<212> TYPE: RNA
<213> ORGANISM: Artificial Sequence
<220> FEATURE:
<223> OTHER INFORMATION: Substrate

<400> SEQUENCE: 29
gggacaguac acucuugugg uuucacauag ugcugaacac uuu        43

<210> SEQ ID NO 30
<211> LENGTH: 45
<212> TYPE: RNA
<213> ORGANISM: Artificial Sequence
<220> FEATURE:
<223> OTHER INFORMATION: Substrate

<400> SEQUENCE: 30
ggguuacagu acacucuugu gguuucacau cccguauccu acuuu       45

<210> SEQ ID NO 31
<211> LENGTH: 47
<212> TYPE: RNA
<213> ORGANISM: Artificial Sequence
<220> FEATURE:
<223> OTHER INFORMATION: Substrate

<400> SEQUENCE: 31
gggaguuaca guacacucuu gugguuucac augauccaga cuacuuu      47

<210> SEQ ID NO 32
<211> LENGTH: 49
<212> TYPE: RNA
<213> ORGANISM: Artificial Sequence
<220> FEATURE:
<223> OTHER INFORMATION: Substrate

<400> SEQUENCE: 32
ggggaaguua caguacacuc uugugguuuc acauugauua ugccacuuu     49

<210> SEQ ID NO 33
<211> LENGTH: 51
<212> TYPE: RNA
<213> ORGANISM: Artificial Sequence
<220> FEATURE:
<223> OTHER INFORMATION: Substrate

<400> SEQUENCE: 33
ggguugaagu acaguacac ucuugugguu ucacauucgc caacuuacuu u    51

<210> SEQ ID NO 34
<211> LENGTH: 53
<212> TYPE: RNA
<213> ORGANISM: Artificial Sequence
<220> FEATURE:
<223> OTHER INFORMATION: Substrate

<400> SEQUENCE: 34
gggcauugaa guuacaguac acucuugugg uuucacaugc augaguacac uuu    53

<210> SEQ ID NO 35
<211> LENGTH: 55
<212> TYPE: RNA
<213> ORGANISM: Artificial Sequence
<220> FEATURE:
<223> OTHER INFORMATION: Substrate

<400> SEQUENCE: 35
gggugcauug aaguuacagu acacucuugu gguuucacau cugugcugca acuuu    55

<210> SEQ ID NO 36
<211> LENGTH: 42
<212> TYPE: DNA
<213> ORGANISM: Artificial Sequence
<220> FEATURE:
<223> OTHER INFORMATION: Targeting site

<400> SEQUENCE: 36
ggcaactctt gtggtttcac atttcttgtc tcacttttgg aa    42

<210> SEQ ID NO 37
<211> LENGTH: 42
<212> TYPE: DNA
<213> ORGANISM: Artificial Sequence
<220> FEATURE:
<223> OTHER INFORMATION: Targeting site

<400> SEQUENCE: 37
ctcaatcgcc gcgtcgcaga agatctcaat ctcgggaatc tc    42

<210> SEQ ID NO 38
<211> LENGTH: 42
<212> TYPE: DNA
<213> ORGANISM: Artificial Sequence
<220> FEATURE:
<223> OTHER INFORMATION: Targeting site

<400> SEQUENCE: 38
ccagcttata gaccaccaaa tgcccctatc ctatcaacac tt    42

<210> SEQ ID NO 39
<211> LENGTH: 42
<212> TYPE: DNA
<213> ORGANISM: Artificial Sequence
<220> FEATURE:
<223> OTHER INFORMATION: Targeting site

<400> SEQUENCE: 39
attctttccc gaccaccagt tggatccagc cttcagagca aa    42

<210> SEQ ID NO 40
<211> LENGTH: 42
<212> TYPE: DNA
<213> ORGANISM: Artificial Sequence
<220> FEATURE:
<223> OTHER INFORMATION: Targeting site

<400> SEQUENCE: 40
agatttgggc gtgccccgc gagactgcta gccgagtagt gt    42

<210> SEQ ID NO 41
<211> LENGTH: 41
<212> TYPE: DNA
<213> ORGANISM: Artificial Sequence
<220> FEATURE:

<223> OTHER INFORMATION: Targeting site

<400> SEQUENCE: 41
gtgcttgcga gtgcccggga ggtctcgtag accgtgcacc a    41

<210> SEQ ID NO 42
<211> LENGTH: 10
<212> TYPE: DNA
<213> ORGANISM: Artificial Sequence
<220> FEATURE:
<223> OTHER INFORMATION: Substrate a

<400> SEQUENCE: 42
cucuguucuu    10

<210> SEQ ID NO 43
<211> LENGTH: 10
<212> TYPE: DNA
<213> ORGANISM: Artificial Sequence
<220> FEATURE:
<223> OTHER INFORMATION: Substrate b

<400> SEQUENCE: 43
ucugacucua    10

<210> SEQ ID NO 44
<211> LENGTH: 10
<212> TYPE: DNA
<213> ORGANISM: Artificial Sequence
<220> FEATURE:
<223> OTHER INFORMATION: Substrate c

<400> SEQUENCE: 44
caagucguga    10

<210> SEQ ID NO 45
<211> LENGTH: 10
<212> TYPE: DNA
<213> ORGANISM: Artificial Sequence
<220> FEATURE:
<223> OTHER INFORMATION: Substrate d

<400> SEQUENCE: 45
uccuaugccc    10

<210> SEQ ID NO 46
<211> LENGTH: 10
<212> TYPE: DNA
<213> ORGANISM: Artificial Sequence
<220> FEATURE:
<223> OTHER INFORMATION: Substrate e

<400> SEQUENCE: 46
ucagaccuag    10

<210> SEQ ID NO 47
<211> LENGTH: 10
<212> TYPE: DNA
<213> ORGANISM: Artificial Sequence
<220> FEATURE:
<223> OTHER INFORMATION: Substrate f

<400> SEQUENCE: 47
ccguauuagu    10

-continued

```
<210> SEQ ID NO 48
<211> LENGTH: 10
<212> TYPE: DNA
<213> ORGANISM: Artificial Sequence
<220> FEATURE:
<223> OTHER INFORMATION: Substrate g

<400> SEQUENCE: 48
uucaaccgcu                                                                10

<210> SEQ ID NO 49
<211> LENGTH: 10
<212> TYPE: DNA
<213> ORGANISM: Artificial Sequence
<220> FEATURE:
<223> OTHER INFORMATION: Substrate h

<400> SEQUENCE: 49
caugaguacg                                                                10

<210> SEQ ID NO 50
<211> LENGTH: 10
<212> TYPE: DNA
<213> ORGANISM: Artificial Sequence
<220> FEATURE:
<223> OTHER INFORMATION: Ribozyme A

<400> SEQUENCE: 50
gagacaagaa                                                                10

<210> SEQ ID NO 51
<211> LENGTH: 10
<212> TYPE: DNA
<213> ORGANISM: Artificial Sequence
<220> FEATURE:
<223> OTHER INFORMATION: Ribozyme B

<400> SEQUENCE: 51
agacugagau                                                                10

<210> SEQ ID NO 52
<211> LENGTH: 10
<212> TYPE: DNA
<213> ORGANISM: Artificial Sequence
<220> FEATURE:
<223> OTHER INFORMATION: Ribozyme C

<400> SEQUENCE: 52
guucagcacu                                                                10

<210> SEQ ID NO 53
<211> LENGTH: 10
<212> TYPE: DNA
<213> ORGANISM: Artificial Sequence
<220> FEATURE:
<223> OTHER INFORMATION: Ribozyme D

<400> SEQUENCE: 53
aggauacggg                                                                10

<210> SEQ ID NO 54
<211> LENGTH: 10
<212> TYPE: DNA
<213> ORGANISM: Artificial Sequence
<220> FEATURE:
<223> OTHER INFORMATION: Ribozyme E
```

```
<400> SEQUENCE: 54
agucuggauc                                                          10

<210> SEQ ID NO 55
<211> LENGTH: 10
<212> TYPE: DNA
<213> ORGANISM: Artificial Sequence
<220> FEATURE:
<223> OTHER INFORMATION: Ribozyme  F

<400> SEQUENCE: 55
ggcauaauca                                                          10

<210> SEQ ID NO 56
<211> LENGTH: 10
<212> TYPE: DNA
<213> ORGANISM: Artificial Sequence
<220> FEATURE:
<223> OTHER INFORMATION: Ribozyme G

<400> SEQUENCE: 56
aaguuggcga                                                          10

<210> SEQ ID NO 57
<211> LENGTH: 10
<212> TYPE: DNA
<213> ORGANISM: Artificial Sequence
<220> FEATURE:
<223> OTHER INFORMATION: Ribozyme H

<400> SEQUENCE: 57
guacucaugc                                                          10

<210> SEQ ID NO 58
<211> LENGTH: 10
<212> TYPE: DNA
<213> ORGANISM: Artificial Sequence
<220> FEATURE:
<223> OTHER INFORMATION: Ribozyme 0

<400> SEQUENCE: 58
gagacaagaa                                                          10

<210> SEQ ID NO 59
<211> LENGTH: 10
<212> TYPE: DNA
<213> ORGANISM: Artificial Sequence
<220> FEATURE:
<223> OTHER INFORMATION: Ribozyme 1

<400> SEQUENCE: 59
cagacaagaa                                                          10

<210> SEQ ID NO 60
<211> LENGTH: 10
<212> TYPE: DNA
<213> ORGANISM: Artificial Sequence
<220> FEATURE:
<223> OTHER INFORMATION: Ribozyme 2

<400> SEQUENCE: 60
gugacaagaa                                                          10

<210> SEQ ID NO 61
<211> LENGTH: 10
```

```
<212> TYPE: DNA
<213> ORGANISM: Artificial Sequence
<220> FEATURE:
<223> OTHER INFORMATION: Ribozyme 3

<400> SEQUENCE: 61
gcgacaagaa                                                              10

<210> SEQ ID NO 62
<211> LENGTH: 10
<212> TYPE: DNA
<213> ORGANISM: Artificial Sequence
<220> FEATURE:
<223> OTHER INFORMATION: Ribozyme 4

<400> SEQUENCE: 62
gacacaagaa                                                              10

<210> SEQ ID NO 63
<211> LENGTH: 10
<212> TYPE: DNA
<213> ORGANISM: Artificial Sequence
<220> FEATURE:
<223> OTHER INFORMATION: Ribozyme 5

<400> SEQUENCE: 63
gagucaagaa                                                              10

<210> SEQ ID NO 64
<211> LENGTH: 10
<212> TYPE: DNA
<213> ORGANISM: Artificial Sequence
<220> FEATURE:
<223> OTHER INFORMATION: Ribozyme 6

<400> SEQUENCE: 64
gagagaagaa                                                              10

<210> SEQ ID NO 65
<211> LENGTH: 10
<212> TYPE: DNA
<213> ORGANISM: Artificial Sequence
<220> FEATURE:
<223> OTHER INFORMATION: Ribozyme 7

<400> SEQUENCE: 65
gagacuagaa                                                              10

<210> SEQ ID NO 66
<211> LENGTH: 10
<212> TYPE: DNA
<213> ORGANISM: Artificial Sequence
<220> FEATURE:
<223> OTHER INFORMATION: Ribozyme 8

<400> SEQUENCE: 66
gagaccagaa                                                              10

<210> SEQ ID NO 67
<211> LENGTH: 10
<212> TYPE: DNA
<213> ORGANISM: Artificial Sequence
<220> FEATURE:
<223> OTHER INFORMATION: Ribozyme 9

<400> SEQUENCE: 67
```
gagacaugaa                                                                     10

<210> SEQ ID NO 68
<211> LENGTH: 10
<212> TYPE: DNA
<213> ORGANISM: Artificial Sequence
<220> FEATURE:
<223> OTHER INFORMATION: Ribozyme 10

<400> SEQUENCE: 68
gagacaacaa                                                                     10

<210> SEQ ID NO 69
<211> LENGTH: 10
<212> TYPE: DNA
<213> ORGANISM: Artificial Sequence
<220> FEATURE:
<223> OTHER INFORMATION: Ribozyme 11

<400> SEQUENCE: 69
gagacaagua                                                                     10

<210> SEQ ID NO 70
<211> LENGTH: 10
<212> TYPE: DNA
<213> ORGANISM: Artificial Sequence
<220> FEATURE:
<223> OTHER INFORMATION: Ribozyme 12

<400> SEQUENCE: 70
gagacaagca                                                                     10

<210> SEQ ID NO 71
<211> LENGTH: 10
<212> TYPE: DNA
<213> ORGANISM: Artificial Sequence
<220> FEATURE:
<223> OTHER INFORMATION: Ribozyme 13

<400> SEQUENCE: 71
gagacaagau                                                                     10

<210> SEQ ID NO 72
<211> LENGTH: 10
<212> TYPE: DNA
<213> ORGANISM: Artificial Sequence
<220> FEATURE:
<223> OTHER INFORMATION: Ribozyme 14

<400> SEQUENCE: 72
gugacaagua                                                                     10

<210> SEQ ID NO 73
<211> LENGTH: 10
<212> TYPE: DNA
<213> ORGANISM: Artificial Sequence
<220> FEATURE:
<223> OTHER INFORMATION: Ribozyme 15

<400> SEQUENCE: 73
gagaguagaa                                                                     10

<210> SEQ ID NO 74
<211> LENGTH: 10
<212> TYPE: DNA
<213> ORGANISM: Artificial Sequence

```
<220> FEATURE:
<223> OTHER INFORMATION: Ribozyme 16

<400> SEQUENCE: 74
gagacuagua                                                          10

<210> SEQ ID NO 75
<211> LENGTH: 10
<212> TYPE: DNA
<213> ORGANISM: Artificial Sequence
<220> FEATURE:
<223> OTHER INFORMATION: Ribozyme 17

<400> SEQUENCE: 75
gagaccagca                                                          10

<210> SEQ ID NO 76
<211> LENGTH: 10
<212> TYPE: DNA
<213> ORGANISM: Artificial Sequence
<220> FEATURE:
<223> OTHER INFORMATION: Ribozyme 18

<400> SEQUENCE: 76
cugacuagaa                                                          10

<210> SEQ ID NO 77
<211> LENGTH: 10
<212> TYPE: DNA
<213> ORGANISM: Artificial Sequence
<220> FEATURE:
<223> OTHER INFORMATION: Ribozyme 19

<400> SEQUENCE: 77
gugacuagua                                                          10

<210> SEQ ID NO 78
<211> LENGTH: 10
<212> TYPE: DNA
<213> ORGANISM: Artificial Sequence
<220> FEATURE:
<223> OTHER INFORMATION: Ribozyme 20

<400> SEQUENCE: 78
gagacuacua                                                          10

<210> SEQ ID NO 79
<211> LENGTH: 10
<212> TYPE: DNA
<213> ORGANISM: Artificial Sequence
<220> FEATURE:
<223> OTHER INFORMATION: Ribozyme 21

<400> SEQUENCE: 79
cucacaagau                                                          10

<210> SEQ ID NO 80
<211> LENGTH: 10
<212> TYPE: DNA
<213> ORGANISM: Artificial Sequence
<220> FEATURE:
<223> OTHER INFORMATION: Ribozyme 22

<400> SEQUENCE: 80
gugacuaguu                                                          10
```

```
<210> SEQ ID NO 81
<211> LENGTH: 10
<212> TYPE: DNA
<213> ORGANISM: Artificial Sequence
<220> FEATURE:
<223> OTHER INFORMATION: Ribozyme 23

<400> SEQUENCE: 81
gacacaucua                                                              10

<210> SEQ ID NO 82
<211> LENGTH: 44
<212> TYPE: DNA
<213> ORGANISM: Artificial Sequence
<220> FEATURE:
<223> OTHER INFORMATION: Substrate

<400> SEQUENCE: 82
gggcaacucu ugugguuuau cucuucuugu cucacuuuug gaag                        44

<210> SEQ ID NO 83
<211> LENGTH: 98
<212> TYPE: DNA
<213> ORGANISM: Artificial Sequence
<220> FEATURE:
<223> OTHER INFORMATION: SOFA-Ribozyme

<400> SEQUENCE: 83
gggccagcua guuugagaca agaaguuuca gguccaccu ccucgcggua aaccaugggc        60
auccguucgc ggauggauaa gggacccuuu cuagcugg                              98

<210> SEQ ID NO 84
<211> LENGTH: 79
<212> TYPE: DNA
<213> ORGANISM: Artificial Sequence
<220> FEATURE:
<223> OTHER INFORMATION: SOFA down

<400> SEQUENCE: 84
ggguccaccu ccucgcggug cgacgugggc aucccuuugg gcagauugag aucuuagcuu       60
ucggauggcu aagggaccc                                                   79

<210> SEQ ID NO 85
<211> LENGTH: 35
<212> TYPE: DNA
<213> ORGANISM: Artificial Sequence
<220> FEATURE:
<223> OTHER INFORMATION: Substrate

<400> SEQUENCE: 85
aucucaaucu gcccuuuuca ucugcgucgc aucuc                                 35

<210> SEQ ID NO 86
<211> LENGTH: 125
<212> TYPE: DNA
<213> ORGANISM: Artificial Sequence
<220> FEATURE:
<223> OTHER INFORMATION: Double-SOFA-ribozyme

<400> SEQUENCE: 86
gggccagcua guuuagggca gauugagauu cgccagggu caccuccucg cggugcgacg        60
ugggcauccg uuuggggcaga uugagaucuu agcuuucgga uggcuaaggg acccuuucua     120
gcugg                                                                 125
```

<210> SEQ ID NO 87
<211> LENGTH: 50
<212> TYPE: DNA
<213> ORGANISM: Artificial Sequence
<220> FEATURE:
<223> OTHER INFORMATION: Substrate

<400> SEQUENCE: 87
aucucaaucu gcccuuuuca ucugcgucgc aucucaucuc aaucugcccu    50

<210> SEQ ID NO 88
<211> LENGTH: 27
<212> TYPE: DNA
<213> ORGANISM: Artificial Sequence
<220> FEATURE:
<223> OTHER INFORMATION: Ribozyme

<400> SEQUENCE: 88
gugguuucac auuucuuguc ucacuuu    27

<210> SEQ ID NO 89
<211> LENGTH: 81
<212> TYPE: DNA
<213> ORGANISM: Artificial Sequence
<220> FEATURE:
<223> OTHER INFORMATION: Substrate

<400> SEQUENCE: 89
gggaaaguga gacaagaagu ucagggucc accuccucgc gguaaaccau gggcauccgu    60
ucgcggaugg cuaagggacc c    81

<210> SEQ ID NO 90
<211> LENGTH: 37
<212> TYPE: DNA
<213> ORGANISM: Artificial Sequence
<220> FEATURE:
<223> OTHER INFORMATION: Hammerhead ribozyme - WT

<400> SEQUENCE: 90
uuggugucug augaguccgu gaggacgaaa cguuugg    37

<210> SEQ ID NO 91
<211> LENGTH: 50
<212> TYPE: DNA
<213> ORGANISM: Artificial Sequence
<220> FEATURE:
<223> OTHER INFORMATION: Hairpin Rz (cleavage activity) - WT

<400> SEQUENCE: 91
aaacagagaa gucaaccaga gaaacacacg uugugguaca uuaccuggua    50

<210> SEQ ID NO 92
<211> LENGTH: 50
<212> TYPE: DNA
<213> ORGANISM: Artificial Sequence
<220> FEATURE:
<223> OTHER INFORMATION: Hairpin Rz (ligation activity) - WT

<400> SEQUENCE: 92
aaacagagaa gucaaccaga gaaacacacg uugugguaca uuaccuggua    50

<210> SEQ ID NO 93
<211> LENGTH: 33
<212> TYPE: DNA

<213> ORGANISM: Artificial Sequence
<220> FEATURE:
<223> OTHER INFORMATION: DNazyme (cleavage activity) - WT

<400> SEQUENCE: 93
ccggggaaag gctagctaca acgaagaagt gct                          33

<210> SEQ ID NO 94
<211> LENGTH: 31
<212> TYPE: DNA
<213> ORGANISM: Artificial Sequence
<220> FEATURE:
<223> OTHER INFORMATION: Substrate

<400> SEQUENCE: 94
aaccucaaag aaaaaccaaa cguaacacca a                            31

<210> SEQ ID NO 95
<211> LENGTH: 44
<212> TYPE: DNA
<213> ORGANISM: Artificial Sequence
<220> FEATURE:
<223> OTHER INFORMATION: Substrate

<400> SEQUENCE: 95
gggaucgaag auucgugaca guccuguuua cucguuaugu cagg              44

<210> SEQ ID NO 96
<211> LENGTH: 44
<212> TYPE: DNA
<213> ORGANISM: Artificial Sequence
<220> FEATURE:
<223> OTHER INFORMATION: Substrate

<400> SEQUENCE: 96
gggaucgaag auucgugaca guccuguuua cucguuaugu cagg              44

<210> SEQ ID NO 97
<211> LENGTH: 46
<212> TYPE: DNA
<213> ORGANISM: Artificial Sequence
<220> FEATURE:
<223> OTHER INFORMATION: Sustrate

<400> SEQUENCE: 97
gggucuaugu acaagcacuu cuguuucccc ggagcgaggu augccg            46

<210> SEQ ID NO 98
<211> LENGTH: 67
<212> TYPE: DNA
<213> ORGANISM: Artificial Sequence
<220> FEATURE:
<223> OTHER INFORMATION: Hammerhead ribozyme - (cleavage activity)

<400> SEQUENCE: 98
gggccaaacg uucuuggguu gucugaugag uccgugagga cgaaacguuu gguuuucuu    60 ugagguu                                                             67

<210> SEQ ID NO 99
<211> LENGTH: 70
<212> TYPE: DNA
<213> ORGANISM: Artificial Sequence
<220> FEATURE:
<223> OTHER INFORMATION: Hairpin Rz (cleavage activity)

<400> SEQUENCE: 99

```
gacauaacga guaaacagag aagucaacca gagaaacaca cguuguggua cauuaccugg    60
uacuucucug                                                           70

<210> SEQ ID NO 100
<211> LENGTH: 82
<212> TYPE: DNA
<213> ORGANISM: Artificial Sequence
<220> FEATURE:
<223> OTHER INFORMATION: Hairpin Rz (ligation activity)

<400> SEQUENCE: 100
gacauaacga guaaacagag aagucaacca gagaaacaca cguuguggua cauuaccugg    60
uacuucucug cgaaucuucg au                                             82

<210> SEQ ID NO 101
<211> LENGTH: 55
<212> TYPE: DNA
<213> ORGANISM: Artificial Sequence
<220> FEATURE:
<223> OTHER INFORMATION: DNazyme (cleavage activity)

<400> SEQUENCE: 101
cggcataact cgctccgggg aaaggctagc tacaacgaag aagtgctttc cccgg         55

<210> SEQ ID NO 102
<211> LENGTH: 25
<212> TYPE: DNA
<213> ORGANISM: Artificial Sequence
<220> FEATURE:
<223> OTHER INFORMATION: Si RNA

<400> SEQUENCE: 102
gggcggcggu ugguguuacg uuugg                                          25

<210> SEQ ID NO 103
<211> LENGTH: 53
<212> TYPE: DNA
<213> ORGANISM: Artificial Sequence
<220> FEATURE:
<223> OTHER INFORMATION: Si RNA (off)

<400> SEQUENCE: 103
gggccaaacg uaagggcggc gguuggaguu acguuugguu uuucuuugag guu           53

<210> SEQ ID NO 104
<211> LENGTH: 59
<212> TYPE: DNA
<213> ORGANISM: Artificial Sequence
<220> FEATURE:
<223> OTHER INFORMATION: Substrate

<400> SEQUENCE: 104
gggaugagca caaauccuaa accucaaaga aaaaccaaac guaacaccaa ccgccgccc     59
```